(12) United States Patent
Glenn et al.

(10) Patent No.: US 7,527,802 B2
(45) Date of Patent: May 5, 2009

(54) VACCINE FOR TRANSCUTANEOUS IMMUNIZATION

(75) Inventors: Gregory M. Glenn, Poolesville, MD (US); Frederick J. Cassels, Laurel, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/467,887

(22) PCT Filed: Feb. 13, 2002

(86) PCT No.: PCT/US02/04254

§ 371 (c)(1),
(2), (4) Date: Mar. 22, 2004

(87) PCT Pub. No.: WO02/064162

PCT Pub. Date: Aug. 22, 2002

(65) Prior Publication Data

US 2004/0146534 A1    Jul. 29, 2004

Related U.S. Application Data

(60) Provisional application No. 60/310,447, filed on Aug. 8, 2001, provisional application No. 60/310,483, filed on Aug. 8, 2001, provisional application No. 60/304,110, filed on Jul. 11, 2001, provisional application No. 60/268,016, filed on Feb. 13, 2001.

(51) Int. Cl.
| | |
|---|---|
| A61K 39/38 | (2006.01) |
| A61K 39/02 | (2006.01) |
| A61K 39/385 | (2006.01) |
| A61K 39/108 | (2006.01) |
| A61K 38/00 | (2006.01) |
| A61K 9/70 | (2006.01) |
| A61K 9/127 | (2006.01) |
| A61F 13/00 | (2006.01) |
| A01N 37/18 | (2006.01) |
| A01N 63/00 | (2006.01) |
| A01N 65/00 | (2006.01) |
| A61B 17/20 | (2006.01) |
| A61M 37/00 | (2006.01) |

(52) U.S. Cl. ............. 424/257.1; 424/184.1; 424/242.1; 424/234.1; 424/190.1; 424/93.1; 424/241.1; 424/235.1; 424/194.1; 424/449; 424/450; 514/2; 514/12; 604/46

(58) Field of Classification Search ............. 424/184.1, 424/242.1, 257.1, 234.1, 169.1, 190.1, 93.1, 424/241.1, 194.1, 449, 450; 514/2, 12

See application file for complete search history.

(56) References Cited

U.S. PATENT DOCUMENTS

| | | | |
|---|---|---|---|
| 3,837,340 A | | 9/1974 | Counter |
| 3,948,263 A | | 4/1976 | Drake |
| 3,964,482 A | | 6/1976 | Gerstel et al. |
| 3,982,536 A | | 9/1976 | Krogseng |
| 4,196,191 A | | 4/1980 | Almeida |
| 4,220,584 A | | 9/1980 | Limjuco |
| 4,235,871 A | | 11/1980 | Papahadjopoulos |
| 4,285,931 A | * | 8/1981 | Limjuco et al. .......... 424/241.1 |
| 4,394,448 A | | 7/1983 | Szoka |
| 4,411,888 A | | 10/1983 | Klipstein |
| 4,455,142 A | | 6/1984 | Martins |
| 4,484,923 A | | 11/1984 | Amkraut |
| 4,497,796 A | | 2/1985 | Salser |
| 4,587,044 A | | 5/1986 | Miller |
| 4,692,462 A | | 9/1987 | Banerjee |
| 4,725,271 A | | 2/1988 | Korol |
| 4,732,892 A | | 3/1988 | Sarpotdar |
| 4,743,588 A | | 5/1988 | Mirejovsky |
| 4,761,372 A | | 8/1988 | Maas |
| 4,764,381 A | | 8/1988 | Bodor |
| 4,783,450 A | | 11/1988 | Fawzi |
| 4,834,985 A | | 5/1989 | Eiger |
| 4,876,278 A | | 10/1989 | Taylor |
| 4,877,612 A | | 10/1989 | Berger |

(Continued)

FOREIGN PATENT DOCUMENTS

| | | |
|---|---|---|
| AU | 47099/89 | 6/1990 |

(Continued)

OTHER PUBLICATIONS

Liu et al, Acta Biochimica et Biophysica Sinica, 2003, 35/1:49-54 abstract only.*

(Continued)

*Primary Examiner*—N. M Minnifield
(74) *Attorney, Agent, or Firm*—Morgan, Lewis & Bockius LLP

(57) ABSTRACT

A vaccine delivered by transcutaneous immunization provides an effective treatment against infections by pathogens such as, for example, enterotoxigenic *Escherichia coli* (ETEC) and/or for symptoms of diarrheal disease caused thereby. For example, one, two, three, four, five or more antigens derived from ETEC and capable of inducing an antigen-specific immune response (e.g., toxins, colonization or virulence factors) and one or more optional adjuvant (e.g., whole bacterial ADP-ribosylating exotoxins, B subunits or toxoids thereof, detoxified mutants and derivatives thereof) are used to manufacture vaccines or to induce systemic and/or mucosal immunity.

17 Claims, 33 Drawing Sheets

U.S. PATENT DOCUMENTS

| | | |
|---|---|---|
| 4,887,611 A | 12/1989 | Rudiger et al. |
| 4,892,737 A | 1/1990 | Bodor |
| 4,904,448 A | 2/1990 | Kawahara |
| 4,908,389 A | 3/1990 | Mahjour |
| 4,917,688 A | 4/1990 | Nelson |
| 4,917,895 A | 4/1990 | Lee |
| 4,921,757 A | 5/1990 | Wheatley |
| 4,929,442 A | 5/1990 | Powell |
| 4,946,853 A | 8/1990 | Bannon |
| 4,956,171 A | 9/1990 | Chang |
| 4,960,771 A | 10/1990 | Rajadhyaksha |
| 4,970,206 A | 11/1990 | Alexander |
| 5,003,987 A | 4/1991 | Grinwald |
| 5,008,050 A | 4/1991 | Cullis |
| 5,008,111 A | 4/1991 | Bodor |
| 5,023,252 A | 6/1991 | Hseih |
| 5,028,435 A | 7/1991 | Katz |
| 5,030,629 A | 7/1991 | Rajadhyaksha |
| 5,032,401 A | 7/1991 | Jamas |
| 5,032,402 A | 7/1991 | Digenis |
| 5,041,439 A | 8/1991 | Kasting |
| 5,045,317 A | 9/1991 | Chess |
| 5,049,386 A | 9/1991 | Eppstein |
| 5,049,387 A | 9/1991 | Amkraut |
| 5,059,189 A | 10/1991 | Cilento |
| 5,059,421 A | 10/1991 | Loughrey |
| 5,069,904 A | 12/1991 | Masterson |
| 5,082,866 A | 1/1992 | Wong |
| 5,108,921 A | 4/1992 | Low |
| 5,133,970 A | 7/1992 | Petereit et al. |
| 5,142,044 A | 8/1992 | Minaskanian |
| 5,162,315 A | 11/1992 | Rajadhyaksha |
| 5,164,406 A | 11/1992 | Helman |
| 5,166,320 A | 11/1992 | Wu |
| 5,169,637 A | 12/1992 | Lenk |
| 5,182,109 A * | 1/1993 | Tamura et al. ......... 424/197.11 |
| 5,196,410 A | 3/1993 | Francoeur |
| 5,200,393 A | 4/1993 | Weiner |
| 5,204,339 A | 4/1993 | Minaskanian |
| 5,215,520 A | 6/1993 | Shroot |
| 5,225,182 A | 7/1993 | Sharma |
| 5,232,935 A | 8/1993 | Colas |
| 5,234,959 A | 8/1993 | Minaskanian |
| 5,238,944 A | 8/1993 | Wick |
| 5,240,846 A | 8/1993 | Collins |
| 5,250,023 A | 10/1993 | Lee et al. |
| 5,252,334 A | 10/1993 | Chiang |
| 5,256,422 A | 10/1993 | Albert |
| 5,260,066 A | 11/1993 | Wood |
| 5,270,346 A | 12/1993 | Minaskanian |
| 5,279,544 A | 1/1994 | Gross et al. |
| 5,308,835 A | 5/1994 | Clements |
| 5,326,566 A | 7/1994 | Parab |
| 5,326,790 A | 7/1994 | Thornfeldt |
| 5,328,470 A | 7/1994 | Nabel |
| 5,332,576 A | 7/1994 | Mantelle |
| 5,332,577 A | 7/1994 | Gertner |
| 5,340,588 A | 8/1994 | Domb |
| 5,352,449 A | 10/1994 | Beltz |
| 5,399,346 A | 3/1995 | Anderson |
| 5,411,738 A | 5/1995 | Hind |
| 5,428,132 A | 6/1995 | Hirsch |
| 5,445,611 A | 8/1995 | Eppstein |
| 5,458,140 A | 10/1995 | Eppstein |
| 5,462,743 A | 10/1995 | Turner |
| 5,464,386 A | 11/1995 | Hofmann |
| 5,472,946 A | 12/1995 | Peck |
| 5,482,965 A | 1/1996 | Rajadhyaksha |
| 5,492,698 A | 2/1996 | Von Kleinsorgen |
| 5,505,956 A | 4/1996 | Kim |
| 5,505,958 A | 4/1996 | Bello |
| 5,518,725 A | 5/1996 | Daynes |
| 5,533,995 A | 7/1996 | Corish |
| 5,534,260 A | 7/1996 | Petersen |
| 5,536,263 A | 7/1996 | Rolf |
| 5,540,931 A | 7/1996 | Hewitt |
| 5,547,932 A | 8/1996 | Curiel |
| 5,573,778 A | 11/1996 | Therriault |
| 5,578,475 A | 11/1996 | Jessee |
| 5,580,859 A | 12/1996 | Felgner |
| 5,589,466 A | 12/1996 | Felgner |
| 5,593,972 A | 1/1997 | Weiner |
| 5,601,827 A | 2/1997 | Collier |
| 5,607,691 A | 3/1997 | Hale |
| 5,612,382 A | 3/1997 | Fike |
| 5,614,212 A | 3/1997 | D'Angelo |
| 5,614,503 A | 3/1997 | Chaudhary |
| 5,620,896 A | 4/1997 | Herrmann |
| 5,626,866 A | 5/1997 | Ebert |
| 5,643,578 A | 7/1997 | Robinson |
| 5,658,587 A | 8/1997 | Santus |
| 5,661,025 A | 8/1997 | Szoka |
| 5,661,130 A | 8/1997 | Meezan |
| 5,674,503 A | 10/1997 | Olafson |
| 5,676,954 A | 10/1997 | Brigham |
| 5,679,647 A | 10/1997 | Carson |
| 5,686,100 A | 11/1997 | Wille |
| 5,688,523 A | 11/1997 | Garbe et al. |
| 5,693,024 A | 12/1997 | Flower |
| 5,693,622 A | 12/1997 | Wolff |
| 5,695,991 A | 12/1997 | Lindholm |
| 5,697,901 A | 12/1997 | Eriksson |
| 5,698,416 A | 12/1997 | Wolf |
| 5,703,057 A | 12/1997 | Johnston |
| 5,705,151 A | 1/1998 | Dow |
| 5,718,914 A | 2/1998 | Foldvari |
| 5,720,948 A | 2/1998 | Brucks |
| 5,722,397 A | 3/1998 | Eppstein |
| 5,723,114 A | 3/1998 | Thornfeldt |
| 5,731,303 A | 3/1998 | Hsieh |
| 5,733,572 A | 3/1998 | Unger |
| 5,733,762 A | 3/1998 | Midoux |
| 5,736,154 A | 4/1998 | Fuisz |
| 5,736,392 A | 4/1998 | Hawley-Nelson |
| 5,736,524 A | 4/1998 | Content |
| 5,738,647 A | 4/1998 | Bernhard |
| 5,739,118 A | 4/1998 | Carrano |
| 5,741,510 A | 4/1998 | Rolf |
| 5,756,117 A | 5/1998 | D'Angelo |
| 5,760,096 A | 6/1998 | Thornfeldt |
| 5,766,899 A | 6/1998 | Kuo |
| 5,770,580 A | 6/1998 | Ledley |
| 5,773,022 A | 6/1998 | Nyqvist-Mayer |
| 5,780,050 A | 7/1998 | Jain |
| 5,783,567 A | 7/1998 | Hedley |
| 5,789,230 A | 8/1998 | Cotton |
| 5,804,214 A | 9/1998 | Wong |
| 5,804,566 A | 9/1998 | Carson |
| 5,811,406 A | 9/1998 | Szoka |
| 5,814,599 A | 9/1998 | Mitragotri |
| 5,814,617 A | 9/1998 | Hoffman |
| 5,824,538 A | 10/1998 | Branstrom |
| 5,827,703 A | 10/1998 | Debs |
| 5,827,705 A | 10/1998 | Dean |
| 5,830,876 A | 11/1998 | Weiner |
| 5,830,877 A | 11/1998 | Carson |
| 5,834,010 A | 11/1998 | Quan |
| 5,837,289 A | 11/1998 | Grasela |
| 5,837,533 A | 11/1998 | Boutin |
| 5,840,059 A | 11/1998 | March |
| 5,843,913 A | 12/1998 | Li |
| 5,844,107 A | 12/1998 | Hanson |
| 5,846,540 A | 12/1998 | Restifo |
| 5,846,949 A | 12/1998 | Wagner |

| | | | |
|---|---|---|---|
| 5,849,719 A | 12/1998 | Carson | |
| 5,853,751 A | 12/1998 | Masiz | |
| 5,856,187 A | 1/1999 | Restifo | |
| 5,858,784 A | 1/1999 | Debs | |
| 5,866,553 A | 2/1999 | Donnelly | |
| 5,877,159 A | 3/1999 | Powell | |
| 5,877,302 A | 3/1999 | Hanson | |
| 5,879,326 A | 3/1999 | Godshall et al. | |
| 5,885,971 A | 3/1999 | German | |
| 5,910,306 A * | 6/1999 | Alving et al. | 424/184.1 |
| 5,910,488 A | 6/1999 | Nabel | |
| 5,914,114 A | 6/1999 | Cassels | 424/241.1 |
| 5,916,879 A | 6/1999 | Webster | |
| 5,935,838 A | 8/1999 | Askeloef | |
| 5,961,979 A | 10/1999 | Srivastava | |
| 5,980,898 A * | 11/1999 | Glenn et al. | 424/184.1 |
| 5,985,847 A | 11/1999 | Carson | |
| 5,993,849 A | 11/1999 | Assmus et al. | |
| 5,993,852 A | 11/1999 | Foldvari et al. | |
| 6,019,982 A | 2/2000 | Clements et al. | |
| 6,022,316 A | 2/2000 | Eppstein et al. | |
| 6,033,673 A | 3/2000 | Clements | |
| 6,033,684 A | 3/2000 | Norcia | |
| 6,039,969 A | 3/2000 | Tomai | |
| 6,063,399 A | 5/2000 | Assmus et al. | |
| 6,087,341 A | 7/2000 | Khavari | |
| 6,090,790 A | 7/2000 | Eriksson | |
| 6,142,939 A | 11/2000 | Eppstein et al. | |
| 6,149,919 A | 11/2000 | Domenighini et al. | |
| 6,165,458 A | 12/2000 | Foldvari et al. | |
| 6,165,500 A | 12/2000 | Cevc | |
| 6,173,202 B1 | 1/2001 | Eppstein | |
| 6,180,136 B1 | 1/2001 | Larson | |
| 6,190,367 B1 | 2/2001 | Hall | |
| 6,190,689 B1 | 2/2001 | Hoffmann et al. | |
| 6,207,184 B1 | 3/2001 | Ikeda et al. | |
| 6,210,672 B1 | 4/2001 | Cowing | |
| 6,256,533 B1 | 7/2001 | Yuzhakov et al. | |
| 6,290,991 B1 | 9/2001 | Roser et al. | |
| 6,312,612 B1 | 11/2001 | Sherman et al. | |
| 6,331,266 B1 | 12/2001 | Powell et al. | |
| 6,331,310 B1 | 12/2001 | Roser et al. | |
| 6,334,856 B1 | 1/2002 | Allen et al. | |
| 6,348,212 B2 | 2/2002 | Hymes et al. | |
| 6,348,450 B1 | 2/2002 | Tang et al. | |
| 6,365,178 B1 | 4/2002 | Venkateshwaran et al. | |
| 6,379,324 B1 | 4/2002 | Gartstein et al. | |
| 6,406,705 B1 | 6/2002 | Davis et al. | |
| 6,413,523 B1 | 7/2002 | Clements | |
| 6,440,096 B1 | 8/2002 | Lastovich et al. | |
| 6,451,240 B1 | 9/2002 | Sherman et al. | |
| 6,454,755 B1 | 9/2002 | Godshall | |
| 6,471,903 B2 | 10/2002 | Sherman et al. | |
| 6,797,276 B1 * | 9/2004 | Glenn et al. | 424/278.1 |
| 6,869,602 B2 * | 3/2005 | Ryu et al. | 424/93.73 |
| 7,037,499 B1 * | 5/2006 | Glenn et al. | 424/184.1 |
| 7,217,541 B2 * | 5/2007 | Cassels et al. | 435/71.1 |
| 7,399,474 B2 * | 7/2008 | Altboum et al. | 424/190.1 |
| 2003/0157159 A1 * | 8/2003 | Franklin et al. | 424/450 |
| 2004/0005662 A1 * | 1/2004 | Cassels et al. | 435/69.1 |
| 2004/0028727 A1 * | 2/2004 | Glenn et al. | 424/449 |
| 2004/0109869 A1 * | 6/2004 | Glenn et al. | 424/185.1 |
| 2004/0137004 A1 * | 7/2004 | Glenn et al. | 424/184.1 |
| 2004/0146534 A1 * | 7/2004 | Glenn et al. | 424/257.1 |
| 2004/0258703 A1 * | 12/2004 | Glenn et al. | 424/184.1 |
| 2005/0074462 A1 * | 4/2005 | Holmgren et al. | 424/185.1 |
| 2005/0287157 A1 * | 12/2005 | Glenn et al. | 424/184.1 |
| 2006/0002949 A1 * | 1/2006 | Glenn et al. | 424/185.1 |
| 2006/0002959 A1 * | 1/2006 | Glenn et al. | 424/209.1 |
| 2006/0002960 A1 * | 1/2006 | Zoeteweij et al. | 424/235.1 |
| 2007/0088248 A1 * | 4/2007 | Glenn et al. | 604/46 |

FOREIGN PATENT DOCUMENTS

| | | |
|---|---|---|
| EP | 0 891 770 | 1/1999 |
| EP | 1356821 A2 * | 10/2003 |
| JP | 04187640 | 10/1993 |
| WO | WO 92/03122 | 3/1992 |
| WO | WO 94/21230 | 9/1994 |
| WO | WO 95/17211 | 6/1995 |
| WO | WO 95/18603 | 7/1995 |
| WO | WO 96/06627 | 3/1996 |
| WO | WO 96/19976 | 4/1996 |
| WO | WO 96/14704 | 5/1996 |
| WO | WO 96/14855 | 5/1996 |
| WO | WO 96/25190 | 8/1996 |
| WO | WO 96/39189 A1 * | 12/1996 |
| WO | WO 96/39190 A1 * | 12/1996 |
| WO | WO 97/04832 | 2/1997 |
| WO | WO 97/07734 | 3/1997 |
| WO | WO 97/24447 | 7/1997 |
| WO | WO 97/31119 | 8/1997 |
| WO | WO 97/35957 | 10/1997 |
| WO | WO 98/00193 | 1/1998 |
| WO | WO 98/01538 | 1/1998 |
| WO | WO 98/10750 | 3/1998 |
| WO | WO 98 20734 | 5/1998 |
| WO | WO 98/20734 | 5/1998 |
| WO | WO 98/29134 | 7/1998 |
| WO | WO 98/42375 | 10/1998 |
| WO | WO 98/46208 | 10/1998 |
| WO | WO 99/04009 | 1/1999 |
| WO | WO 99/08689 | 2/1999 |
| WO | WO 99/08713 | 2/1999 |
| WO | WO 99/13915 | 3/1999 |
| WO | WO 99/26662 | 6/1999 |
| WO | WO 99/41366 | 8/1999 |
| WO | WO 99/43350 | 9/1999 |
| WO | WO 99 43350 | 9/1999 |
| WO | WO 99/47164 | 9/1999 |
| WO | WO 99/47165 | 9/1999 |
| WO | WO 99/47167 | 9/1999 |
| WO | WO 99/53960 | 10/1999 |
| WO | WO 99/60167 | 11/1999 |
| WO | WO 99/61078 | 12/1999 |
| WO | WO 99/62537 | 12/1999 |
| WO | WO 00/33812 | 6/2000 |
| WO | WO 00/37106 A1 * | 6/2000 |
| WO | WO 00/44349 | 8/2000 |
| WO | WO 00/61184 | 10/2000 |
| WO | WO 00/61184 A2 * | 10/2000 |
| WO | WO 00/74714 | 12/2000 |
| WO | WO 00/74763 | 12/2000 |
| WO | WO 00/74763 A3 | 12/2000 |
| WO | WO 00/74766 | 12/2000 |
| WO | WO 01/34185 | 5/2001 |
| WO | WO 01/90758 | 11/2001 |
| WO | WO 02/02179 | 1/2002 |
| WO | WO 02/05889 | 1/2002 |
| WO | WO 02/07813 | 1/2002 |
| WO | WO 02/064162 | 8/2002 |
| WO | WO 02/064162 A2 * | 8/2002 |
| WO | WO 02/064193 | 8/2002 |
| WO | WO 02/074244 | 9/2002 |

OTHER PUBLICATIONS

Serichantalergs et al, J. CLinical Microbiology, 1997, 35/6:1639-1641.*
Svennerholm et al, Best Practice and Research Clinical Gastroenterology, 2004, 18/2:421-445.*
Scerpella et al, J. Travel Med., 1995, 2:22-27.*
Sanchez et al, Current Opinion Immunology, 2005, 17:388-398.*
Robertson et al, Vaccine, 2002, 20:31-41.*

Katz et al, Vaccine, 2003, 21:341-346.*
Byrd et al, Vaccine, 2003, 21:1884-1893.*
Wiedermann et al, J. Travel Med., 2000, 7:27-29.*
Paul et al, Vaccine Research, 1993, 4/3:145-1164.*
Paul et al, European J. Immunology, 1995, 25/8:3521-3524.*
Boedeker, Current Opinion in Gastroenterology, 2005, 21/1:15-19.*
Tacket et al, Vaccine, 1994, 12/14:1270-1274.*
Cassels et al, J. Industrail Microbiology and Biotechnology, 1997, 19:66-70.*
Wolf et al, J. Clin. Microbiol., 1993, 31/4:851-856.*
Cassels et al, Infection and Immunity,, 1992, 60/6:2174-2181.*
Alves et al, Vaccine, 2001, 19:788-795.*
Subekti et al, Diagnostic Microbiology and Infectious Disease, 2003, 47:399-405.*
Barry et al, Vaccine, 2003, 21:333-340.*
de Lorimier et al, Vaccine, 2003, 21:2548-2555.*
Lasaro et al, Vaccine, 2005, 23:2430-2438.*
Byrd et al, Advanced Drug Delivery Reviews, 2005, 57:1362-1380.*
Sizemore et al, Expert Rev. Vaccines, 2004, 3/5:585-595.*
Gaastra et al, Trends in Microbiology, 1996, 4/11:444-452.*
Qadri et al, Vaccine, 2000, 18:2704-2712.*
Kersten et al, Expert Rev. Vaccines, 2004, 3/4:453-462.*
Belyakov et al, J. Clinical Investigation, 2004, 113/7:998-1007.*
Anantha et al, Infection and Immunity, 2004, 72/12:7190-7201.*
Schultsz et al, J. Clinical Microbiology, 2000, 38/10:3550-3554.*
Guerena-Burgueno et al, Infection and Immunity, 2002, 70/4:1874-1880.*
Chen et al, Vaccine, 2001, 19:2908-2917.*
Yu et al, Infection and Immunity, 2002, 70/3:1056-1068.*
Glenn et al, Infection and Immunity, 1999, 67/3:1100-1106.*
Glenn et al, Nature, 1998, 391/6670:851.*
Glenn et al, J. Immunology, 1998, 161:3211-3214.*
Paton et al, Gastroenterology, 2005, 128:1219-1228.*
Rao et al, J. Infectious Diseases, 2005, 191: 562-570.*
Glenn et al, Immunol. Allergy Clin. N. Am., 2003, 23:787-813.*
Jertborn et al, VAccine, 1998, 16(2/3):255-260.*
Aranda-Michel et al, Am. J. Med., 1999, 106:670-676.*
McKenzie et al, Vaccine, 2007, 25:3684-3691.*
Warger et al, Immunology Letters, 2007, 109:13-20.*
Roland et al, Vaccine, 2007, 25:8574-8584.*
Steinsland et al, Lancet, 2003, 362:286-291.*
Shaheen et al, Int. J. Infect. Dis., 2003, 7:35-41.*
Sack et al, Johns Hopkins Medical Journal, 1977, 141:63-70.*
Glenn et al, Expert Review of Vaccines, Oct. 2007, 6/5:809-819.*
Scharton-Kersten et al. (2000) Transcutaneous immunization with bacterial ADP-ribosylating exotoxins, subunits and unrelated adjuvants. Infect. Immun. 68(9):5306-5313, American Society for Microbiology, Washington, D.C., USA.
Becker "Dengue fever virus and Japanese encephalitis virus synthetic peptides, with motifs to fit HLA class 1 haplotypes prevalent in human populations in endemic regions, can be used for application to skin Langerhans cells to prime antiviral CD8 cytotoxic T cells (CTLs)—A novel approach to the protection of humans" Virus Genes 9:33-45 (1994).
Becker "An analysis of the role of skin Langerhans cells (LC) in the cytoplasmic processing of HIV-1 peptides after "Peplotion" transepidermal transfer and HLA class I presentation to CD8 CTLs—An approach to immunization of humans" Virus Genes 9:133-147 (1994).
U.S. Appl. No. 60/075,850, filed Feb. 1998, Glenn.
U.S. Appl. No. 60/075,856, filed Feb. 1998, Glenn.
Alving "Effectiveness of liposomes as potential carriers of vaccines: Applications to cholera toxin and human malaria sporozoite antigent" Vaccine 4:166-172 (1986).
Alving "Liposomes as carriers of antigens and adjuvants" J. Immunol. Methods 140:1-13 (1991).
Alving "Lipopolysaccharide, lipid A, and liposomes containing lipid A as immunologic adjuvants" Immunobioly 187: 430-446 (1993).
Alving "Novel adjuvant strategies for experimental malaria and AIDS vaccines" Ann. NY Acad. Sci. 690:265-275 (1993).
Alving "The preparation and use of liposomes in immunological studies" in: *Liposome Technology*, CRC Press 3:317-343 (1993).
Alving "Cytotoxic T lymphocytes induced by liposomal antigens: Mechanisms of immunological presentation" AIDS Res Hum Retroviruses 10 suppl 2 S91-S94 (1994).
Alving "Liposomes as carriers of peptide antigens: induction of antibodies and cytotoxic T lymphocytes to conjugated and unconjugated peptides" Immunol Rev 145:5-31 (1995).
Allison "Hydrogen bonding between sugar and protein is responsible for inhibition of dehydration-induced protein unfolding" Arch. Biochem, Biophys. 365:289-298 (1999).
Allison "Optimization of storage stability of lyophilized actin using combinations of disaccharides and dextran" J. Pharm. Sci. 89:199-214 (2000).
Anderson "Guinea Pig Maximization Test: Effect TRype of Freund's Complete AdjuvantEmulsion and of Challenge Site Location" Dermatosen 33: 132-136 (1985).
Andya "The effect of formulation excipients on protein stability and aerosol performance of spray-dried powders of a recombinant humanized anti-IgE monocional antibody" Pharm. Res. 16:350-358 (1999).
Arakawa "Protein-solvent interactions in pharmaceutical formulations" Pharm. Res. 8:285-291 (1999).
Arany "Correlation between pretreatment levels of interferon response genes and clinical responses to an immune response modifier (imiquimod) in genital warts" Antimicrob Agents Chemother 44:1869-1873 (2000).
Artmann "Liposomes from soya phospholipids as percutaneous drug carriers. 1st communication: qualitative in vivo investigations with antibody-loaded liposomes" Arzneimittelforschung 40: 1363-1365 (1990).
Becker "Dengue fever virus and Japanese encephalitis virus synthetic peptides, with motifs to fit HLA class 1 haplotypes prevalent in human populations in endemic regions, can be used for application to skin Langerhans cells to prime antiviral CD8 cytotoxic T cells (CTLs)—A novel approach to the protection of humans" Virus Genes 9:33-45 (1994).
Becker "An analysis of the role of skin Langerhans cells (LC) in the cytoplasmic processing of HIV-1 peptides after "Peplotation" transepidermal transfer and HLA class I presentation to CD8 CTLs—An approach to immunization of humans" Virus Genes 9:133-147 (1994).
Becker "HIV-Peplotion Vaccine" in Novel Strategies and Design and Production of Vaccines, ed. S. Cohen and A. Shafferman, Plenum Press NY 97-104 (1996).
Becker "Mechanism in allergic contact dermatitis" Exp. Dermatol. 2:63-69 (1993.
Birch "Trehaloses" Adv. Carb. Chem. Biochem. 18:201-225 (1993).
Blauvelt "Human Langerhans cells express E-cadherin" J. Invest. Dermatol. 104:293-296 (1995).
Bos "The 500 dalton rule for the skin penetration of chemical compounds and drugs" Exp. Dermatol. 9:165-169 (2000).
Bovsun "DNA vaccine rubbed on skin provokes immune response" Biotechnol Newswatch pp. 4 (Sep. 20, 1999).
Bowen "Cholera toxin acts as a potent adjuvant for the induction of cytotoxic T-lymphycte responses with non-replicating antigens" Immunol. 81:338-342 (1994).
Buates "Treatment of experimental Leishmaniasis with the immunomodulators imiquimod and S-28463: Efficacy and mode of action" J Infect Dis 179:1485-1494 (1999).
Castle "Clinical relevance of age-related immune dysfunction" Clin. Infect. Dis. 31:578-585 (2000).
Cevc "Transfersomes, liposomes and other lipid suspensions on the skin: permeation enhancement, vesicle penetration, and transdermal drug delivery" Crit. Rev. in Ther. Drug Carrier Sys. 13:257-388 (1996).
Chen "Adjuvation of epidermal powder immunization" Vaccine 19:2908-2917 (2001).
Chen "Serum and mucosal immune responses to an inactivated influenza virus vaccine induced by epidermal powder immunization" J Virol 75:7956-7965 (2001).
Chen "Induction of systemic immune responses in sheep by topical application of cholera toxin to skin" Vet Immunol Immunopathol 77:191-199 (2000).

Chin "Antibody response against *Pseudomonas aeruginosa* membrane proteins in experimentally infected sheep" Vet. Microbiol. 43:21-32 (1995).

Chin "Manipulating systemic and mucosal immune responses with skin-deliverable adjuvans" J. Biotechnol. 44:13-19 (1996).

Condon "DNA-based immunization by in vivo transfection of dendritic cells" Nature Med. 2:1122-1128 (1996).

Costantino "Effect of excipients on the stability and structure of lyophilized recombinant human growth hormone" J. Pharm. Sci. 87:1412-1420 (1998).

Craig "Cutaneous responses to cholera skin toxin in man, I. Responses in unimmunized American males" J. Infect. Dis. 125:203-215 (1972).

De Haan "Liposomes as an immunoadjuvant system for stimulation of mucosal and systemic antibody reponses against inactivated measles virus administered intranasally to mice" Vaccine 13:1320-1324 (1995).

Egbaria "Liposomes as topical drug delivery system" Adv Drug Delivery Rev 5:287-300 (1990).

El-Ghorr "Transcutaenous immunisation with herpes simplex virus stimulates immunity in mice" FEMS Immunol Med Micro 29:255-261 (2000).

Enk "An essential role for Langerhans cell-derived IL-1 beta in the initiation of primary immune responses in skin" J Immunol 151:2390-2398 (1993).

Fan "Immunization via hair follicles by topical application of naked DNA to normal skin" Nature Biotechnol 17:870-872 (1999).

Fleisher "Topical delivery of growth hormone releasing peptide using liposomal systems: An in vitro study using hairless mouse skin" Life Sci 57:1293-1297 (1995).

Frank "Long-Term stabilization of biologicals" Bio/Technology 12:253-256 (1994).

Gekko "Mechanism of protein stabilization by glycerol: Preferential hydration in glycerol-water mixtures" Biochemistry 20:4667-4676 (1981).

Glenn "Murine IgG subclass antibodies to antigens incorporated in liposomes containing lipid A" Immunol Lett 47:73-78 (1995).

Glenn "Skin immunization made possible by cholera toxin" Nature 391:851 (1998).

Glenn "Transcutaneous immunization with cholera toxin protects mice against lethal mucosal toxin challenge" J Immunol 161:3211-3214 (1998).

Glenn "Transcutaneous immunisation" Exp Opin Invest Drugs 8:797-805 (1999).

Glenn "Transcutaneous immunization" In: *The Journal Report*, NIAID, pp. 91-93 (2000).

Glenn "Transcutaneous immunization: A human vaccine delivery strategy using a patch" Nature Med 6:1403-1406 (2000).

Glenn "Transcutaneous immunization" In: *Vaccine Adjuvants*, Human Press pp. 315-326 (2000).

Glenn "Transcutaneous immunization" In: *New Vaccine Technologies*, Landes Biosciences pp. 292-304 (2001).

Glueck "Safety and Immunogenicity of intranasally administered inactivated trivalent virosome-formulated influenza vaccine *Escherichia coli* heat-labile toxin as a mucosal adjuvant" J Infect Dis 181:1129-1132 (2000).

Gockel "Transcutaneous immunization induces mucosal and systemic immunity: A potent method for targeting immunity to the female reproductive tract" Mol Immunol 37:537-544 (2000).

Goodnow "Chance encounters and organized rendezvous" Immunol Rev 156:5-10 (1997).

Grubauer "Lipid Content and Lipid Type as Determinants of the Epidermal Permeability Barrier" J. Lipid Res. 30: 89-96 (1989).

Gupta "Adjuvants for human vaccines—current status, problems and future prospects" Vaccine 13:1263-1276 (1995).

Hagiwar "Effectiveness and safety of mutant *Escherichia coli* heat-labile enterotoxin as an adjuvant for nasal influenza vaccine" Vaccine 19:2071-2079 (2001).

Hagiwara "Effects of intranasal administration of cholera toxin (or *Escherichia coli* heat-labile enterotoxin) B subunits supplemented with a trace amount of the holotoxin on the brain" Vaccine 19:1652-1660 (2001).

Hammond "Transcutaneous immunization of domestic animals: Opportunities and challenges" Adv Drug Delivery Rev 43:45-55 (2000).

Hammond "Transcutaneous immunization: T cell responses and boosting of existing immunity" Vaccine 19:2701-2707 (2001).

Hanson "Introduction to formulation of protein pharmaceuticals" In: *Stability in Protein Pharmaceuticals*, Plenum pp. 209-233 (1992).

Hioe "Comparison of adjuvant formulations of cytotoxic T cell induction using synthetic peptides" Vaccine 14:412-418 (1996).

Hoelzle "Increased accumulation of trehalose in rhizobia cultured under 1% oxygen" Appl Environ Microbiol 56:3213-3215 (1990).

Hsiung *Diagnostic Virology 3rd Ed.*, Yale Univ. Press pp. 29-34 (1982).

Iizuka "Two simple methods for the evaluation of topically active anti-inflammatory steroidal ointments" Agents Actions 11:254-259 (1981).

Izutsu "Increased stabilizing effects of amphiphilic excipients on freeze-drying of lactate dehydrogenase (LDH) by dispersion into sugar matrices" Pharm Res 12:838-843 (1995).

Kahan "Immunosuppressive therapy" Current Opin Immunobiology 4:553-560 (1992).

Katoh "Acute cutaneous barrier perturbation induces maturation of Langerhans' cells in hairless mice" Acta Derm Venereol (Stockh) 77:365-369 (1997).

Knop "Cellular and molecular mechanisms in the induction phase of contact sensitivity" Intl Arch Allergy Immunol 107:231-232 (1995).

Korting "Topical liposome drugs to come: what the patent literature tells us" J Am Acad Dermatol 25:1068-1071 (1991).

Korting "Interaction of liposomes with human epidermis reconstructed in vitro" Br J Dermatol 132:571-579 (1995).

Kosecka "Pertussis toxin stimulates hypersensitivity and enhances nerve-mediated antigen uptake in rat intestines" Am J Physiol 267:G745-G752 (1994).

Kumamoto "Induction of tumor-specific protective immunity by in situ Langerhans cell vaccine" Nature Biotech 20:64-69 (2002).

Lacroix "Presentation de Malades: Percuti B.C.G. Diagnostic (B.C.G. Patch)" Alger Medicale 56: 473-477 (1952) with English Translation.

Lane "In vitro-evaluation of human lymphocyte function" In: *Handbook of Experimental Immunology 4th Ed.*, vol. 2, Blackwell pp. 66.5-66.7 (1986).

Liu "Topical application of HIV DNA vaccine with cytokine-expression plasmids induces strong antigen-specific immune responses" Vaccine 20:42-48 (2002).

Lu "Mutant *Escherichia coli* heat-labile enterotoxin [LT (R192G)] enhances protective humoral and cellular immune responses to orally administered inactivated influenza vaccine" Vaccine 20:1019-1029 (2002).

Lüders "Untersuchungen zu einer Verbesserung der Tuberkulinprobe" Beitr. Klin. Tuberk. 134: 130-142 (1966) with English Translation.

Luo "Synthetic DNA delivery systems" Nature Biotechnol 18:33-37 (2000).

Mahmoud "Parasitic protozoa and helminths: Biological and immunological challenges" Science 246:1015-1022 (1989).

Marinaro "Mucosal effect of cholera toxin in mice results from induction of T helper 2 (Th2) cells and IL-4" J Immunol 155:4621-4629 (1995).

McCluskie "Route and method of delivery of DNA vaccine influence immune responses in mice and non-human primates" Mol Med 5:287-300 (1999).

Mengiardi "Virosomes as carriers for combined vaccines" Vaccine 13:1306-1315 (1995).

Menon "De Novo Sterologenesis in the Skin. II. Regulation by Cutaneous Barrier Requirements" J. Lipid Res. 26: 418-427 (1985).

Mitragotri "Ultra-Sound Mediated Transdermal Delivery" Science 269: 850-853 (1995).

Norimatsu "Effects of aluminum adjuvant on systemic reactions of lipopolysaccharides in swine" Vaccine 13:1325-1329 (1995).

Mezei "Liposomes—a selective drug delivery system for the topical route of administration, Lotion dosage form" Life Sci 26:1473-1477 (1980).

Moghimi "Current progress and future prospects of liposomes in dermal drug delivery" J Microencapsul 10:155-162 (1993).

Ockenhouse "Sequestrin, a CD36 recognition protein on *Plasmodium falciparum* malaria-infected erythcocytes identified by anti-idiotype antibodies" Proc Natl Acad Sci USA 88:3175-3179 (1991).

Paul "Transdermal immunization with large proteins by means of ultradeformable drug carriers" Eur J Immunol 25:3521-3524 (1995).

Paul "Noninvasive administration of protein antigens: Transdermal immunization with bovine serum albumum in transferosomes" Vaccine Res 4:145-164 (1995).

Peters "Dendritic cells: From ontogenetic orphans to myelomonocytic descendants" Immunol Today 17:273-278 (1996).

Podda "The adjuvanted influenza vaccines with novel adjuvants: Experience with the MF59-adjuvated vaccine" Vaccine 19:2673-2680 (2001).

Powers "In previously immunized elderly adults inactivated influenza A (H1N1) virus vaccines induce poor antibody responses that are not enhanced by liposome adjuvant" Vaccine 13:1330-1335 (1995).

Ranade "Drug delivery systems, 6. Transdermal drug delivery" J Clin Pharmacol 31:401-418 (1991).

Rao "Intracellular processing of liposome-encapsulated antigens by macrophages depends upon the antigen" Infect Immun 63:2396-2402 (1995).

Remington: The Science and Practice of Pharmacy, ed. Hoover, 2000, 20th ed., p. 843-844.

Sanchez "Formulation strategies for the stabilization of tetanus toxoid in poly(lactide-co-glycolide) microspheres" Intl J Pharm 185:255-266 (1999).

Sauzet "Long-lasting anti-viral cytotoxic T lympocytes induced in vivo with chimeric-multirestricted lipopeptides" Vaccine 13:1339-1345 (1995).

Schaefer-Korting "Liposome preparations: A step forward in topical drug therapy for skin disease?" J Am Acad Dermatol 21:1271-1275 (1989).

Scharton-Kersten "Principles of transcutaneous immunization using cholera toxin as an adjuvant" Vaccine 17 suppl 2:S237-S43 (1999).

Schmit "Bacterial toxins: Friends or foes" Emerging Infect Dis 5:224-234 (1999).

Scheuplein "Percutaneous Absorption After Twenty-five Years or 'Old Wine in New Wineskins'" J. Investig. Dermatol. 67: 31-38 (1976).

Schwarzenberger "Contact allergens and epidermal proinflammatory cytokines modulate Langerhans cell E-cadherin expression in situ" J Invest Dermatol 106:553-558 (1996).

Seo "Percutaenous peptide immunization via corneum barrier-disrupted murine skin for experimental tumor immunopropylaxis" Proc Natl Acad Sci USA 97:371-376 (2000).

Small, In: *Handbook of Lipid Research*, Plenum, 4:43-87 and 89-96.

Stacey "Macrophages ingest and are activated by bacterial DNA" J Immunol 157:2116-2122 (1996).

Steinman "Dendritic cells in the T-cell areas of lymphoid organs" Immunol Rev 156:25-37 (1997).

Stingl "The immune functions of epidermal cells" Immunol Ser 46:3-72 (1989).

Strange et al. "Staphylococcal Enterotoxin B Applied on Intact Normal and Intact Atopic Skin Induces Dermatitis" Arch. Dermatol. 132: 27-33 (1996).

Suzuki "Imiquimod, a topical immune response modifier, induces migration of Langerhans cells" J Invest Dermatol 114:135-141 (2000).

Takigawa "Percutaneous peptide immunization via corneum barrier-disrupted murine skin for experimental tumor immunoprophylaxis" Ann NY Acad Sci 941:139-146 (2001).

Tang et al. "Vaccination onto bare skin", Scientific Correspondence, Nature 388: 729-730 (1997).

"Tuberculin, Purified Protein Derivative, Tine Test" Physician's Desk Reference, 3 pages (2002).

Udey "Cadherins and Langerhans cell immunobiology" Clin Exp Immunol 107 suppl 1:6-8 (1997).

Vassell "Activation of Langerhans cells following transcutaneous immunization" 13 FASEB J A633 482.8 (1999).

Verma "Phagocytosis of liposomes by macrophages: intracellular fate of liposomal malaria antigen" Biochim Biophys Acta 1066:229-238 (1991).

Verma "Adjuvant effects of liposomes containing lipid A: enhancement of liposomal antigen presentation and recruitment of macrophages" Infect Immun 60:2438-2444 (1992).

Vutla "Transdermal iontophoretic delivery of enkephalin formulated in liposomes" J Pharm Sci 85:5-8 (1996).

Walker "The role of percutaneous penetration enhancers" Adv Drug Delivery Rev 18:295-301 (1996).

Wang "Induction of protective polycional antibodies by immunization with a *Plasmodium yoelii* circumsporozite protein multiple antigen peptide vaccine" J. Immunol 154:2784-2793 (1995).

Wang "Epicutaneous exposure of protein antigen induces a predominant Th2-like response with high IgE production in mice" J Immunol 156:4077-4082 (1996).

Wassef "Liposomes as carriers for vaccines" Immunomethods 4:217-222 (1994).

Watabe "Protection against influenza virus challenge by topical application of influenza DNA vaccine" Vaccine 19:4434-4444 (2001).

Weiner "Topical delivery of liposomally encapsulated interferon evaluated in a cutaneous herpes guinea pig model" Antimicrob Agents Chemotherap 33:1217-1221 (1989).

White "Induction of cytolytic and antibody responses using *Plasmodium falciparum* repeatless circumsporozoite protein encapsulated in liposomes" Vaccine 11:1341-1346 (1993).

White "Antibody and cytotoxic T-lympocyte responses to a single liposome associated peptide antigen" Vaccine 13:1111-1122 (1995).

Yasutomi "A vaccine-elicited, single viral epitope-specific cytotoxic T lymphocyte response does not protect against intravenous, cell-free simian immunodeficiency virus challenge" J Virol 69:2279-2284 (1995).

Zellmer "Interaction of phosphatidylcholine liposomes with the human stratum corneum" Biochim Biophys Acta 1237:176-182 (1995).

US 6,008,200, 12/1999, Krieg (withdrawn)

* cited by examiner

Anti-LT IgG

Anti-CS6 IgG

Anti-LT IgA

Anti-CS6 IgA

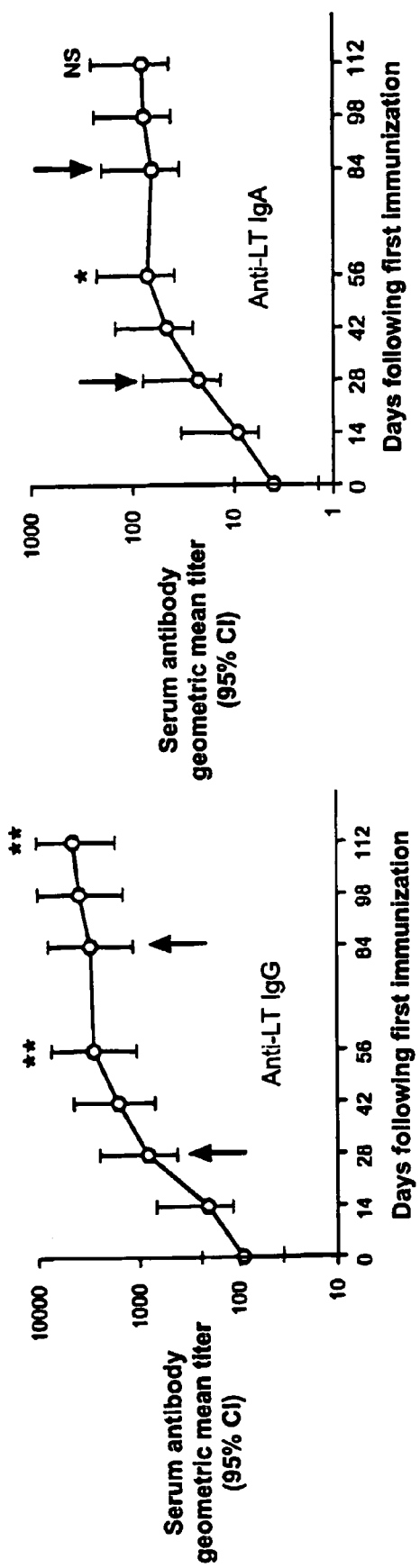
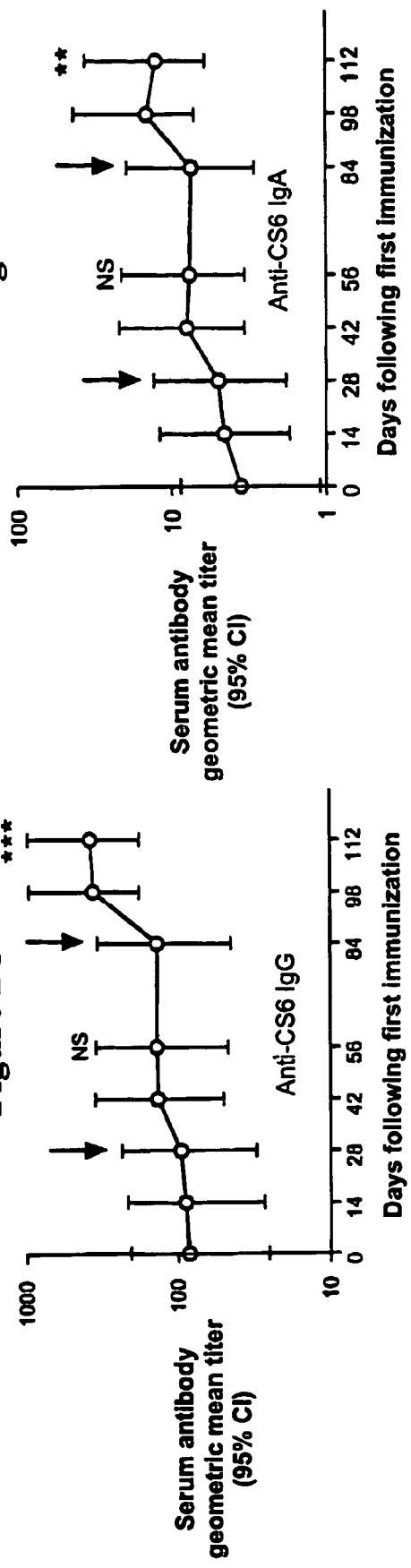
Figure 2A, Figure 2B, Figure 2C, Figure 2D

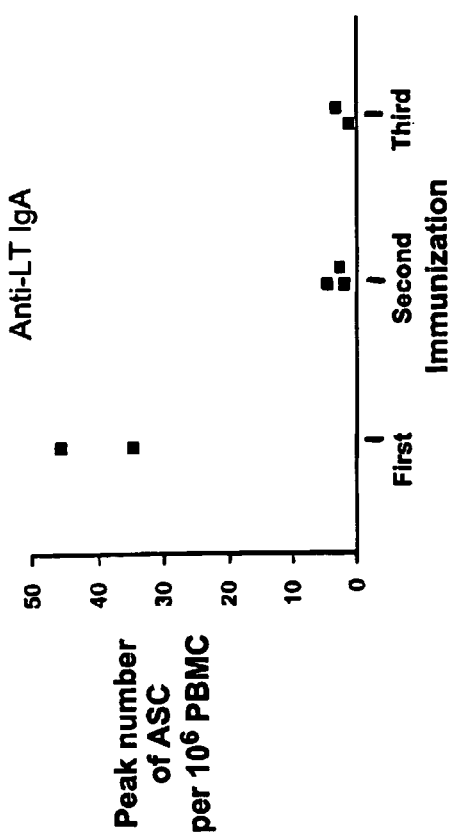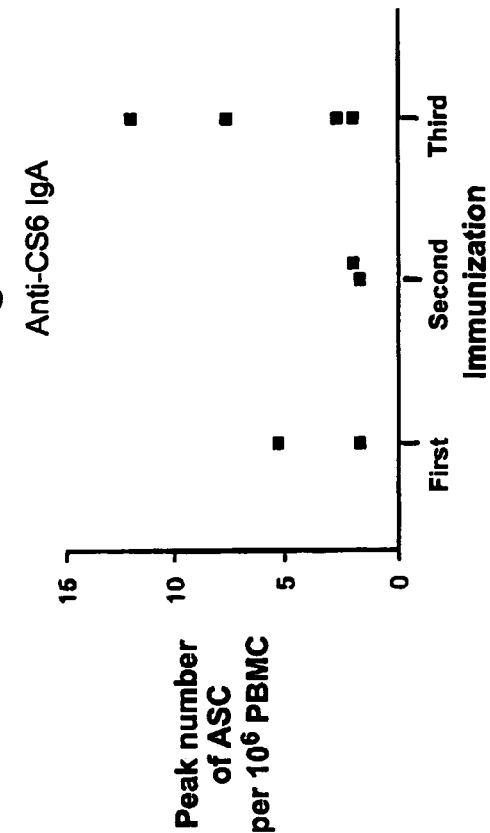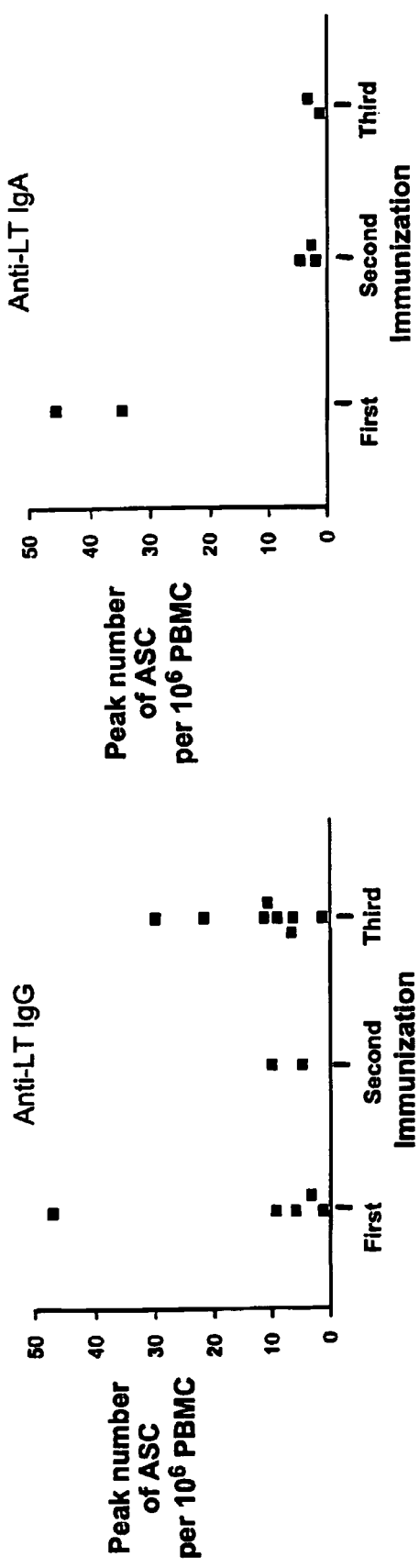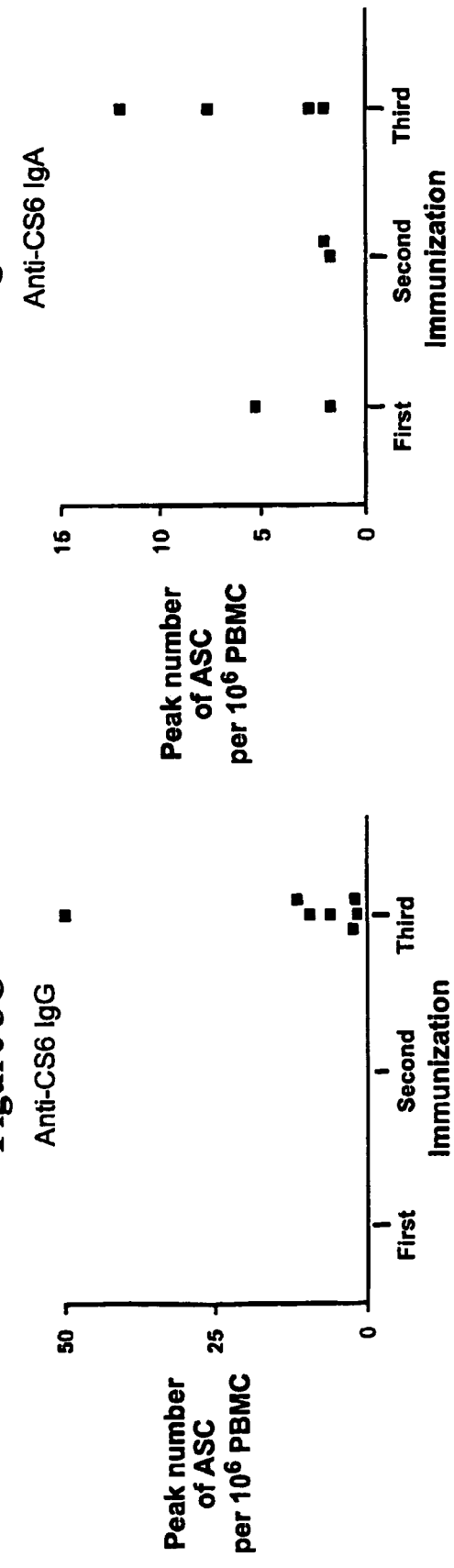

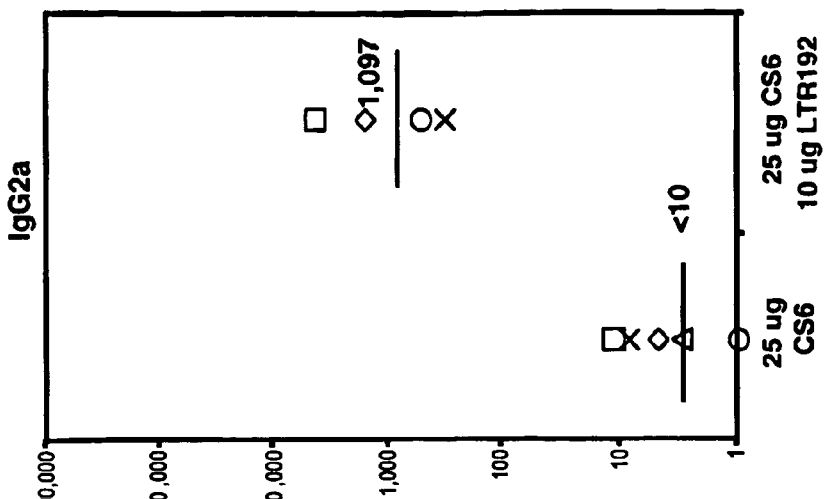
Figure 9A  Figure 9B  Figure 9C
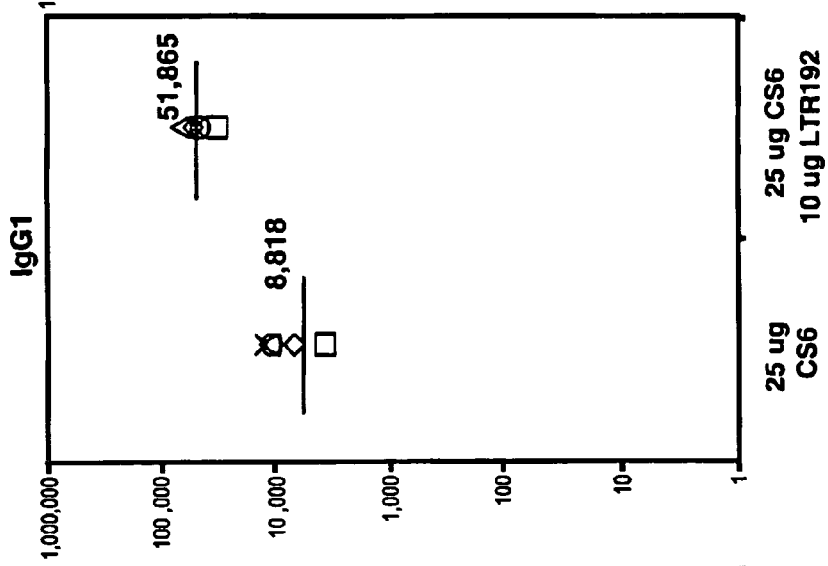
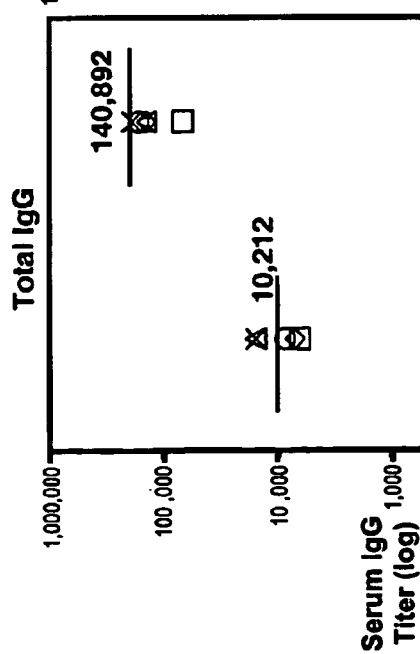

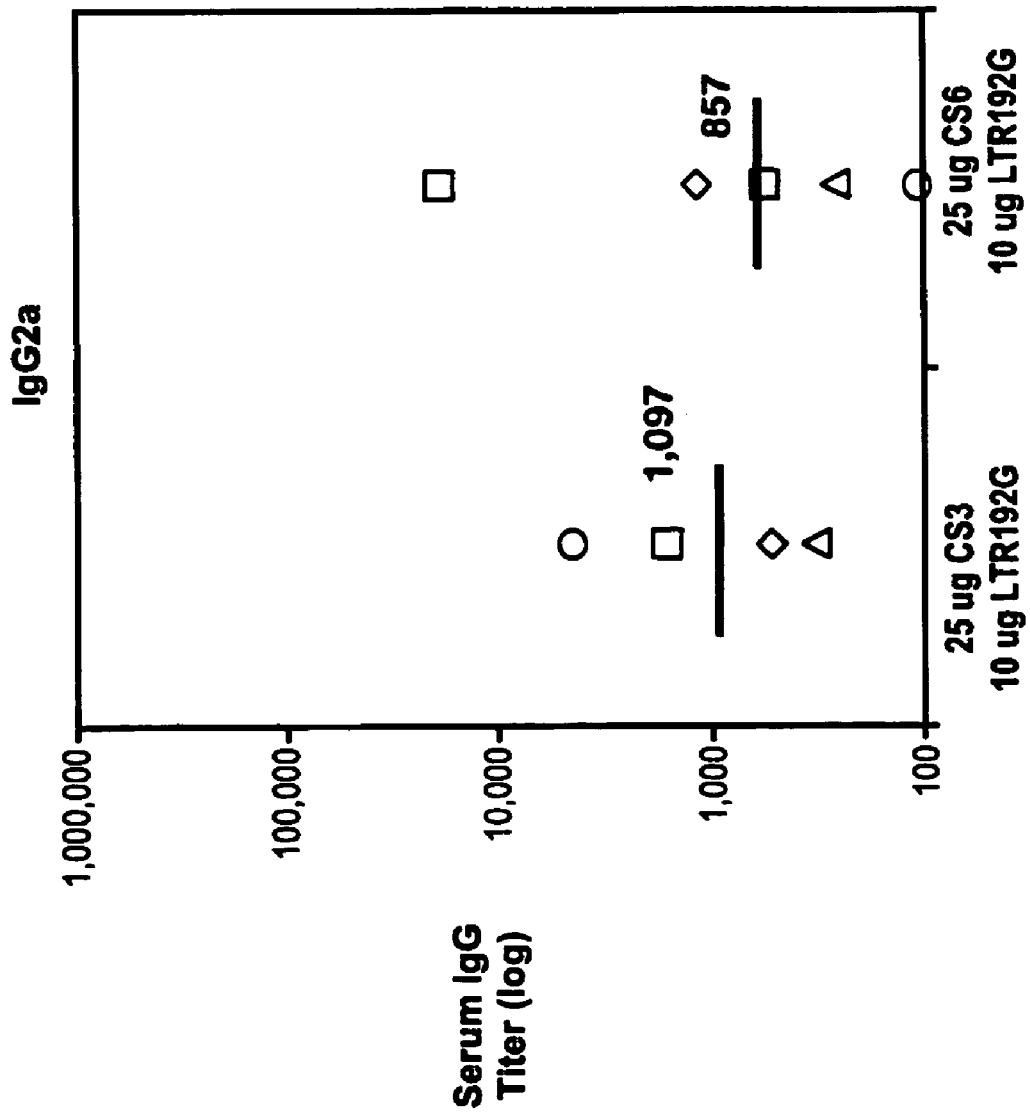

Vaccine dose PBS 10 ug mLT 25 ug CS3
10 ug mLT*

25 ug CS6
10 ug mLT

CFA1

CS3

CS6

CFA1

CS3

CS6

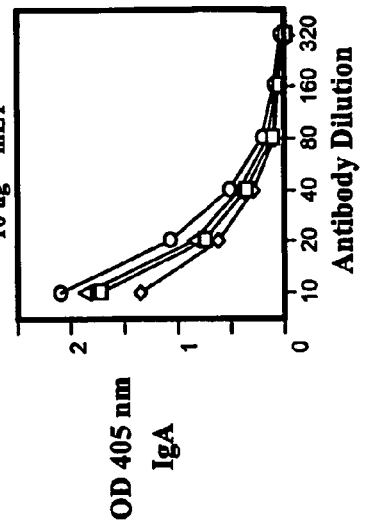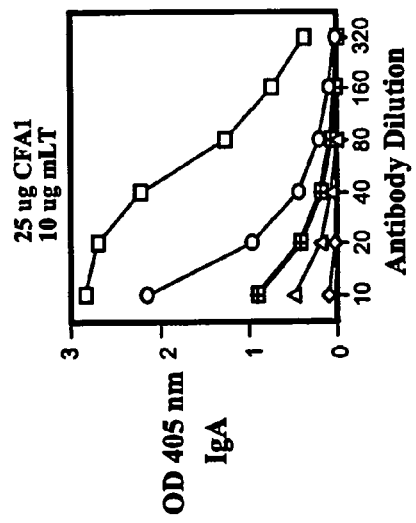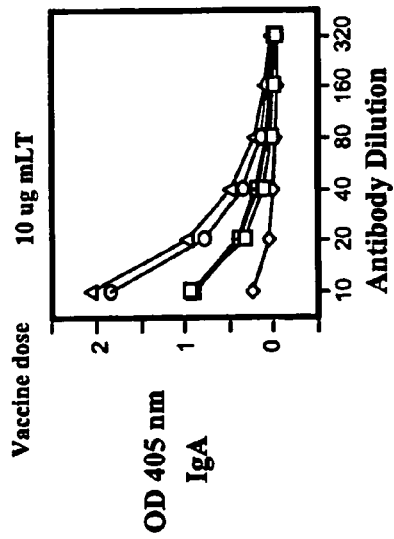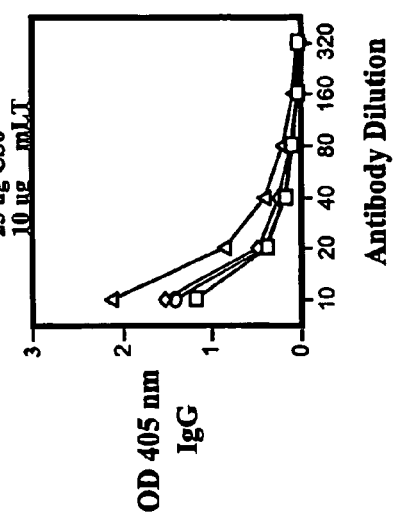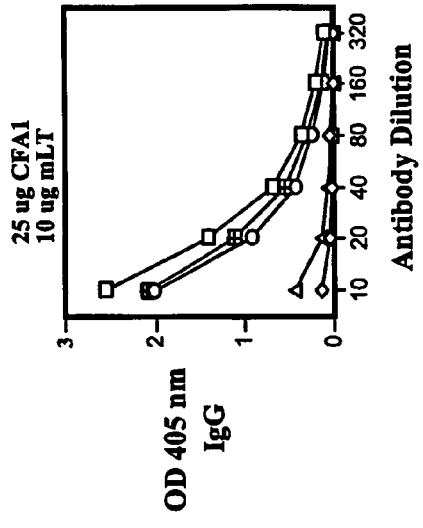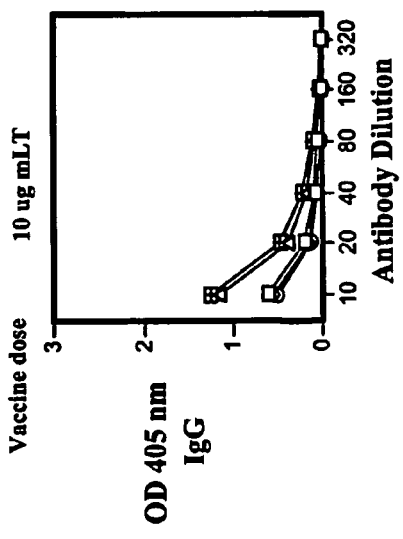
Figure 23A  Figure 23B  Figure 23C
Figure 23D  Figure 23E  Figure 23F

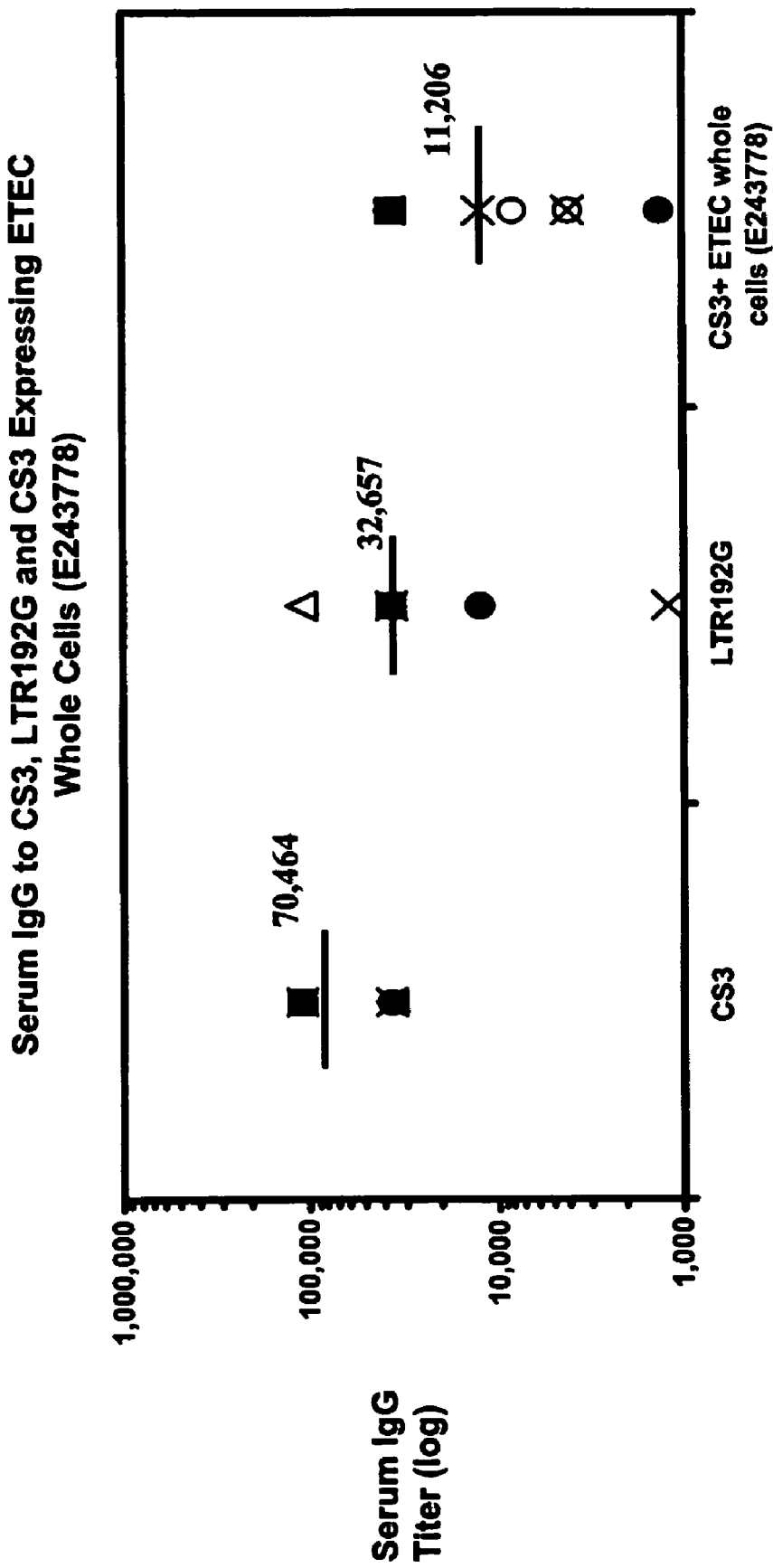

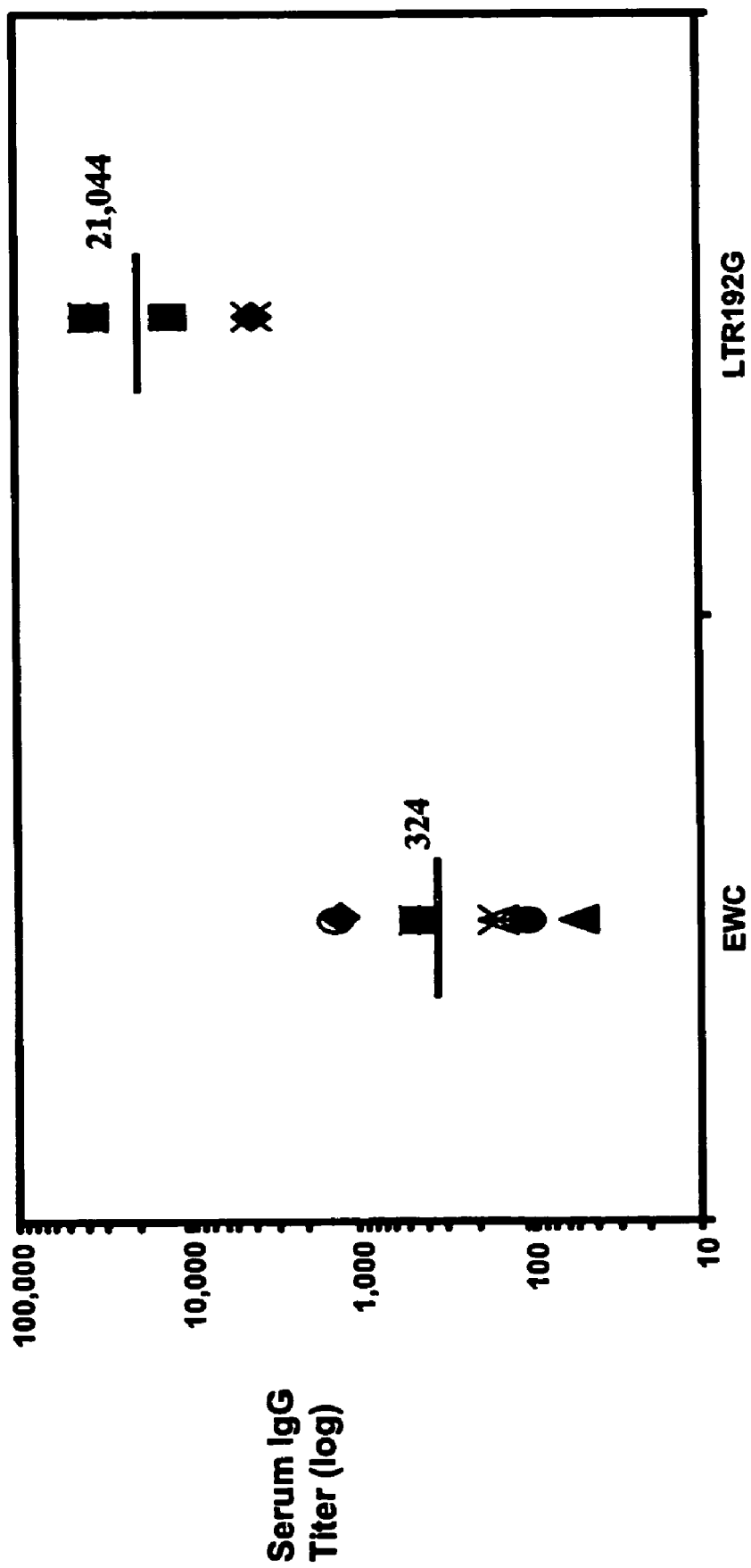

VACCINE FOR TRANSCUTANEOUS IMMUNIZATION

CROSS-REFERENCE TO RELATED APPLICATIONS

The present application is a U.S. National Phase Application of International Application No. PCT/US02/04254, filed Feb. 13, 2002, which claims the benefit of U.S. Provisional Application No. 60/268,016, filed Feb. 13, 2001; U.S. Provisional Application No. 60/304,110, filed Jul. 11, 2001; U.S. Provisional Application No. 60/310,447, filed Aug. 8, 2001; and U.S. Provisional Application No. 60/310,483, filed Aug. 8, 2001, all of which are herein incorporated by reference in their entirety.

STATEMENT REGARDING FEDERAL SPONSORSHIP

The U.S. federal government has certain rights in this invention as provided for under contracts MRMC/DAMD17-01-0085 and NIH/AI 45227-01.

FIELD OF THE INVENTION

The invention relates to vaccines and transcutaneous immunization to treat infections by pathogens such as, for example, enterotoxigenic *Escherichia coli* (ETEC) and/or other symptoms of diarrheal disease caused thereby.

BACKGROUND OF THE INVENTION

Skin, the largest human organ, plays an important part in the body's defense against invasion by infectious agents and contact with noxious substances. But this barrier function of the skin appears to have prevented the art from appreciating that transcutaneous immunization provided an effective alternative to enteral, mucosal, and parenteral administration of vaccines.

Anatomically, skin is composed of three layers: the epidermis, the dermis, and subcutaneous fat. Epidermis is composed of the basal, the spinous, the granular, and the cornified layers; the stratum corneum comprises the cornified layer and lipid. The principal antigen presenting cells of the skin, Langerhans cells, are reported to be in the mid- to upper-spinous layers of the epidermis in humans. Dermis contains primarily connective tissue. Blood and lymphatic vessels are confined to the dermis and subcutaneous fat.

The stratum corneum, a layer of dead skin cells and lipids, has traditionally been viewed as a barrier to the hostile world, excluding organisms and noxious substances from the viable cells below the stratum corneum. Stratum corneum also serves as a barrier to the loss of moisture from the skin: the relatively dry stratum corneum is reported to have 5% to 15% water content while deeper epidermal and dermal layers are relatively well hydrated with 85% to 90% water content. Only recently has the secondary protection provided by antigen presenting cells (e.g., Langerhans cells) been recognized. Moreover, the ability to immunize through the skin with or without penetration enhancement (i.e., transcutaneous immunization) using a skin-active adjuvant has only been recently described. Although undesirable skin reactions such as atopy and dermatitis were known in the art, recognition of the therapeutic advantages of transcutaneous immunization (TCI) might not have been appreciated in the past because the skin was believed to provide a barrier to the passage of molecules larger than about 500 daltons.

We have shown that a variety of adjuvants are effectively administered by TCI to elicit systemic and regional antigen-specific immune responses to a separate, co-administered antigen. See WO 98/20734, WO 99/43350, and WO 00/61184; U.S. Pat. Nos. 5,910,306 and 5,980,898; and U.S. patent application Ser. Nos. 09/257,188; 09/309,881; 09/311,720; 09/316,069; 09/337,746; and 09/545,417. For example, adjuvants like ADP-ribosylating exotoxins are safe and effective when applied epicutaneously, in contrast to the disadvantages associated with their use when administered by an enteral, mucosal, or parenteral route.

U.S. Pat. Nos. 4,220,584 and 4,285,931 use *E. coli* heat-labile enterotoxin to immunize against *E. coli*-induced diarrhea. Rabbits were intramuscularly injected with the immunogen and Freund's adjuvant. Protection against challenge with toxin and neutralization of toxic effects on ileal loop activity was shown. U.S. Pat. No. 5,182,109 describes combining vaccine and toxin (e.g., *E. coli* heat-labile toxin) and administration in injectable, spray, or oral form. Neutralization was demonstrated with colostrum of immunized cows. Mutant versions of enterotoxin have also been described to retain immunogenicity and eliminate toxicity (e.g., U.S. Pat. Nos. 4,761,372 and 5,308,835).

Novel and inventive vaccine formulations, as well as processes for making and using them, are disclosed herein. In particular, TCI and the advantages derived therefrom in human vaccination to treat diarrheal disease are demonstrated. An important showing is that competition among different antigens in a multivalent vaccine was not an obstacle when administered by transcutaneous immunization. Other advantages of the invention are discussed below or would be apparent from the disclosure herein.

SUMMARY OF THE INVENTION

Immunogens comprised of at least one adjuvant and/or one or more antigens capable of inducing an immune response against pathogens like enterotoxigenic *E. coli* (ETEC) are provided for immunization. The adjuvant may be an ADP-ribosylating exotoxin (e.g., *E. coli* heat-labile enterotoxin, cholera toxin, diphtheria toxin, pertussis toxin) or derivatives thereof having adjuvant activity; the antigen may be derived from a bacterial toxin (e.g., heat-labile or heat-stable enterotoxin) or a colonization or a virulence factor (e.g., CFA/I, CS1, CS2, CS3, CS4, CS5, CS6, CS17, PCF 0166) or peptide fragments or conjugates thereof having immunogenic activity. Subunit or whole-cell vaccines comprised of an immunogen and a patch are also provided, along with methods of making the aforementioned products and of using them for immunization. An immune response which is specific for molecules associated with pathogens (e.g., toxins, membrane proteins) may be induced by various routes (e.g., enteral, mucosal, parenteral, transcutaneous). Other traveler's diseases of interest that can be treated include campylobacteriosis (*Campylobacter jejuni*), giardiasis (*Giardia intestinalis*), hepatitis (hepatitis virus A or B), malaria (*Plasmodium falciparum, P. vivax, P. ovale,* and *P. malariae*), shigellosis (*Shigella boydii, S. dysenteriae, S. flexneri,* and *S. sonnei*), viral gastroenteritis (rotavirus), and combinations thereof. Effectiveness may be assessed by clinical or laboratory criteria. Protection may be assessed using surrogate markers or directly in controlled trials. Further aspects of the invention will be apparent to a person skilled in the art from the following detailed description and claims, and generalizations thereto.

DESCRIPTION OF THE DRAWINGS

FIG. 2A-2D. Kinetics of the anti-LT (A and B) and anti-CS6 (C and D) IgA and IgG antibody responses among volunteers immunized and boosted (arrows) using the transcutaneous route. The circles indicate the geometric mean titer by the day after the first immunization, the bars denote the corresponding 95% confidence intervals.

*$p<0.05$, $p<0.01$, *$p<0.001$, NS non-significant, Wilcoxon signed rank test, comparing antibody titer responses between boosting immunizations.

FIG. 3A-3D. Individual peak number of anti-LT (A and B) and anti-CS6 (C and D) ASC per 106 PBMC among responders to the immunization with adjuvant combined with antigen (LT+CS6), by the immunization after which the peak value was attained.

Figure 1A:
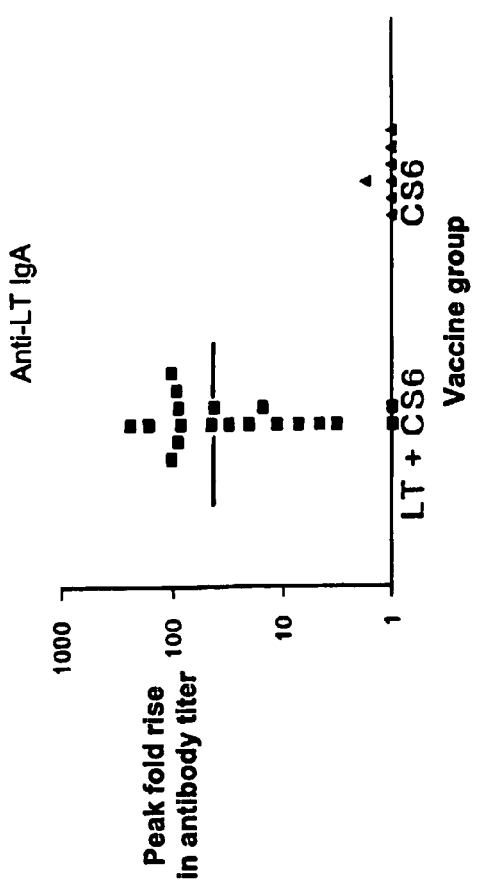
FIG. 1A-1D. Individual IgG and IgA peak fold rise in antibody titer to LT (A and B) and CS6 (C and D) among human volunteers immunized with adjuvant combined with antigen (LT+CS6), or with antigen alone (CS6). The transverse bar represents the median peak fold rise in antibody titer.
Figure 1C:
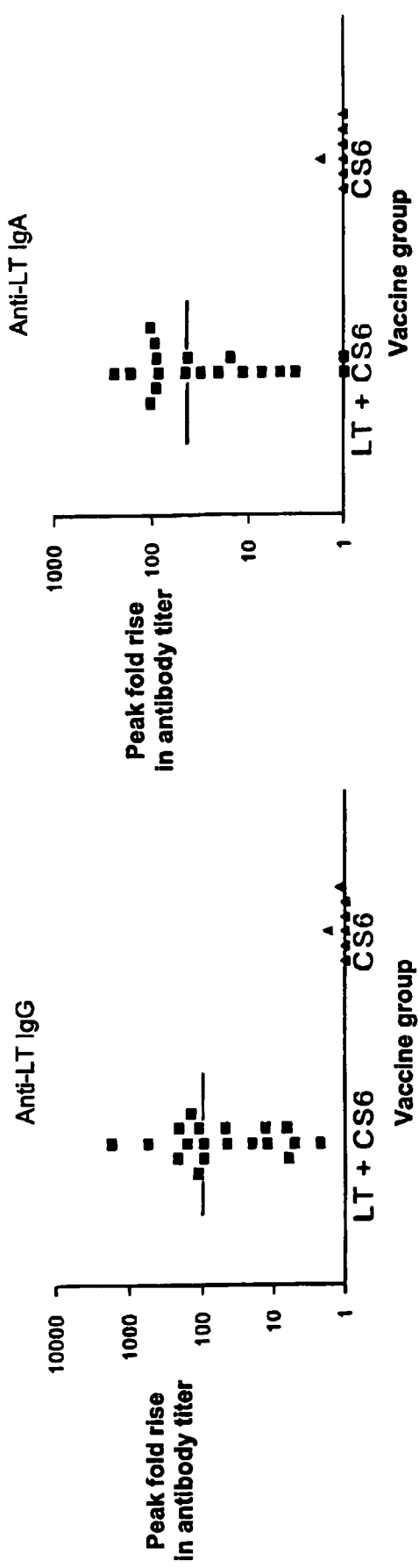
Figure 1B:
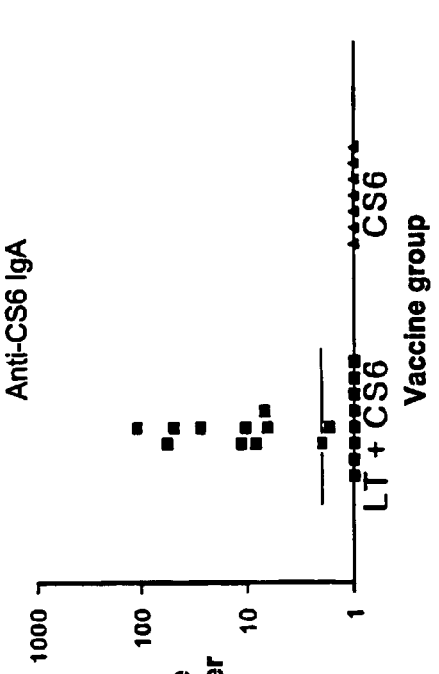
Figure 1D:
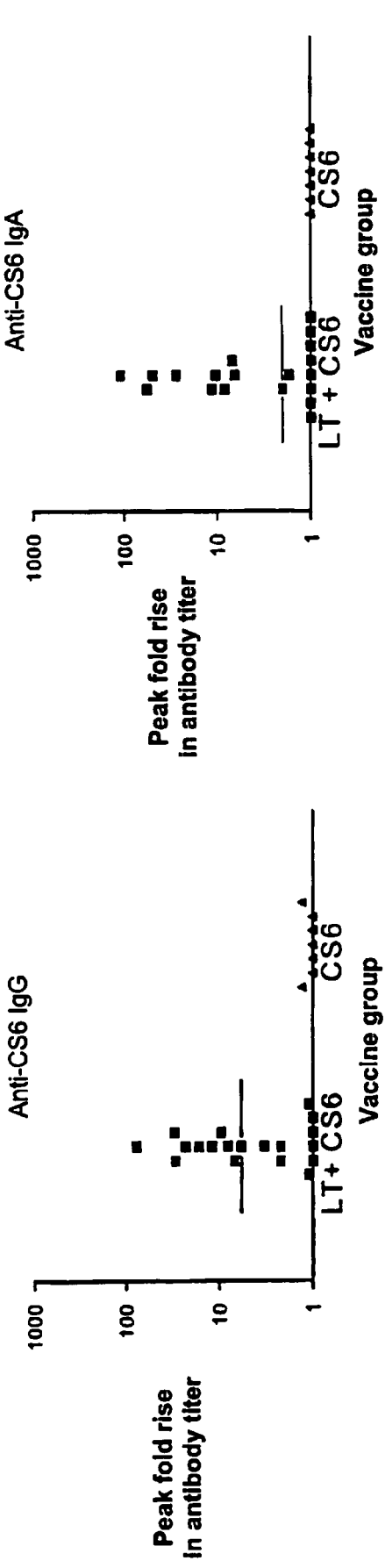
Figure 4B:
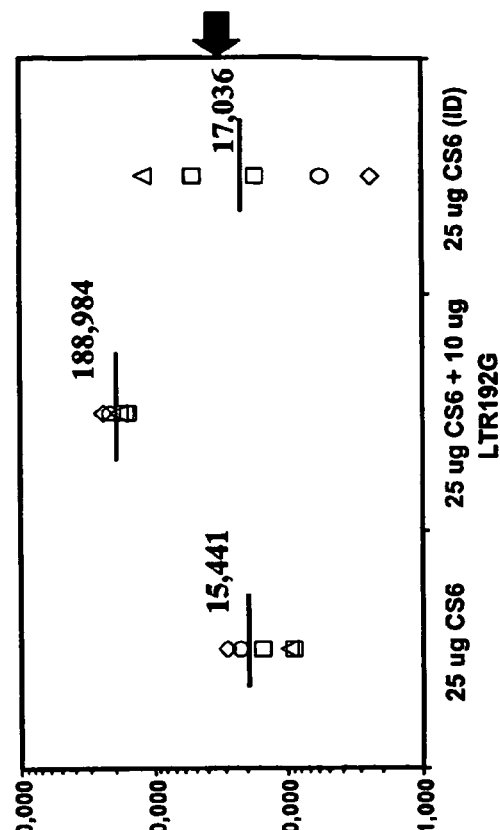
Figure 4A:
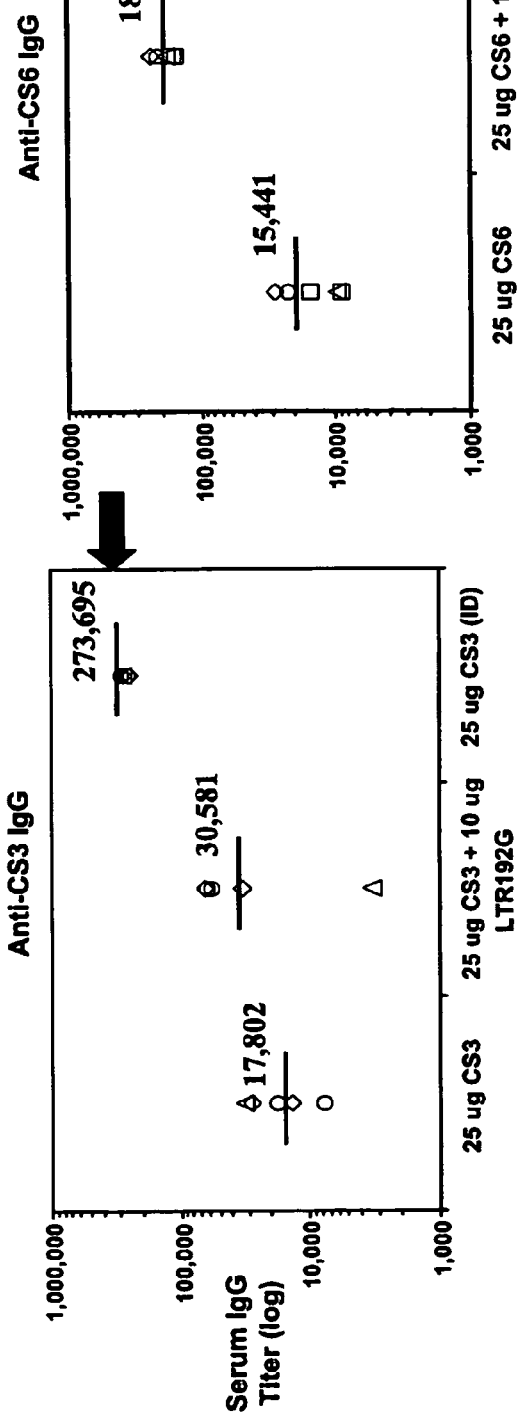
Figure 4C:
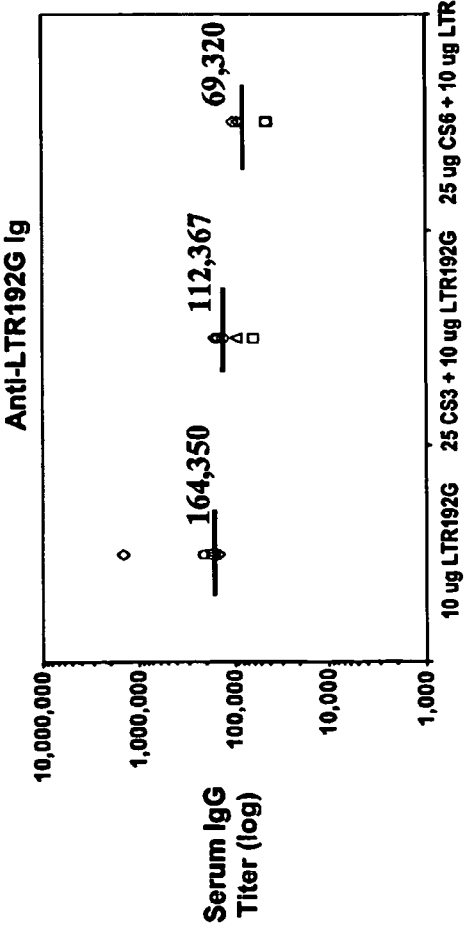

FIG. 4A-4C. Serum IgG response to TCI with CS3 and CS6 with and without LTR192G adjuvant. Mice were shaved on the dorsal caudal surface at the base of the tail 48 hr prior to vaccination. The shaved skin was pretreated by hydration with 10% glycerol and 70% isopropyl alcohol and tape stripped 10 times to disrupt the stratum corneum. Gauze patches were affixed to an adhesive backing and loaded with a 25 µl volume of 25 µg CS6 or 25 µg CS6 with 10 µg LTR192G. The patches were applied to the prepared skin and allowed to remain in place for ~18 hr. A group of mice was intradermally injected with a 25 µl of CS6(25 µg) at the base of the tail. All mice received a vaccination on day 0, 14 and 28. Serum samples were collected 14 days after the third vaccination (day 42). Panels show serum IgG titer to CS3 (A), serum IgG titer to CS6 (B), and serum IgG titer to LTR192G (C).

Figure 5A:
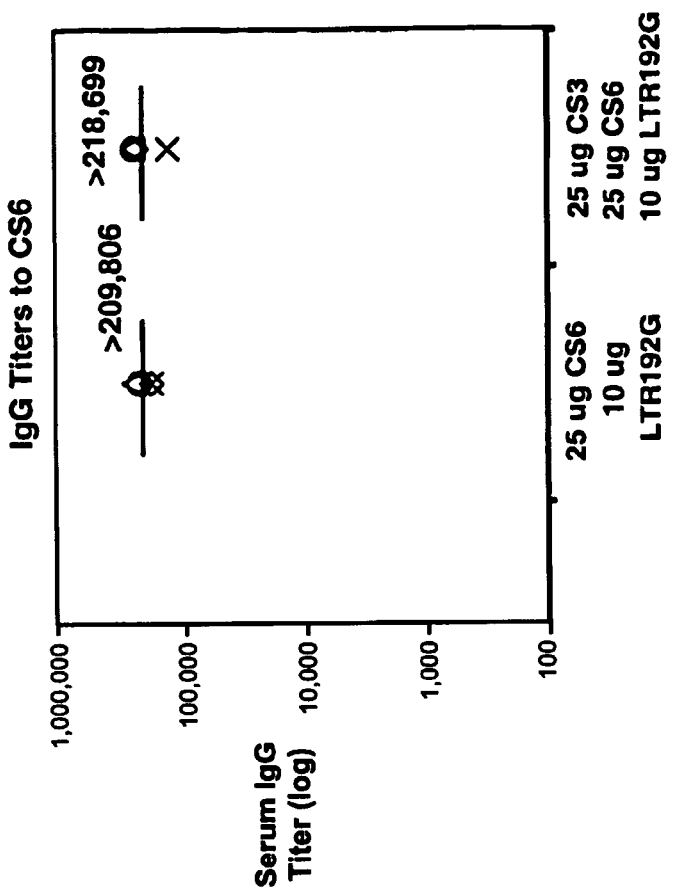
Figure 5B:
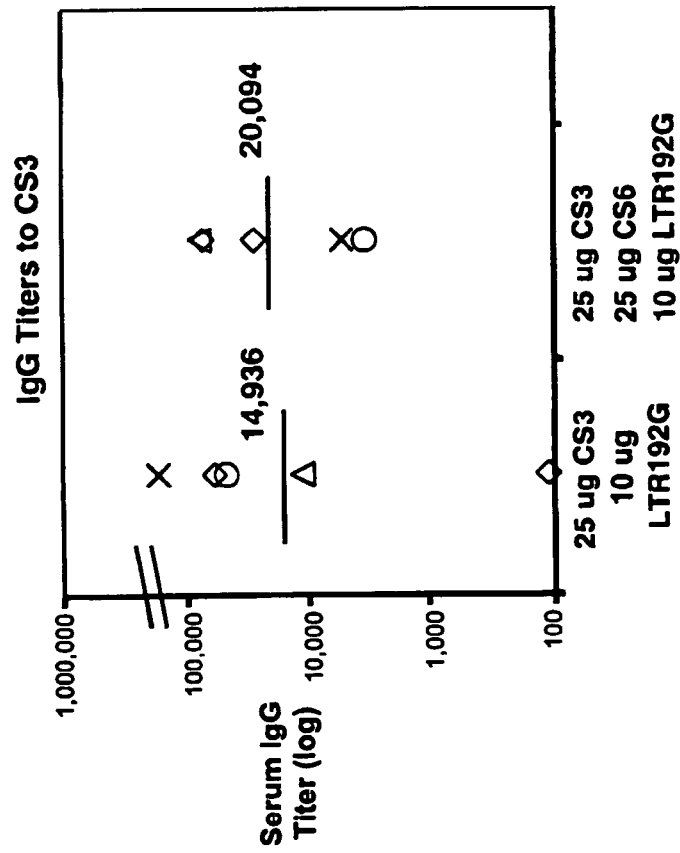

FIG. 5A-5B. Serum IgG response to TCI with divalent and trivalent ETEC subunit vaccines. The vaccination site at the base of the tail was prepared using the procedure described in FIG. 4. Gauze patches, affixed to an adhesive backing were loaded with 25 µl volume consisting of the following mixtures: 25 µg CS3 and 10 µg LTR192G; 25 µg CS3, 25 µg CS6 and 10 µg LTR192G. The patches were applied to the prepared skin and allowed to remain in place for ~18 hr. All mice received a transcutaneous vaccine on day 0 and 14. Serum was collected 10 days after the second immunization (day 24). Panels show serum IgG titer to CS3 (A) and serum IgG titer to CS6 (B).

Figure 6A:
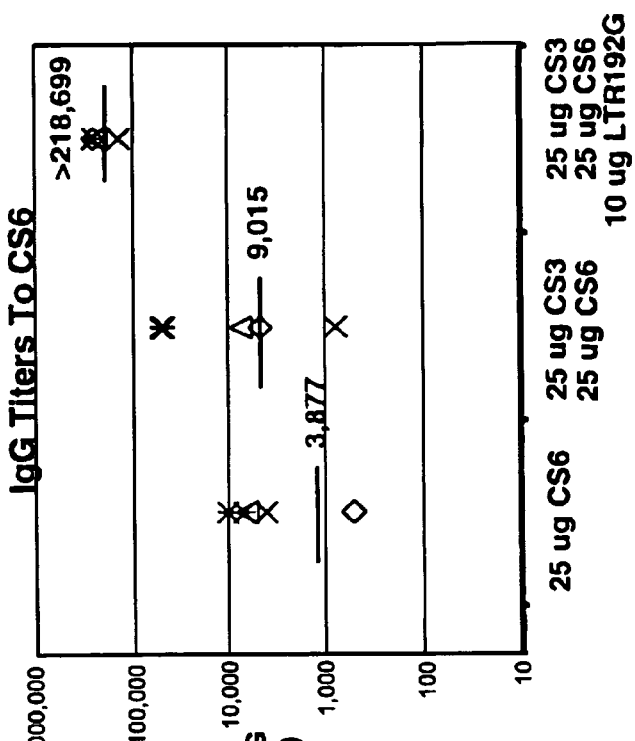
Figure 6B:
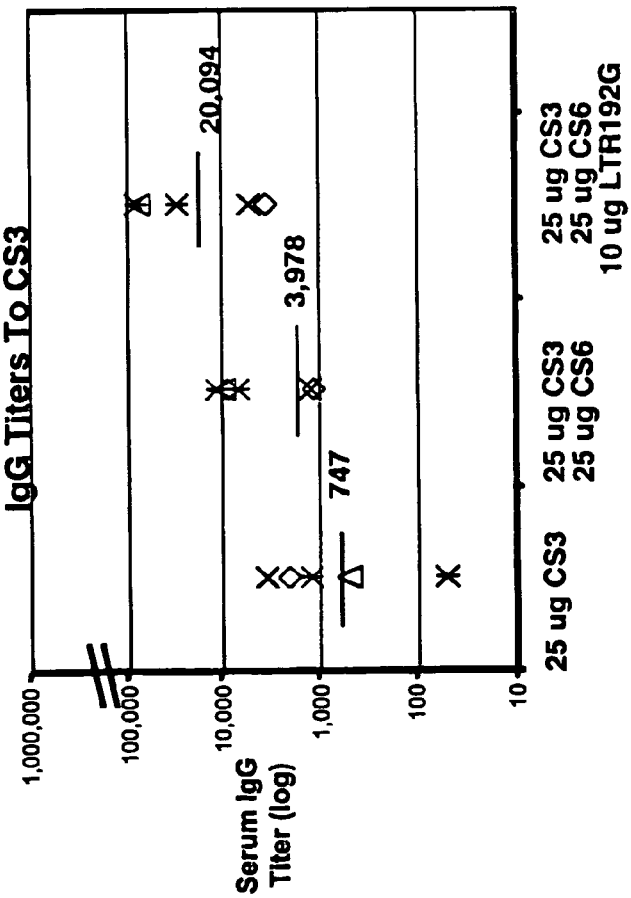

FIG. 6A-6B. Serum IgG response to TCI using a CS3, CS6 and LTR192G multivalent vaccines. The vaccination site at the base of the tail was prepared using the procedure described in FIG. 4. Gauze patches affixed to an adhesive backing were loaded with 25 µl volume consisting of the following mixtures: 25 µg CS3; 25 µg CS6; 25 µg each CS3 and CS6; 25 µg each CS3 and CS6 and 10 µg LTR192G. The patches were applied to the pretreated skin and allowed to remain in place for ~18 hr. All mice received two transcutaneous vaccinations on day 0 and 14. Serum was collected 10 days after the second immunization (day 24). Panels show serum IgG titer to CS3 (A) and serum IgG titer to CS6 (B).

Figure 7B:
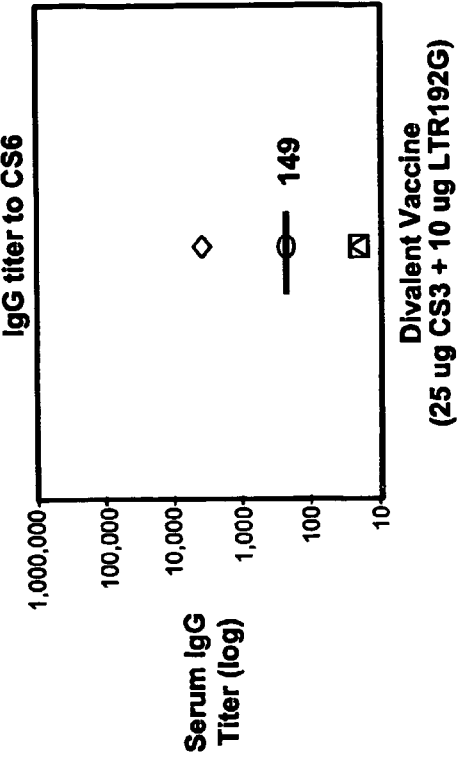
Figure 7D:
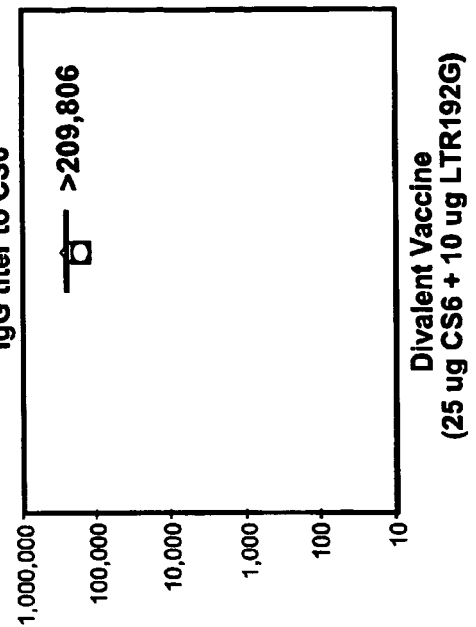
Figure 7A:
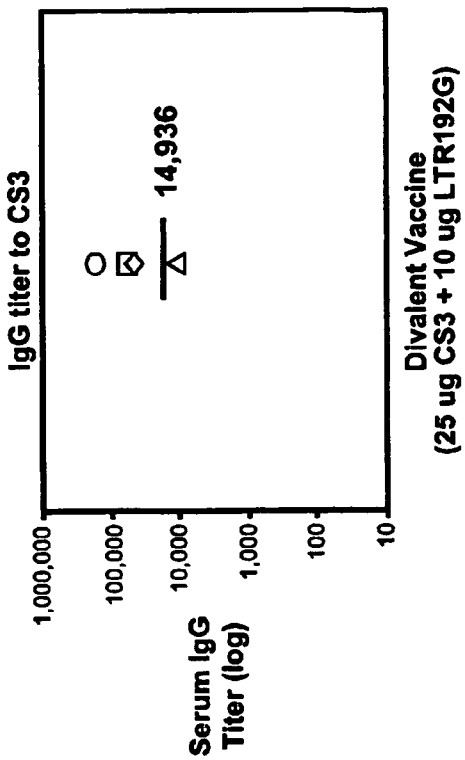
Figure 7C:
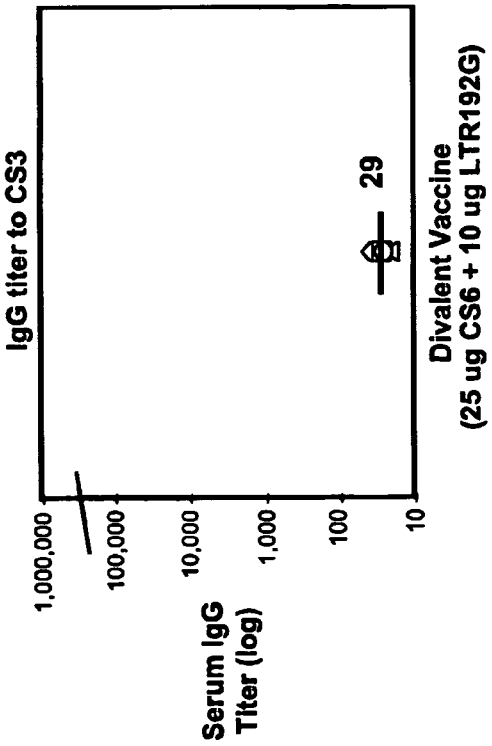

FIG. 7A-7B. Lack of antibody cross-reactivity between CS3 and CS6. The site at the base of the tail was prepared using the procedure described in FIG. 4. Gauze patches affixed to an adhesive backing were loaded with 25 µl volume consisting of the following mixtures: 25 µg CS3 with 10 µg LTR192G (panels A and B) and 25 µg CS6 with 10 µg LTR192G (panels C and D). The patches were applied overnight (~18 hr). All mice received two transcutaneous vaccinations on day 0 and 14. Serum was collected 10 days after the second immunization (day 24). Serum IgG titers for CS3 (panels A and C) and CS6 (panels B and D) were determined.

Figure 8A:
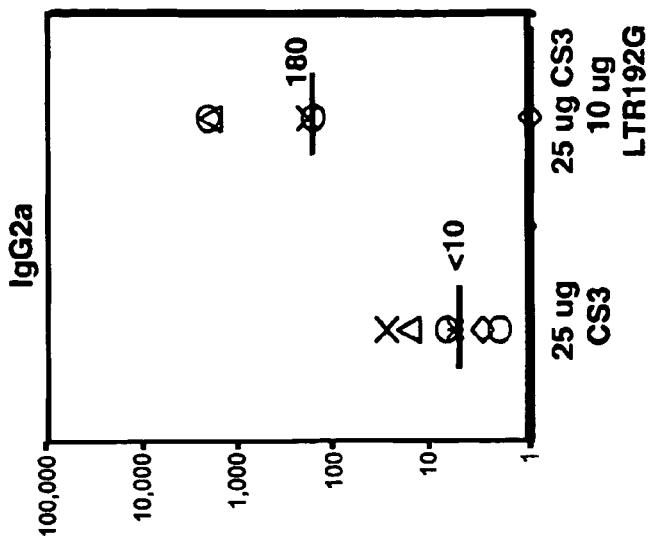
Figure 8B:
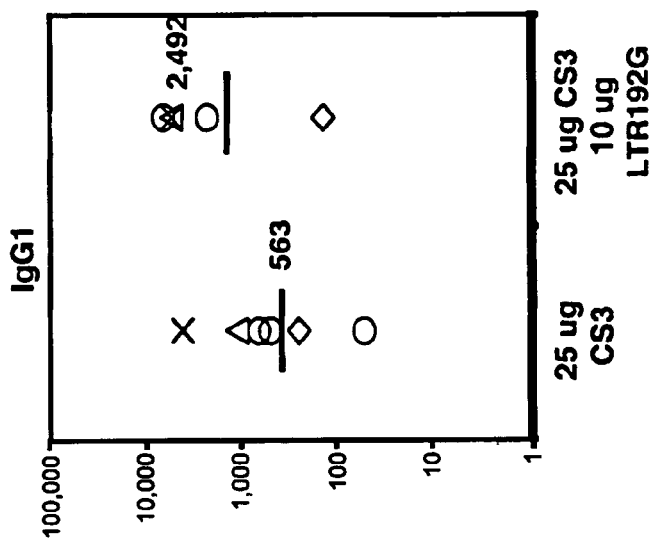
Figure 8C:
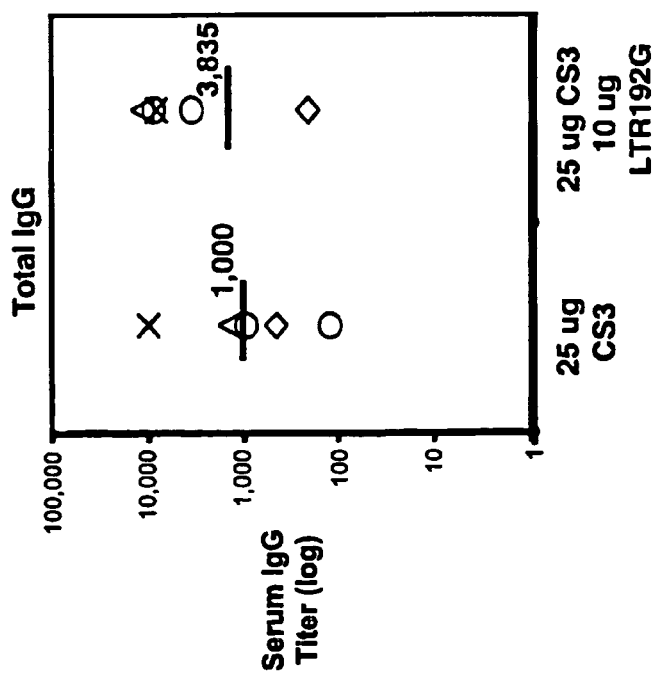

FIG. 8A-8C. Serum IgG subclasses elicited by transcutaneous vaccination with CS3 with and without LTR192G. Mice were shaved on the dorsal caudal surface at the base of the tail 48 hr prior to vaccination. The shaved skin was pretreated by hydration with 10% glycerol and 70% isopropyl alcohol. The hydrated skin was then mildly abraded with emery paper 10 times. Gauze patches were affixed to an adhesive backing and loaded with 25 µl of the following mixtures: 25 µg CS3 or 25 µg CS3 with or without 10 µg LTR192G. The patches were applied overnight (~18 hr). All mice received three transcutaneous vaccinations on day 0, 14 and 28. Serum samples were collected 30 days after the third vaccination (day 58). Panels show total serum IgG titers to CS3 (A), serum IgG1 subclass to CS3 (B), and serum IgG2a subclass to CS3 (C).

FIG. 9A-9C. Serum IgG subclasses elicited by TCI with CS6 with and without and LTR192G. Mice were shaved on the dorsal caudal surface at the base of the tail 48 hr prior to vaccination. The shaved skin was pretreated by hydration with 10% glycerol and 70% isopropyl alcohol. The hydrated skin was then mildly abraded with emery paper 10 times. Gauze patches were affixed to an adhesive backing and loaded with 25 µl of the following mixtures: 25 µg CS6 or 25 µg CS3 with or without 10 µg LTR192G. The patches were applied overnight (~18 hr). All mice received three transcutaneous vaccinations on day 0, 14, and 28. Serum samples were collected 30 days after the third vaccination (day 58). Panels show total serum IgG titers to CS6 (A), serum IgG1 subclass to CS6 (B), and serum IgG2a subclass to CS6 (C).

Figure 10C:
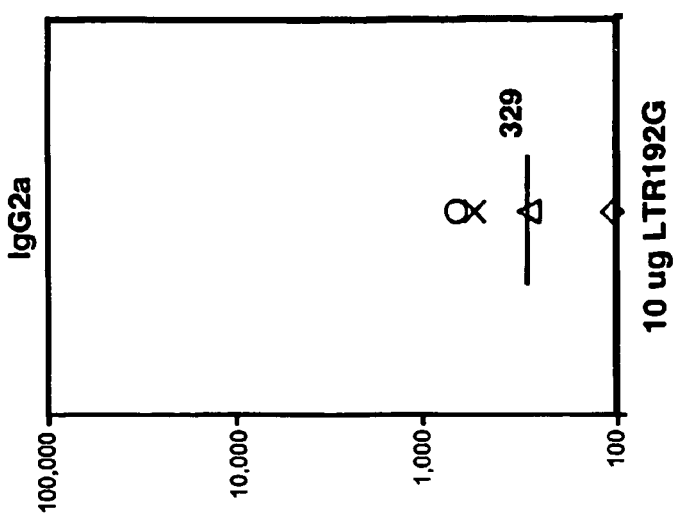
Figure 10B:
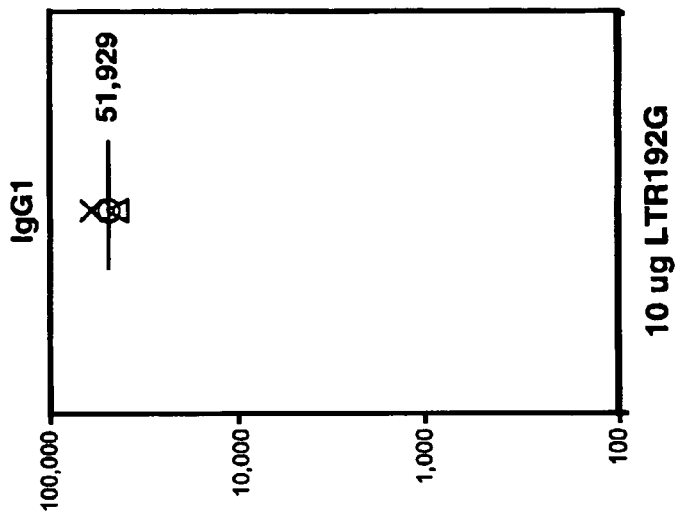
Figure 10A:
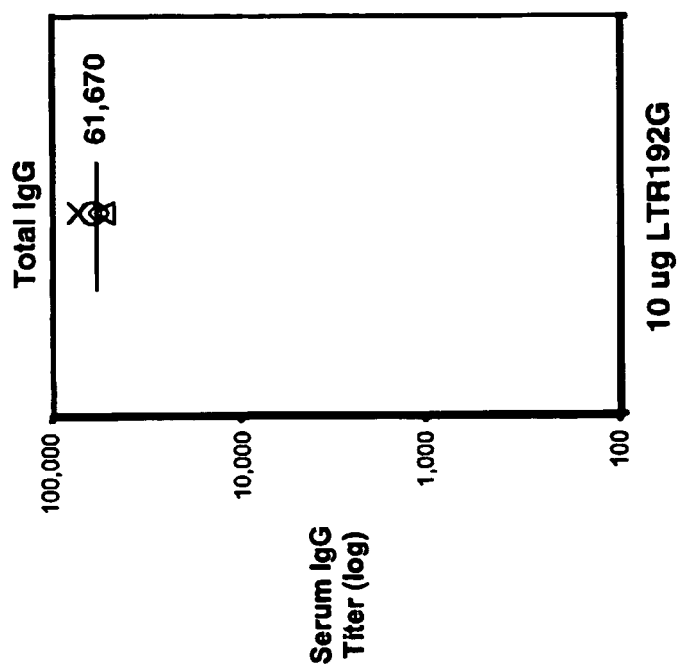

FIG. 10A-10C. Serum IgG subclasses elicited by TCI with LTR192G. Mice were shaved on the dorsal caudal surface at the base of the tail 48 hr prior to vaccination. The shaved skin was pretreated by hydration with 10% glycerol and 70% isopropyl alcohol. The hydrated skin was then mildly abraded with emery paper 10 times. Gauze patches were affixed to an adhesive backing and loaded with 25 µl of 10 µg LTR192G. The patches were applied overnight (~18 hr). All mice received three transcutaneous vaccinations on day 0, 14 and 28. Serum samples were collected 30 days after the third vaccination (day 58). Panels shown total serum IgG titers to LTR192G (A), serum IgG1 subclass to LTR192G (B), and serum IgG2a subclass to LTR192G (C).

Figure 11B:
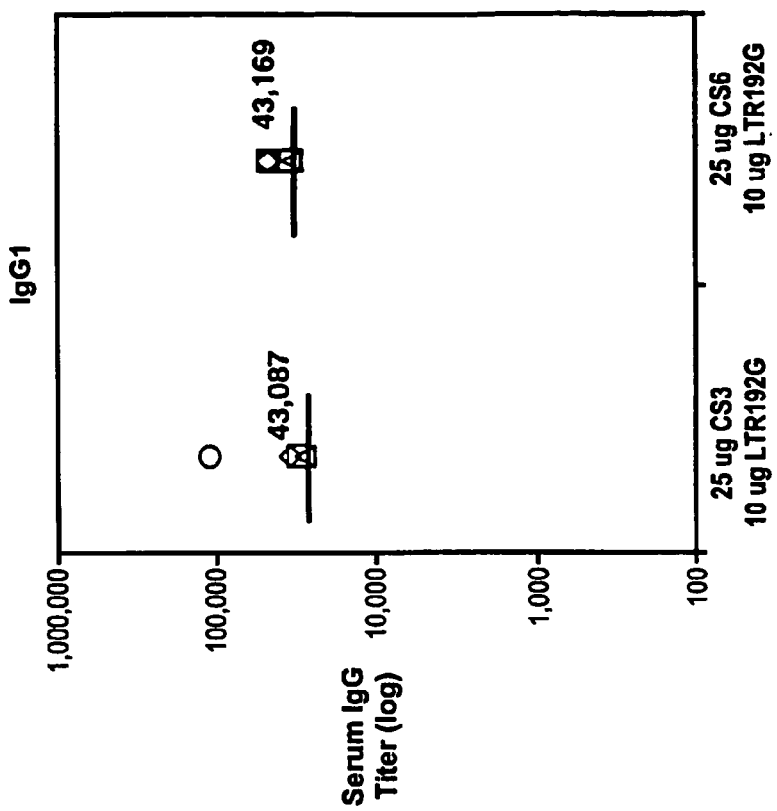
Figure 11A:
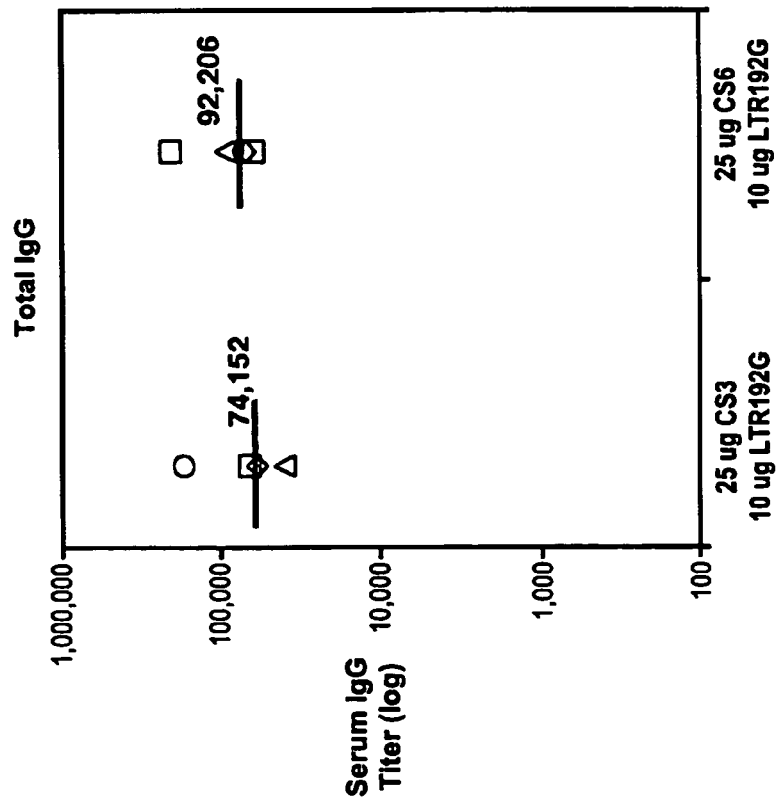

FIG. 11A-11C. Serum IgG subclasses elicited by LTR192G co-administered with CS3 or CS6. Mice were shaved on the dorsal caudal surface at the base of the tail 48 hr prior to vaccination. The shaved skin was pretreated by hydration with 10% glycerol and 70% isopropyl alcohol. The hydrated skin was then mildly abraded with emery paper 10 times. Gauze patches were affixed to an adhesive backing and loaded with 25 µl of the following: 25 µg CS3 with 10 µg LTR192G; and 25 µg CS6 with 10 µg LTR192G. The patches were applied overnight (~18 hr). All mice received three transcutaneous vaccinations on day 0, 14 and 28. Serum samples were collected 30 days after the third vaccination (day 58). Panels show total serum IgG titers to LTR192G (A), serum IgG1 subclass to LTR192G (B), and serum IgG2a subclass to LTR192G (C).

FIG. 12A-12H. Detection of CS3 specific fecal IgA (upper panels) and IgG (lower panels) following TCI. Mice were shaved on the dorsal caudal surface at the base of the tail 48 hr prior to vaccination. The shaved skin was pretreated by hydration with 10% glycerol and 70% isopropyl alcohol. The hydrated skin was then tape stripped 10 times. Gauze patches were affixed to an adhesive backing and loaded with 25 μl of the following mixtures: phosphate buffered saline (panels A and E); 25 μg CS3 (panels B and F); and 25 μg CS3 with 10 μg LTR192G (panels C and G). The patches were applied overnight (~18 hr). A group of mice was vaccinated by intradermal (ID) injection of 25 μg CS3 (panels D and H). All mice received three vaccinations on day 0, 14 and 28. Fecal samples were collected one week after the third immunization (day 35). The samples were processed and evaluated for fecal IgA (panels A-D) and IgG (panels E-H) against CS3.

FIG. 13A-13H. Detection of CS6 specific fecal IgA (upper panels) and IgG (lower panels) following TCI. Mice were shaved on the dorsal caudal surface at the base of the tail 48 hr prior to vaccination. The shaved skin was pretreated by hydration with 10% glycerol and 70% isopropyl alcohol. The hydrated skin was then tape stripped 10 times. Gauze patches were affixed to an adhesive backing and loaded with 25 μl of the following mixtures: phosphate buffered saline (panels A and E); 25 μg CS6 (panels B and F); and 25 μg CS6 with 10 μg LTR192G (panels C and G). The patches were applied overnight (~18 hr). A group of mice was vaccinated by intradermal (ID) injection of 25 μg CS6 (panels D and H). All mice received three vaccinations on day 0, 14 and 28. Fecal samples were collected one week after the third immunization (day 35). The samples were processed and evaluated for fecal IgA (panels A-D) and IgG (panels E-H) against CS6.

FIG. 14A-14H. Detection of LTR192G specific fecal IgA (upper panels) and IgG (lower panels) following TCI. Mice were shaved on the dorsal caudal surface at the base of the tail 48 hr prior to vaccination. The shaved skin was pretreated by hydration with 10% glycerol and 70% isopropyl alcohol. The hydrated skin was then tape stripped 10 times. Gauze patches were affixed to an adhesive backing and loaded with 25 μl of the following mixtures: phosphate buffered saline (panels A and E); 10 μg LTR192G (panels B and F); and 25 μg CS3 with 10 μg LTR192G (panels C and G); and 25 μg CS6 and 10 μg LTR192G (panel D and H). The patches were applied overnight (~18 hr). All mice received three vaccinations on day 0, 14 and 28. Fecal samples were collected one week after the third immunization (day 35). The samples were processed and evaluated for fecal IgA (panels A-D) and IgG (panels E-H) against LTR192G.

FIG. 15A-15D. Detection of CS3, CS6 and LTR192G specific antibody secreting cells (ASC) in the spleen of mice transcutaneously vaccinated with monovalent and divalent ETEC subunit vaccines. Mice were shaved on the dorsal caudal surface at the base of the tail 48 hr prior to vaccination. The shaved skin was pretreated by hydration with 10% glycerol and 70% isopropyl alcohol. The hydrated skin was then tape stripped 10 times. Gauze patches were affixed to an adhesive backing and loaded with 25 μl of the following mixtures: phosphate buffered saline (vehicle); 25 μg CS3; 25 μg CS6; 25 μg CS3 with 10 μg LTR192G; and 25 μg CS6 with 10 μg LTR192G. The patches were applied overnight (~18 hr). In addition, groups of mice were vaccinated by intradermal (ID) injection at the base of the tail with 25 μg of CS3 or CS6. All mice were vaccinated three times on day 0, 14 and 28. The spleen was harvested 30 days after the third immunization (day 58). Panels show CS3-specific IgA-ASC (A) and IgG-ASC (B); CS6-specific IgA-ASC (C) and IgG-ASC (D), and LTR192G-specific IgA-ASC (A and C) and IgG-ASC (B and D).

Figure 16A:
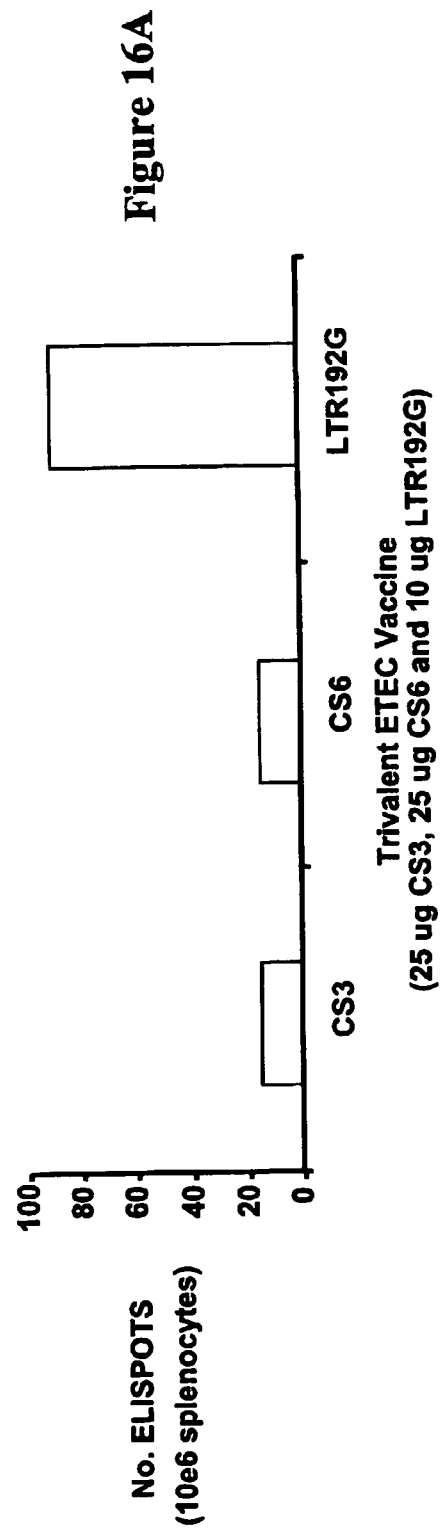
Figure 16B:
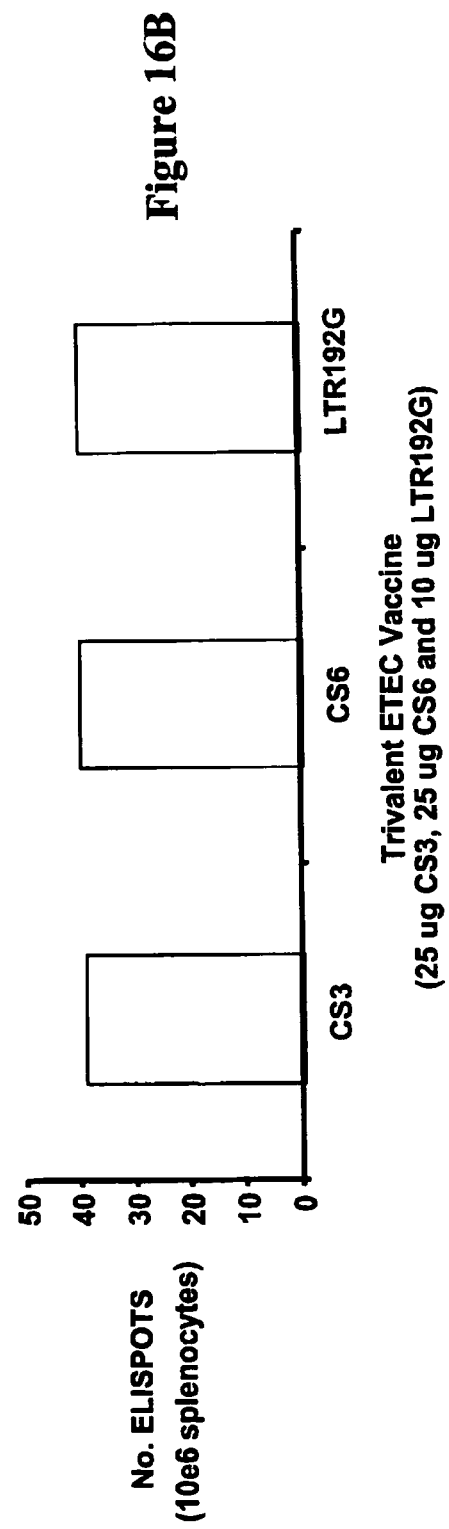

FIG. 16A-16B. Detection of CS3, CS6 and LTR192G specific antibody secreting cells (ASC) in the spleen of mice transcutaneously vaccinated with trivalent ETEC subunit vaccine. Mice were shaved on the dorsal caudal surface at the base of the tail 48 hr prior to vaccination. The shaved skin was pretreated by hydration with 10% glycerol and 70% isopropyl alcohol. The hydrated skin was then tape stripped 10 times. Gauze patches were affixed to an adhesive backing and loaded with 25 μl of a mixture of the following formulation: phosphate buffered saline (vehicle); 25 μg CS3; 25 μg CS6; 25 μg CS3 with 10 μg LTR192G; 25 μg CS3/25 g CS6/10 μg LTR192G. The patches were applied overnight (~18 hr). Mice were vaccinated three times on day 0, 14 and 28. The spleen was harvested 30 days after the third immunization (day 58). Panels show IgA-ASC specific for CS3, CS6 and LTR192G (A) and IgG-ASC specific for CS3, CS6 and LTR192G (B).

Figure 17A:
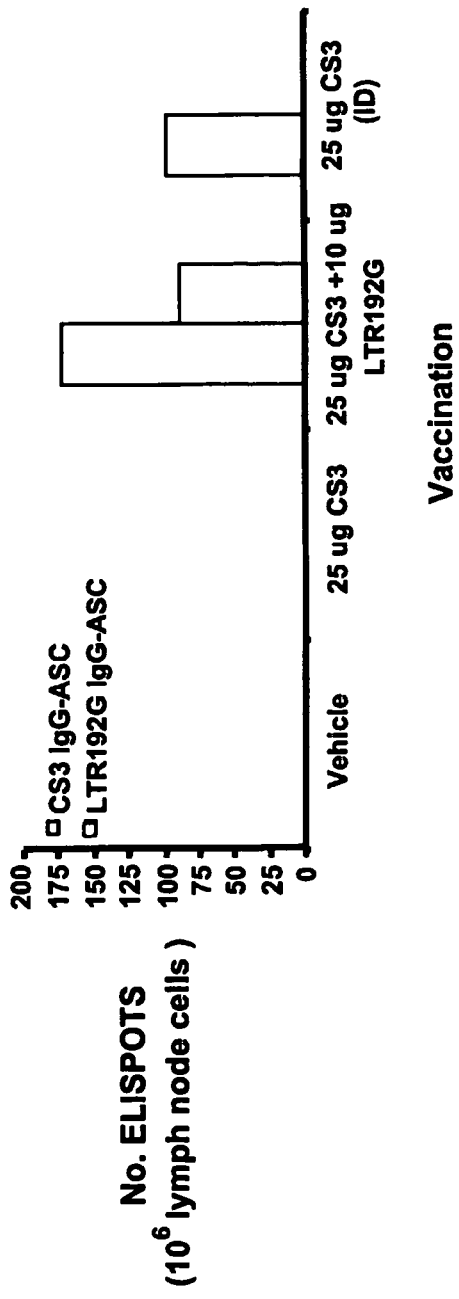
Figure 17B:
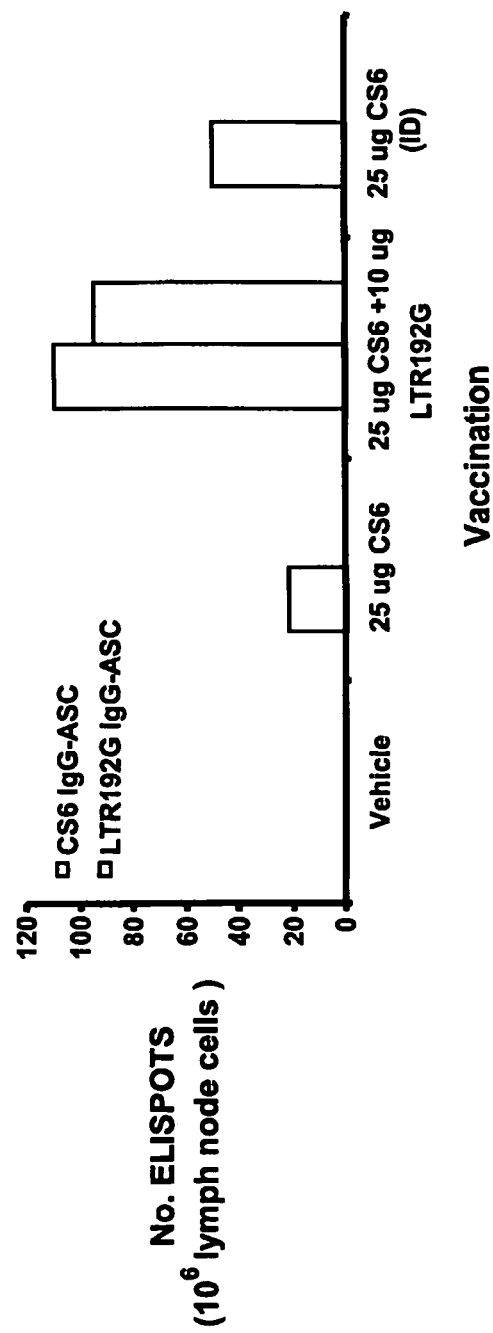

FIG. 17A-17B. Detection of CS3, CS6 and LTR192G specific antibody secreting cells (ASC) in the inguinal lymph nodes of mice transcutaneously vaccinated with monovalent and divalent ETEC subunit vaccines. Mice were shaved on the dorsal caudal surface at the base of the tail 48 hr prior to vaccination. The shaved skin was pretreated by hydration with 10% glycerol and 70% isopropyl alcohol. The hydrated skin was then tape stripped 10 times. Gauze patches were affixed to an adhesive backing and loaded with 25 μl of the following mixtures: phosphate buffered saline (vehicle); 25 μg CS3; 25 μg CS6; 25 μg CS3 with 10 μg LTR192G; and 25 μg CS6 with 10 μg LTR192G. The patches were applied overnight (~18 hr). In addition, separate groups of mice were vaccinated by intradermal (ID) injection at the base of the tail with 25 μg of CS3 or CS6. All mice were vaccinated three times on day 0, 14 and 28. Inguinal lymph nodes were collected 30 days after the third immunization (day 58). Panels show CS3-specific IgG-ASC (A), CS6-specific IgG-ASC (B), and LTR192G-specific IgG-ASC (A and B).

Figure 18:
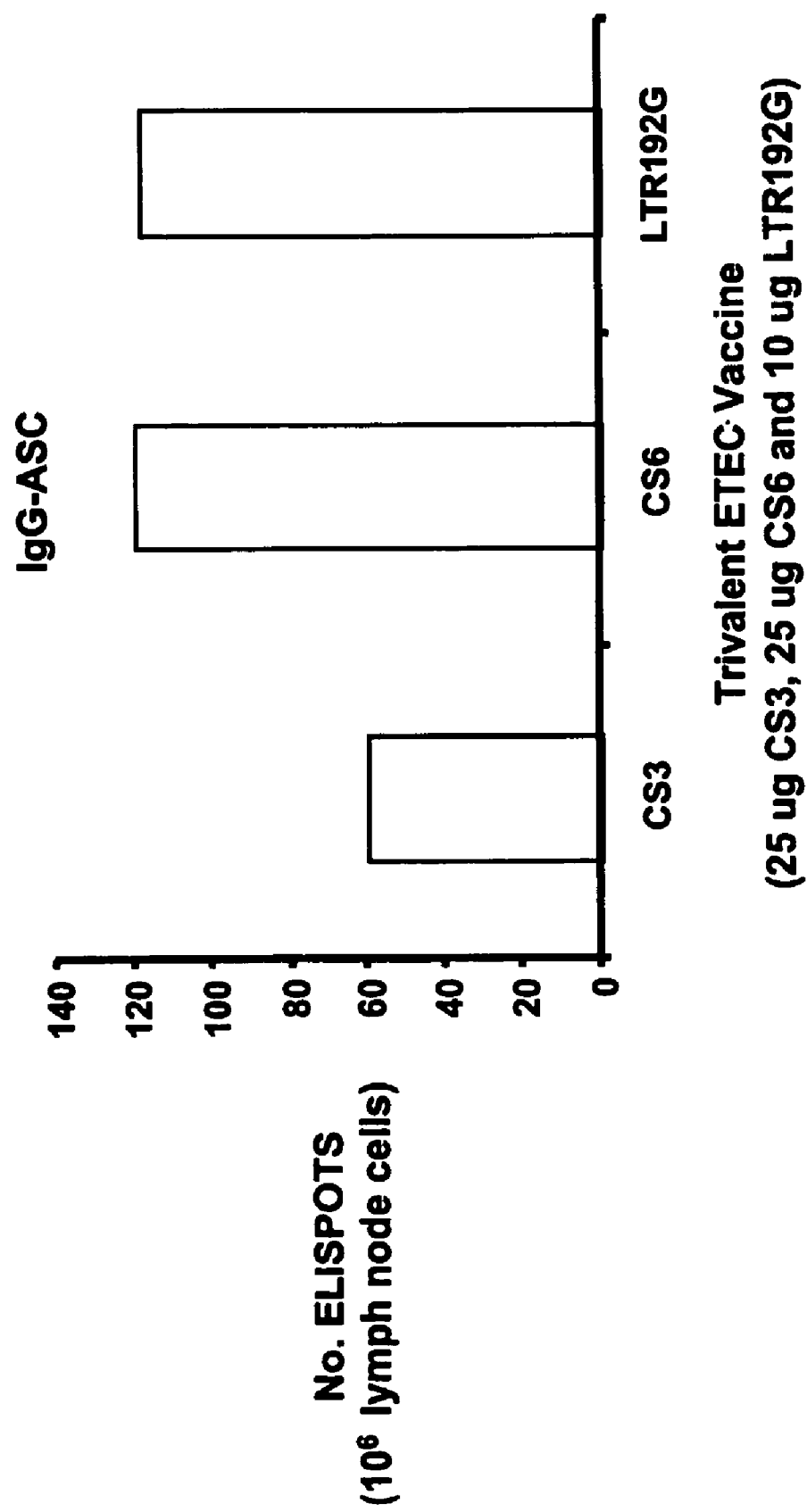

FIG. 18. Detection of CS3, CS6 and LTR192G specific antibody secreting cells (IgG-ASC) in the inguinal lymph nodes of mice transcutaneously vaccinated with trivalent ETEC subunit vaccine. Mice were shaved on the dorsal caudal surface at the base of the tail 48 hr prior to vaccination. The shaved skin was pretreated by hydration with 10% glycerol and 70% isopropyl alcohol. The hydrated skin was then tape stripped 10 times. Gauze patches were affixed to an adhesive backing and loaded with 25 μl of a mixture consisting of 25 μg CS3, 25 μg CS6 and 10 μg LTR192G. The patches were applied overnight (~18 hr). All mice were vaccinated three times on day 0, 14 and 28. Inguinal lymph nodes were collected 30 days after the third immunization (day 58).

Figure 19A:
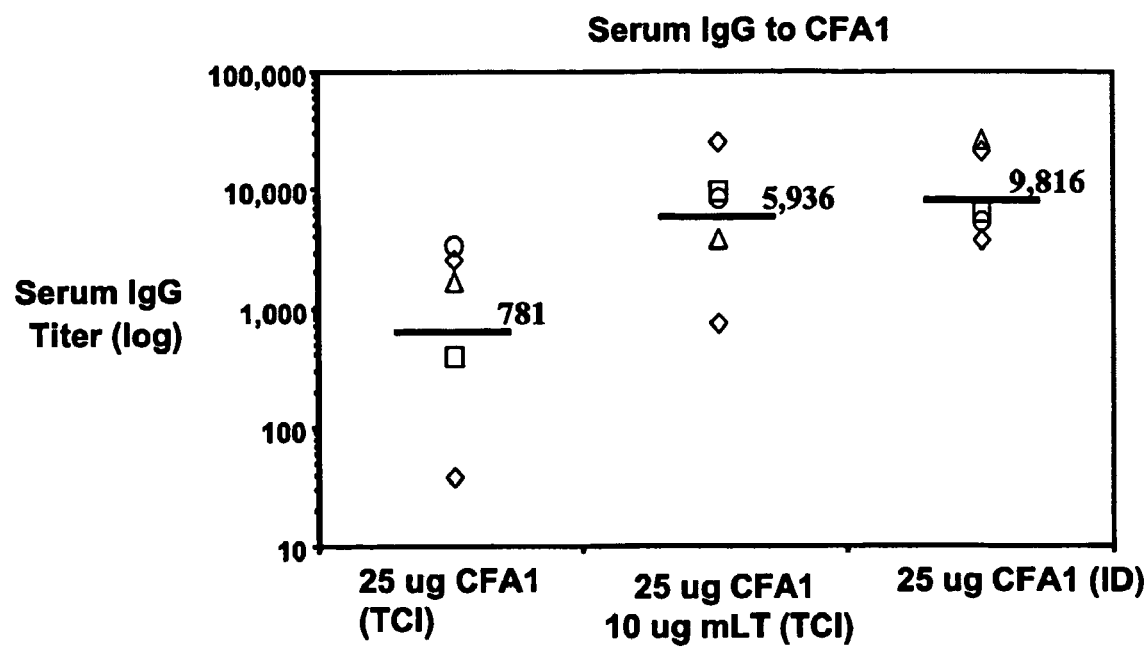
Figure 19B:
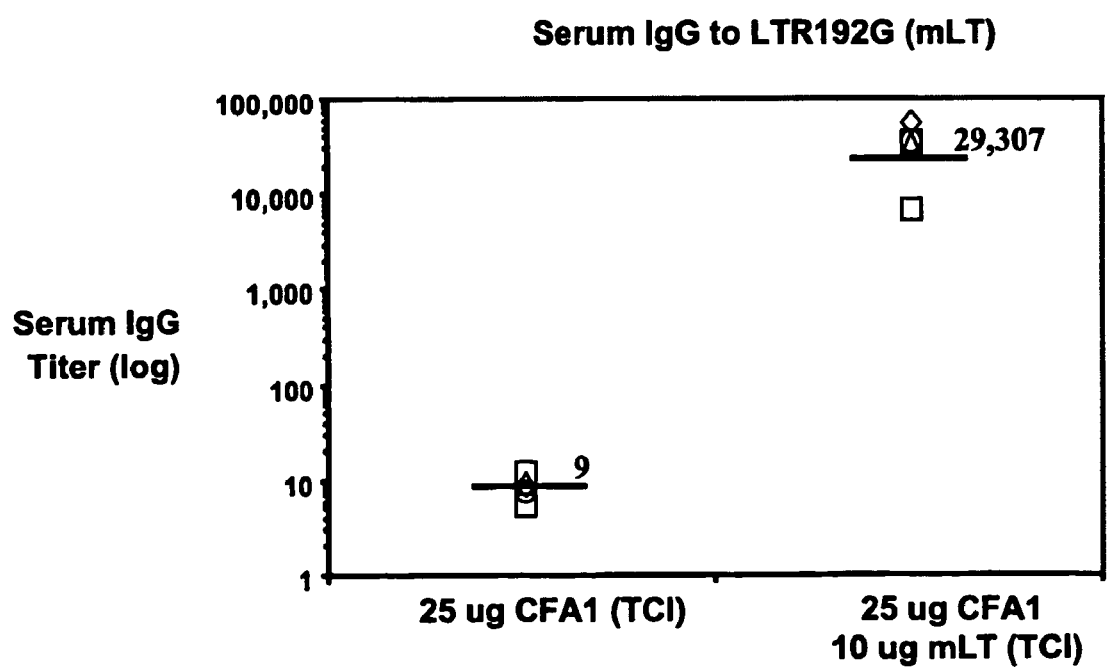
Figure 20A:
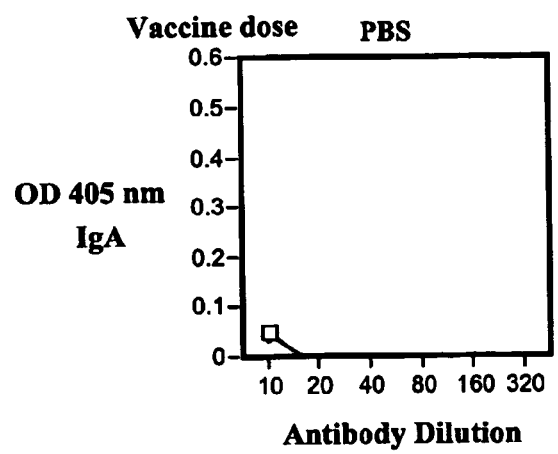
Figure 20B:
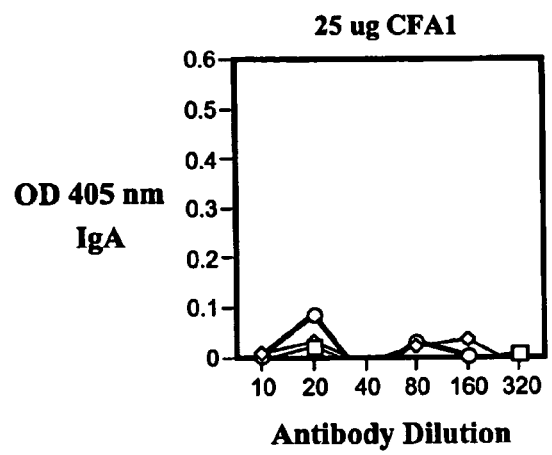
Figure 20C:
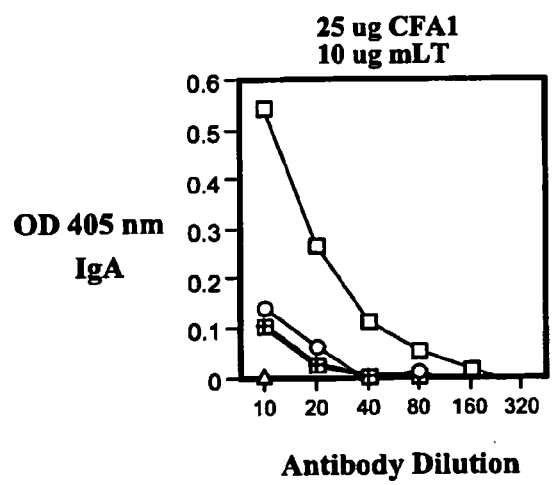
Figure 20D:
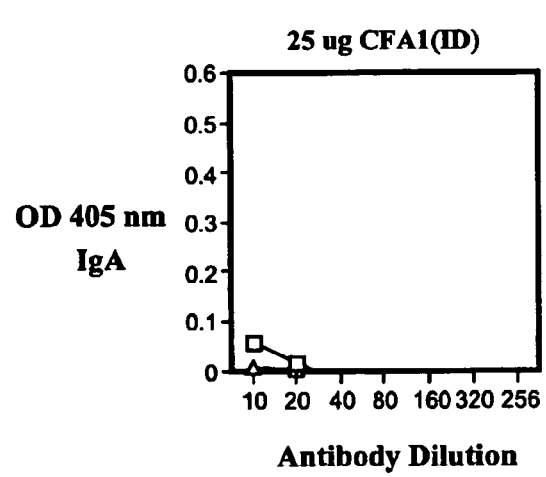
Figure 20E:
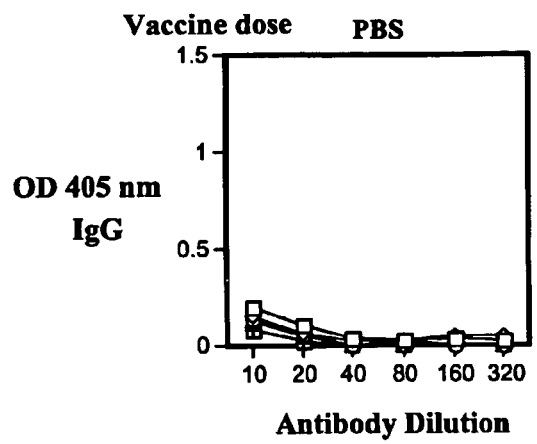
Figure 20F:
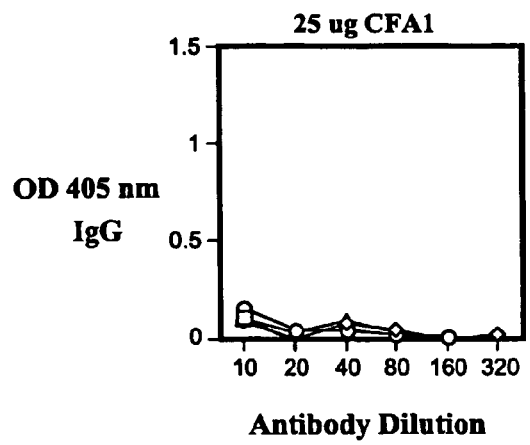
Figure 20G:
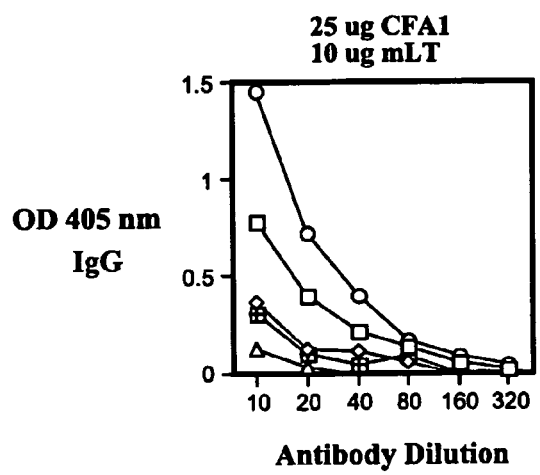
Figure 20H:
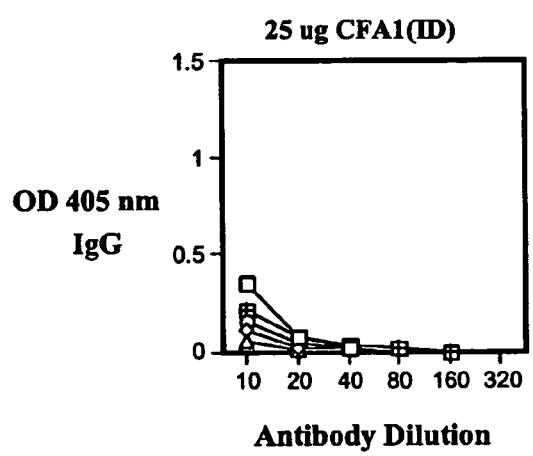

FIG. 19A-19B. Serum IgG response to TCI with CFA/I with and without LTR192G adjuvant. Mice were shaved on the dorsal caudal surface at the base of the tail 48 hr prior to vaccination. The shaved skin was pretreated by hydration with 10% glycerol and 70% isopropyl alcohol and mildly abraded with emery paper 5 times to disrupt the stratum corneum. Gauze patches were affixed to an adhesive backing and loaded with a 25 μl volume of 25 μg CFA/I and 25 μg CFA/I with 10 μg LTR192G. The patches were applied to the prepared skin and allowed to remain in place for ~18 hr. Separate groups of mice was intradermally injected with a 25 μl of CFA/I (25 μg) at the base of the tail. All mice received a vaccination on day 0 and 14. Serum samples were collected 10 days after the second vaccination (day 24). Panels show serum IgG titer to CFA/I (A) and serum IgG titer to LTR192G (B).

FIG. 20A-20H. Detection of CFA/I specific fecal IgA (upper panels) and IgG (lower panels) following TCI. Mice were shaved on the dorsal caudal surface at the base of the tail 48 hr prior to vaccination. The shaved skin was pretreated by hydration with 10% glycerol and 70% isopropyl alcohol. The hydrated skin was then mildly abraded with emery paper 5 times. Gauze patches were affixed to an adhesive backing and loaded with 25 µl volume of 25 µg of the following mixtures: phosphate buffered saline (panels A and E); 25 of the following mixtures: phosphate buffered saline (Panels A and E); 25 µg CFA/I (panels B and F); and 25 µg CFA/I with 10 µg LTR192G (panels C and G). The patches were applied overnight (~18 hr). A group of mice was vaccinated by intradermal (D) injection of 25 µg CFA/I (panels D and H). All mice received three vaccinations on day 0, 14 and 28. Fecal samples were collected two weeks after the third immunization (day 42). The samples were processed and evaluated for fecal IgA (panels A-D) and IgG (panels E-H) against CFA/I.

Figure 21:
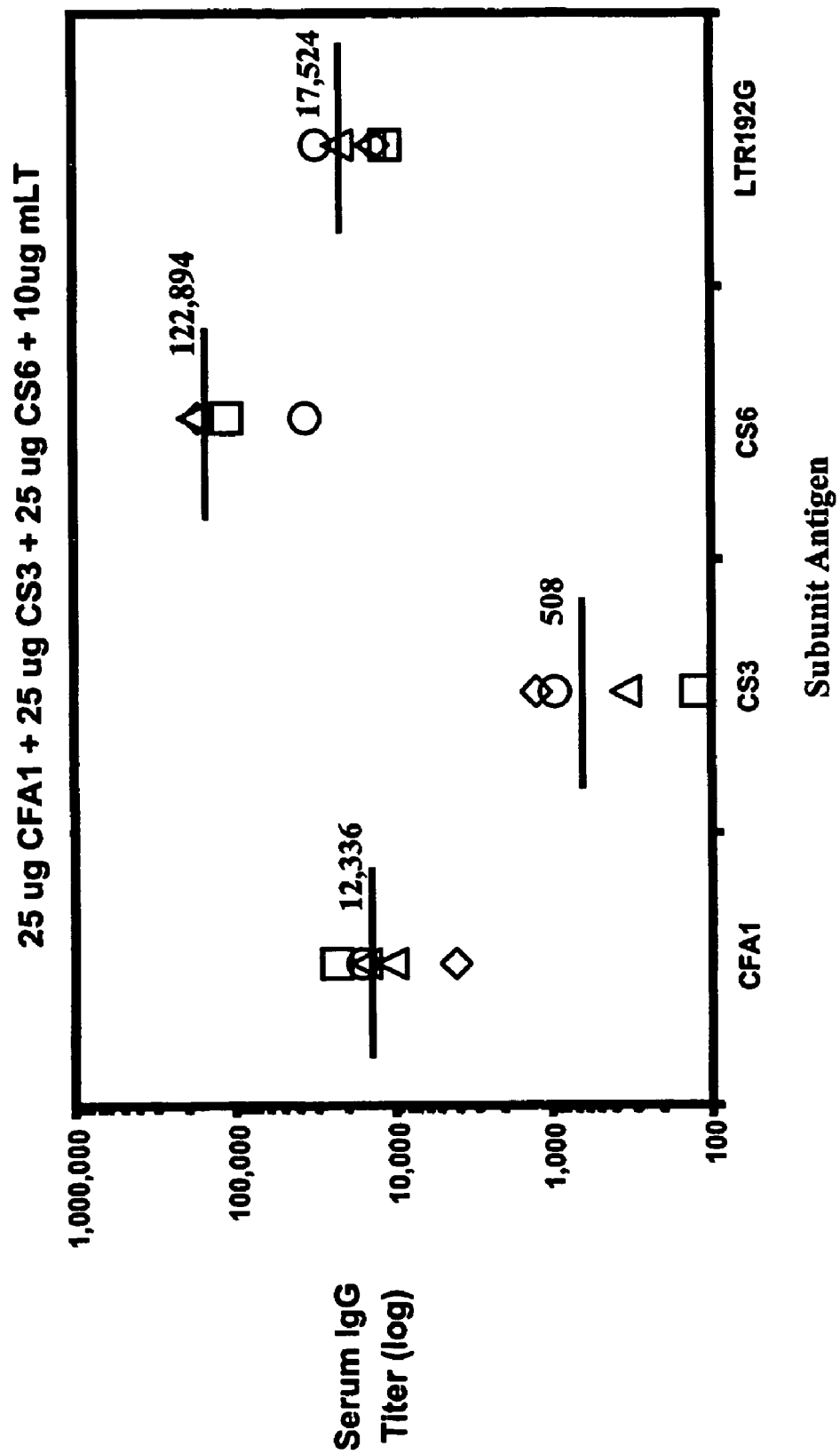
Figure 22A:
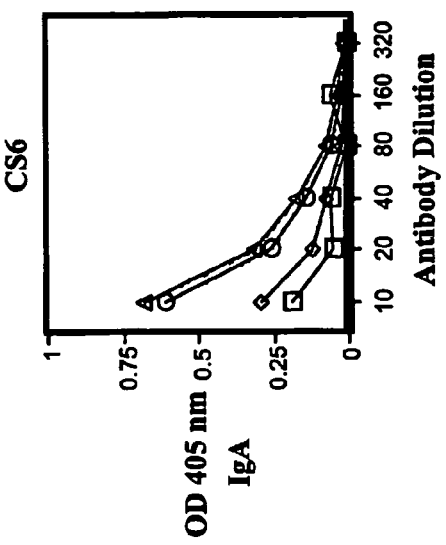
Figure 22B:
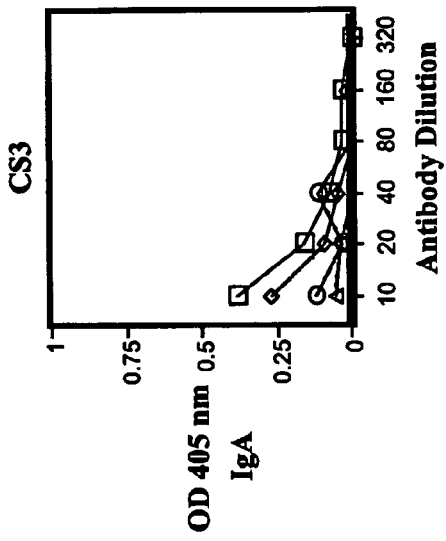
Figure 22C:
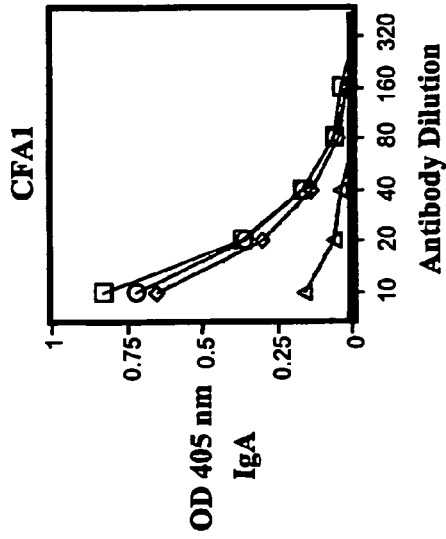
Figure 22D:
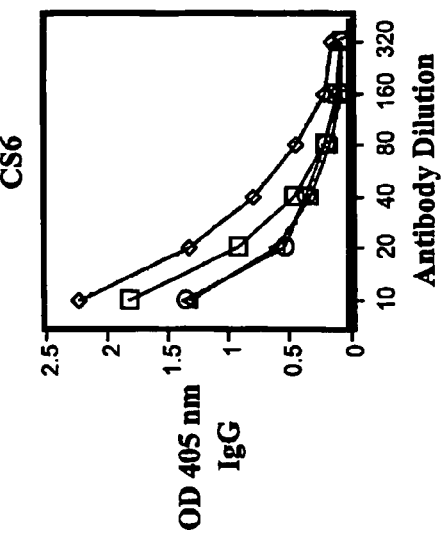
Figure 22E:
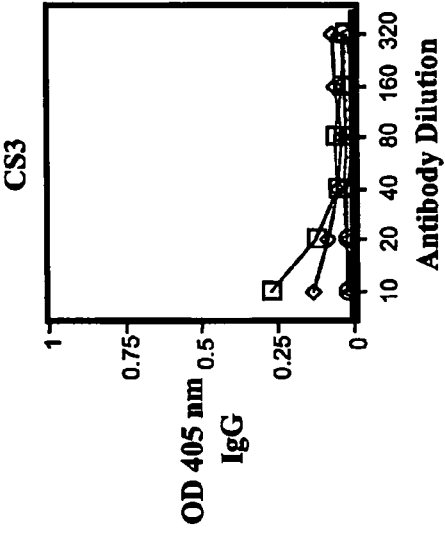
Figure 22F:
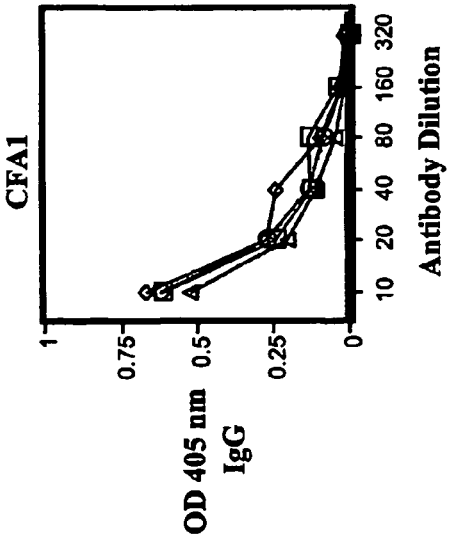

FIG. 21. Serum IgG response to TCI with a tetravalent ETEC subunit vaccine. Mice were shaved on the dorsal caudal surface at the base of the tail 48 hr prior to vaccination. The shaved skin was pretreated by hydration with 10% glycerol and 70% isopropyl alcohol. The hydrated skin was mildly abraded with emery paper 5 times. Gauze patches, affixed to an adhesive backing were loaded with a mixture consisting of 25 µg CFA/I, 25 µg CS3, 25 µg CS6 and 10 µg LTR192G. The patches were applied to the prepared skin and allowed to remain in place for ~18 hr. All mice received a transcutaneous vaccination on day 0 and 14. Serum was collected 10 days after the second immunization (day 24).

FIG. 22A-22F. Detection of fecal IgA (upper panels) and IgG (lower panels) antibodies to colonization factor antigens following TCI with the tetravalent ETEC vaccine. Mice were shaved on the dorsal caudal surface at the base of the tail 48 hr prior to vaccination. The shaved skin was pretreated by hydration with 10% glycerol and 70% isopropyl alcohol. The hydrated skin was then mildly abraded with emery paper. Gauze patches were affixed to an adhesive backing and loaded with the tetravalent vaccine: 25 µg CFA/I, 25 µg CS, 25 µg CS6 and 10 µg LTR192G. The patches were applied overnight (~18 hr). All mice were vaccinated by intradermal (D) injections of 25 µg CFA/I (panels D and H). All mice received three vaccinations on day 0, 14 and 28. Fecal samples were collected two weeks after the third immunization (day 42). The samples were processed and evaluated for fecal IgA to CFA/I(A), CS3 (B), and CS6 (C). Processed samples were also evaluated for fecal IgG to CFA/I (D), CS3 (E), and CS6 (F).

FIG. 23A-23F. Detection of fecal IgA (upper panels) and IgG (lower panels) antibodies to LTR192G following TCI with the tetravalent ETEC vaccine. Mice were shaved on the dorsal caudal surface at the base of the tail 48 hr prior to vaccination. The shaved skin was pretreated by hydration and abrasion as described in FIG. 18. Gauze patches were affixed to an adhesive backing were loaded with the following: 10 g LTR192G (mLT); 25 µg CFA/I and LTR192G; or 25 µg CFA/I, 25 µg CS, 25 µg CS6 and 10 µg LTR192G. The patches were applied overnight (~18 hr). All mice received three vaccinations on day 0,14 and 28. Fecal samples were collected one week after the third immunization (day 35). Samples were processed and evaluated for fecal IgA to LTR192G (panels A-c) and for fecal IgG to LTR192G (panels D-F).

FIG. 24. Transcutaneous vaccination with CS3 and LTR192G subunit vaccines elicit serum antibodies that recognize CS3 expressing ETEC whole cells. Mice were shaved at the base of the tail by standard procedures. The shaved skin was tape stripped 10 times immediately prior to application of the patch. A gauze patch affixed to an adhesive backing was loaded with 25 µg CS3 and 10 µg LTR192G immediately prior to application. The patch was applied for ~18 hr. A group of 10 mice received two patches on day 0 and day 14. Serum was collected 10 days after the second immunization (day 24). The serum was evaluated for antibodies to CS3, LTR192G and ETEC whole cells (E243778).

FIG. 25. Transcutaneous vaccination with killed enterotoxigenic E. coli whole cells (EWC). EWC were prepared by culturing ETEC (strain E243778) in bacterial broth. The cells were harvested by centrifugation and inactivated by overnight (room temperature) fixation with 2.5% formalin. The inactivated, killed whole cells were washed with phosphate buffered saline to remove the formalin. Prior to immunization, the mice were shaved at the base of the tail. The shaved skin was tape stripped 10 times immediately prior to application of the patch. The gauze patch on an adhesive backing was loaded with $10^9$ EWC's and 10 µg LTR192G. A group of 10 mice received were transcutaneously vaccinated on day 0 and 14. Serum was collected 10 days after the second immunization. Sera were evaluated for antibodies to EWC and LTR192G using the ELISA method as described in Materials and Methods. The results in FIG. 22 show that transcutaneous vaccination with killed bacterial whole cells did elicit antibodies that recognized whole cells and LTR192G adjuvant. These results demonstrate that killed ETEC bacteria can be applied to skin with the adjuavant and elicit specific immunity. These results are significant in that this is the first demonstration that TCI is applicable for subunit vaccines and for delivery of killed whole cell vaccines.

Figure 26A:
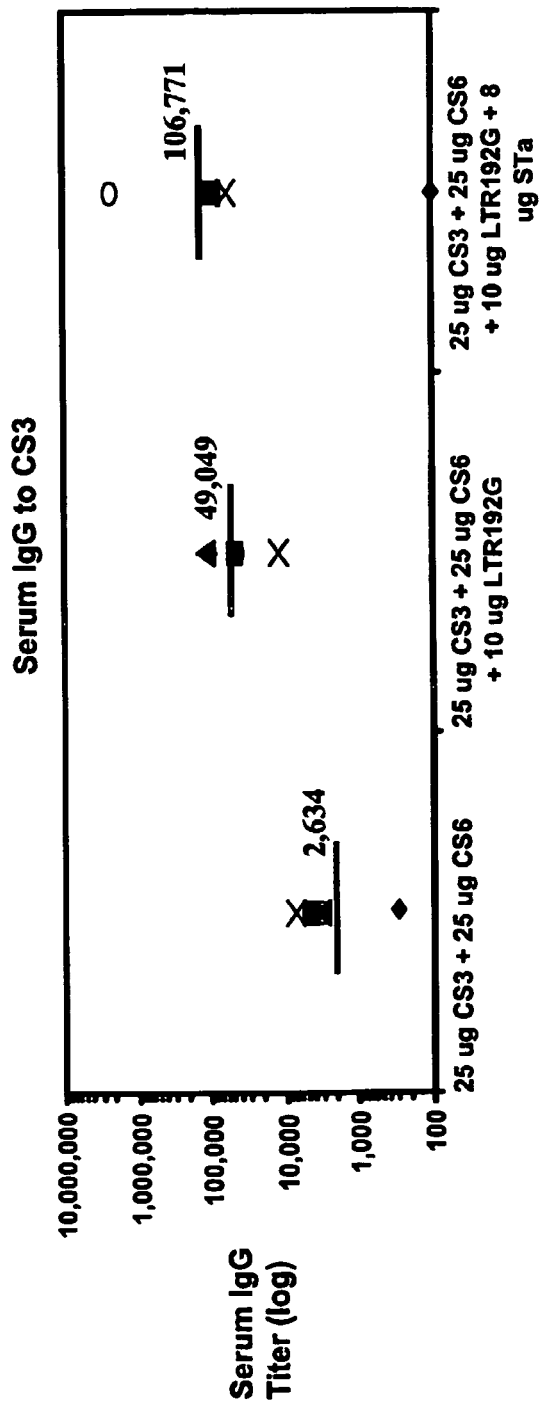
Figure 26B:
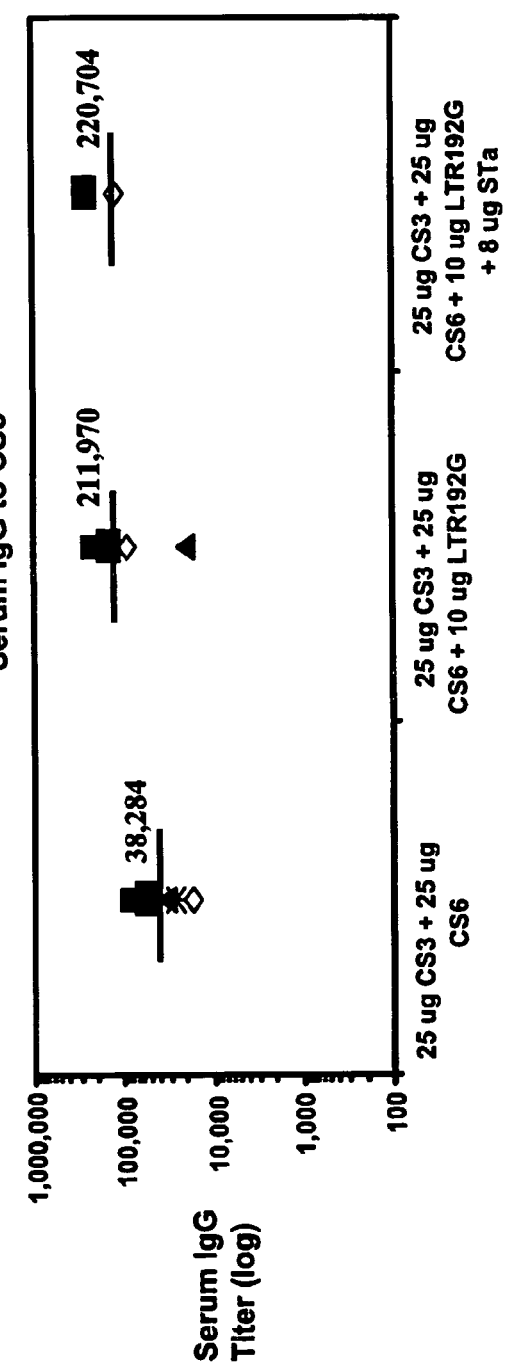

FIG. 26A-26B. Transcutaneous vaccination with a multivalent ETEC vaccine consisting of multiple colonization factors and two enterotoxins, LT and ST. Mice were shaved on the dorsal caudal surface at the base of the tail 48 hr prior to vaccination. The shaved skin was pretreated by hydration with 10% glycerol and 70% isopropyl alcohol and tape stripped 10 times to disrupt the stratum corneum. Gauze patches were affixed to an adhesive backing and loaded with a 25 µl volume of 25 µg CS3/25 µg CS6; 26 µg CS3/25 µg CS6/10 µg LTR192G and 25 µg CS3/25 µg CS6/10 µg LTR192G/8 µg STa. The patches were applied to the prepared skin and allowed to remain in place for ~m18 hr. All mice received a vaccination on day 0, 14 and 28. Serum samples were collected 14 days after the second vaccination (day 42). Panels show serum IgG titer to CS3 (A) and serum IgG titer to CS6 (B).

Figure 27:
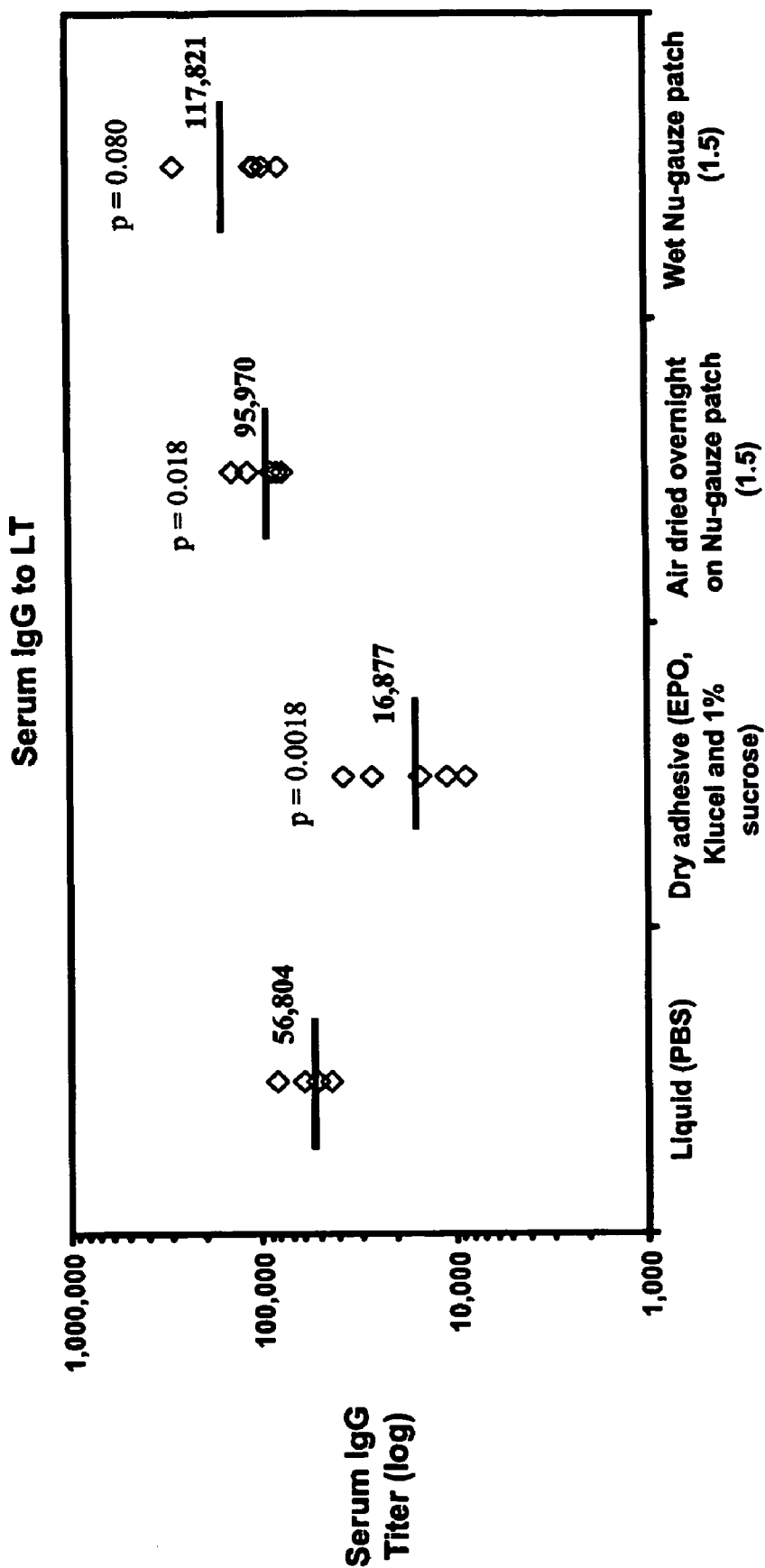

FIG. 27. Wet and dry patch formulations are suitable for manufacturing articles for TCI. In these studies LT was used as an example for preparing different liquid and patch formulations. Briefly, LT was formulated in phosphate buffered saline and 5% lactose; LT was blended with an adhesive (KLUCEL) and spread as a thin film over an occlusive backing and allowed to air-dry at room temperature; LT solution was directly applied to a gauze patch surface and air-dried prior to use; and LT solution was applied to a gauze patch and administered as a fully hydrated patch. For mice receiving the liquid LT formulation, 10 µg LT was applied directly to the skin for 1 hr (with or without covering with gauze) and rinsed off. For mice receiving patches, the different patch formulations were applied for ~24 hr before removal. The skin was hydrated with 10% glycerol and 70% isopropyl alcohol followed by mildly disrupting the stratum corneum with a pumice-containing swab (PDI/NicePak). All mice received two vaccinations on day 0 and day 14 with an equivalent of 10 µg (~1 cm² area). Serum was collected two weeks later (day 28) and evaluated for serum antibodies to LT. Aqueous solutions, protein-in-adhesive, air-dried and fully hydrated patch formulations are suitable for transcutaneous delivery of ETEC antigens.

DESCRIPTION OF SPECIFIC EMBODIMENTS OF THE INVENTION

A system for transcutaneous immunization (TCI) is provided which induces an immune response (e.g., humoral and/or cellular effector specific for an antigen) in an animal or human. The delivery system provides simple, epicutaneous application of a formulation comprised of one or more adjuvants, antigens, and/or polynucleotides (encoding adjuvant and/or antigen) to the skin of an animal or human subject. An antigen-specific immune response is thereby elicited against one or more pathogens like enterotoxigenic *E. coli* (ETEC) with or without the aid of chemical and/or physical penetration enhancement. At least one ingredient or component of the formulation (i.e., antigen or adjuvant) may be provided in dry form prior to administration of the formulation and/or as part of a patch. This system may also be used in conjunction with conventional enteral, mucosal, or parenteral immunization techniques.

Activation of one or more of adjuvant, antigen, and antigen presenting cell (APC) may assist in the promoting the immune response. The APC processes the antigen and then presents one or more epitopes to a lymphocyte. Activation may promote contact between the formulation and the APC (e.g., Langerhans cells, other dendritic cells, macrophages, B lymphocytes), uptake of the formulation by the APC, processing of antigen and/or presentation of epitopes by the APC, migration and/or differentiation of the APC, interaction between the APC and the lymphocyte, or combinations thereof. The adjuvant by itself may activate the APC. For example, a chemokine may recruit and/or activate antigen presenting cells to a site. In particular, the antigen presenting cell may migrate from the skin to the lymph nodes, and then present antigen to a lymphocyte, thereby inducing an antigen-specific immune response. Furthermore, the formulation may directly contact a lymphocyte which recognizes antigen, thereby inducing an antigen-specific immune response.

In addition to eliciting immune reactions leading to activation and/or expansion of antigen-specific B-cell and/or T-cell populations, including antibodies and cytotoxic T lymphocytes (CTL), the invention may positively and/or negatively regulate one or more components of the immune system by using transcutaneous immunization to affect antigen-specific helper (Th1 and/or Th2) or delayed-type hypersensitivity T-cell subsets ($T_{DTH}$). This can be exemplified by the differential behavior of cholera toxin and *E. coli* heat-labile enterotoxin which can result in different T-helper responses. The desired immune response induced by the invention is preferably systemic or regional (e.g., mucosal) but is usually not undesirable immune responses (e.g., atopy, dermatitis, eczema, psoriasis, or other allergic or hypersensitivity reactions). As seen herein, the immune responses elicited are of the quantity and quality that provide therapeutic or prophylactic immune responses useful treatment of infectious disease.

TCI may be practiced with or without skin penetration. For example, chemical or physical penetration enhancement techniques may be used as long as the skin is not perforated through the dermal layer. Hydration of the intact or skin before, during, or immediately after application of the formulation is preferred and may be required in some or many instances. For example, hydration may increase the water content of the topmost layer of skin (e.g., stratum corneum or superficial epidermis layer exposed by penetration enhancement techniques) above 25%, 50% or 75%.

Skin may be swabbed with an applicator (e.g., adsorbent material on a pad or stick) containing hydration or chemical penetration agents or they may be applied directly to skin. For example, aqueous solutions (e.g., water, saline, other buffers), acetone, alcohols (e.g., isopropyl alcohol), detergents (e.g., sodium dodecyl sulfate), depilatory or keratinolytic agents (e.g., calcium hydroxide, salicylic acid, ureas), humectants (e.g., glycerol, other glycols), polymers (e.g., polyethylene or propylene glycol, polyvinyl pyrrolidone), or combinations thereof may be used or incorporated in the formulation. Similarly, abrading the skin (e.g., abrasives like an emery board or paper, sand paper, fibrous pad, pumice), removing a superficial layer of skin (e.g., peeling or stripping with an adhesive tape), microporating the skin using an energy source (e.g., heat, light, sound, electrical, magnetic) or a barrier disruption device (e.g., gun, microneedle), or combinations thereof may act as a physical penetration enhancer. See WO98/29134 for microporation of skin and U.S. Pat. No. 6,090,790 for microneedles and U.S. Pat. No. 6,168,587 for transdermal guns which might be adapted for use in transcutaneous vaccination. The objective of chemical or physical penetration enhancement in conjunction with TCI is to remove at least the stratum corneum or deeper epidermal layer without perforating the skin through to the dermal layer. This is preferably accomplished with minor discomfort at most to the human or animal subject and without bleeding at the site. For example, applying the formulation to intact skin may not involve thermal, optical, sonic, or electromagnetic energy to perforate layers of the skin below the stratum corneum or epidermis.

Formulations which are useful for vaccination are also provided as well as processes for their manufacture. The formulation may be in dry or liquid form. A dry formulation is more easily stored and transported than conventional vaccines, it breaks the cold chain required from the vaccine's place of manufacture to the locale where vaccination occurs. Without being limited to any particular mode of action, another way in which a dry formulation may be an improvement over liquid formulations is that high concentrations of a dry active component of the formulation (e.g., one or more adjuvants and/or antigens) may be achieved by solubilization directly at the site of immunization over a short time span. Moisture from the skin (e.g., perspiration) and an occlusive dressing may hasten this process. In this way, it is possible that a concentration approaching the solubility limit of the active ingredient may be achieved in situ. Alternatively, the dry, active ingredient of the formulation per se may be an improvement by providing a solid particulate form that is taken up and processed by antigen presenting cells. These possible mechanisms are discussed not to limit the scope of the invention or its equivalents, but to provide insight into the operation of the invention and to guide the use of this formulation in immunization and vaccination.

The formulation may be provided as a liquid: cream, emulsion, gel, lotion, ointment, paste, solution, suspension, or other liquid forms. Dry formulations may be provided in various forms: for example, fine or granulated powders, uniform films, pellets, and tablets. The formulation may be dissolved and then dried in a container or on a flat surface (e.g., skin), or it may simply be dusted on the flat surface. It may be air dried, dried with elevated temperature, freeze or spray dried, coated or sprayed on a solid substrate and then dried, dusted on a solid substrate, quickly frozen and then slowly dried under vacuum, or combinations thereof. If different molecules are active ingredients of the formulation, they may be mixed in solution and then dried, or mixed in dry form only. Compartments or chambers of the patch may be used to separate active ingredients so that only one of the antigens or adjuvants is kept in dry form prior to administration; separating liquid and solid in this manner allows control over the time and rate of the dissolving of at least one dry, active ingredient.

A "patch" refers to a product which includes a solid substrate (e.g., occlusive or non-occlusive surgical dressing) as well as at least one active ingredient. Liquid may be incorporated in a patch (i.e., a wet patch). One or more active components of the formulation may be applied on the substrate, incorporated in the substrate or adhesive of the patch, or combinations thereof. A dry patch may or may not use a liquid reservoir to solubilize the formulation.

Formulation in liquid or solid form may be applied with one or more adjuvants and/or antigens both at the same or separate sites or simultaneously or in frequent, repeated applications. The patch may include a controlled-release reservoir or a rate-controlling matrix or membrane may be used which allows stepped release of adjuvant and/or antigen. It may contain a single reservoir with adjuvant and/or antigen, or multiple reservoirs to separate individual antigens and adjuvants. The patch may include additional antigens such that application of the patch induces an immune response to multiple antigens. In such a case, antigens may or may not be derived from the same source, but they will have different chemical structures so as to induce an immune response specific for different antigens. Multiple patches may be applied simultaneously; a single patch may contain multiple reservoirs. For effective treatment, multiple patches may be applied at intervals or constantly over a period of time; they may be applied at different times, for overlapping periods, or simultaneously. At least one adjuvant and/or adjuvant may be maintained in dry form prior to administration. Subsequent release of liquid from a reservoir or entry of liquid into a reservoir containing the dry ingredient of the formulation will at least partially dissolve that ingredient.

Solids (e.g., particles of nanometer or micrometer dimensions) may also be incorporated in the formulation. Solid forms (e.g., nanoparticles or microparticles) may aid in dispersion or solubilization of active ingredients; assist in carrying the formulation through superficial layers of the skin; provide a point of attachment for adjuvant, antigen, or both to a substrate that can be opsonized by antigen presenting cells, or combinations thereof. Prolonged release of the formulation from a porous solid formed as a sheet, rod, or bead acts as a depot.

The formulation may be manufactured under aseptic conditions acceptable to appropriate regulatory agencies (e.g., Food and Drug Administration) for biologicals and vaccines. Optionally, components such as dessicants, excipients, stabilizers, humectants, preservatives, adhesives, patch materials, or combinations thereof may be included in the formulation even though they are immunologically inactive. They may, however, have other desirable properties or characteristics.

A single or unit dose of formulation suitable for administration is provided. The amount of adjuvant or antigen in the unit dose may be anywhere in a broad range from about 0.001 µg to about 10 mg. This range may be from about 0.1 µg to about 1 mg; a narrower range is from about 5 µg to about 500 µg. Other suitable ranges are between about 1 µg and about 10 µg, between about 10 µg and about 50 µg, between about 50 µg and about 200 µg, and between about 1 mg and about 5 mg. A preferred dose for a toxin is about 50 µg or 100 µg or less (e.g., from about 1 µg to about 50 µg or 100 µg). The ratio between antigen and adjuvant may be about 1:1 (e.g., E. coli heat-labile enterotoxin when it is both antigen and adjuvant) but higher ratios may be suitable for poor antigens (e.g., about 1:10 or less), or lower ratios of antigen to adjuvant may also be used (e.g., about 10:1 or more). The native ratios between LT and ETEC antigens may be used for whole-cell or lysate formulations.

A formulation comprising adjuvant and antigen or polynucleotide may be applied to skin of a human or animal subject, antigen is presented to immune cells, and an antigen-specific immune response is induced. This may occur before, during, or after infection by pathogen. Only antigen or polynucleotide encoding antigen may be required, but no additional adjuvant, if the immunogenicity of the formulation is sufficient to not require adjuvant activity. The formulation may include an additional antigen such that application of the formulation induces an immune response against multiple antigens (i.e., multivalent). In such a case, antigens may or may not be derived from the same source, but the antigens will have different chemical structures so as to induce immune responses specific for the different antigens. Antigen-specific lymphocytes may participate in the immune response and, in the case of participation by B lymphocytes, antigen-specific antibodies may be part of the immune response. The formulations described above may include dessicants, excipients, humectants, stabilizers, preservatives, adhesives, and patch materials known in the art.

The invention is used to treat a subject (e.g., a human or animal in need of treatment such as prevention of disease, protection from effects of infection, therapy of existing disease or symptoms, or combinations thereof). When the antigen is derived from a pathogen, the treatment may vaccinate the subject against infection by the pathogen or against its pathogenic effects such as those caused by toxin secretion. The invention may be used therapeutically to treat existing disease, protectively to prevent disease, to reduce the severity and/or duration of disease, to ameliorate symptoms of disease, or combinations thereof.

The application site may be protected with anti-inflammatory corticosteroids such as hydrocortisone, triamcinolone and mometazone or non-steroidal anti-inflammatory drugs (NSAID) to reduce possible local skin reaction or modulate the type of immune response. Similarly, anti-inflammatory steroids or NSAID may be included in the patch material, or liquid or solid formulations; and corticosteroids or NSAID may be applied after immunization. IL-10, TNF-$\alpha$, other immunomodulators may be used instead of the anti-inflammatory agents. Moreover, the formulation may be applied to skin overlying more than one draining lymph node field using either single or multiple applications. The formulation may include additional antigens such that application induces an immune response to multiple antigens. In such a case, the antigens may or may not be derived from the same source, but the antigens will have different chemical structures so as to induce an immune response specific for the different antigens. Multi-chambered patches could allow more effective delivery of multivalent vaccines as each chamber covers different antigen presenting cells. Thus, antigen presenting cells would encounter only one antigen (with or without adjuvant) and thus would eliminate antigenic competition and thereby enhancing the response to each individual antigen in the multivalent vaccine.

The formulation may be epicutaneously applied to skin to prime or boost the immune response in conjunction with penetration techniques or other routes of immunization. Priming by transcutaneous immunization (TCI) with either single or multiple applications may be followed with enteral, mucosal, parenteral, and/or transdermal techniques for boosting immunization with the same or altered antigens. Priming by enteral, mucosal, parenteral, and/or transdermal immunization with either single or multiple applications may be followed with transcutaneous techniques for boosting immunization with the same or altered antigens. It should be noted that TCI is distinguished from conventional topical techniques like mucosal or transdermal immunization because the former requires a mucous membrane (e.g., lung, mouth, nose, rectum) not found in the skin and the latter requires perforation of the skin through the dermis. The formulation may include additional antigens such that application to skin induces an immune response to multiple antigens.

In addition to antigen and adjuvant, the formulation may comprise a vehicle. For example, the formulation may comprise an AQUAPHOR, FREUND, RIBI or SYNTEX emulsion; water-in-oil emulsions (e.g., aqueous creams, ISA-720), oil-in-water emulsions (e.g., oily creams, ISA-51, MF59), microemulsions, anhydrous lipids and oil-in-water emulsions, other types of emulsions; gels, fats, waxes, oil, silicones, and humectants (e.g., glycerol).

Antigen may be derived from any pathogen that infects a human or animal subject (e.g., bacterium, virus, fungus, or protozoan). The chemical structure of the antigen may be described as one or more of carbohydrate, fatty acid, and protein (e.g., glycolipid, glycoprotein, lipoprotein). Proteinaceous antigen is preferred. The molecular weight of the antigen may be greater than 500 daltons, 800 daltons, 1000 daltons, 10 kilodaltons, 100 kilodaltons, or 1000 kilodaltons. Chemical or physical penetration enhancement may be preferred for macromolecular structures like cells, viral particles, and molecules of greater than one megadalton (e.g., CS6 antigen), but techniques like hydration and swabbing with a solvent may be sufficient to induce immunization across the skin. Antigen may be obtained by recombinant techniques, chemical synthesis, or at least partial purification from a natural source. It may be a chemical or recombinant conjugates: for example, linkage between chemically reactive groups or protein fusion. Antigen may be provided as a live cell or virus, an attenuated live cell or virus, a killed cell, or an inactivated virus. Alternatively, antigen may be at least partially purified in cell-free form (e.g., cell or viral lysate, membrane or other subcellular fraction). Because most adjuvants would also have immunogenic activity and would be considered antigens, adjuvants would also be expected to have the aforementioned properties and characteristics of antigens.

The choice of adjuvant may allow potentiation or modulation of the immune response. Moreover, selection of a suitable adjuvant may result in the preferential induction of a humoral or cellular immune response, specific antibody isotypes (e.g., IgM, IgD, IgA1, IgA2, IgE, IgG1, IgG2, IgG3, and/or IgG4), and/or specific T-cell subsets (e.g., CTL, Th1, Th2 and/or $T_{DTH}$). The adjuvant is preferably a chemically activated (e.g., proteolytically digested) or genetically activated (e.g., fusions, deletion or point mutants) ADP-ribosylating exotoxin or B subunit thereof. Adjuvant, antigen, or both may optionally be provided in the formulation with a polynucleotide (e.g., DNA, RNA, cDNA, cRNA) encoding the adjuvant or antigen as appropriate. Covalently closed, circular DNA such as plasmids are preferred forms of the polynucleotide; however, linear forms may also be used. The polynucleotide may include a region such as an origin of replication, centromere, telomere, promoter, enhancer, silencer, transcriptional initiation or termination signal, splice acceptor or donor site, ribosome binding site, translational initiation or termination signal, polyadenylation signal, cellular localization signal, protease cleavage site, polylinker site, or combinations thereof as are found in expression vectors.

An "antigen" is an active component of the formulation which is specifically recognized by the immune system of a human or animal subject after immunization or vaccination. The antigen may comprise a single or multiple immunogenic epitopes recognized by a B-cell receptor (i.e., secreted or membrane-bound antibody) or a T-cell receptor. Proteinaceous epitopes recognized by T-cell receptors have typical lengths and conserved amino acid residues depending on whether they are bound by major histocompatibility complex (MHC) Class I or Class II molecules on the antigen presenting cell. In contrast, proteinaceous epitopes recognized antibody may be of variable length including short, extended oligopeptides and longer, folded polypeptides. Single amino acid differences between epitopes may be distinguished. The antigen is capable of inducing an immune response against a molecule of a pathogen (e.g., a CS6 antigen is capable of inducing a specific immune response against the CS6 molecule of ETEC). Thus, antigen is usually identical or at least derived from the chemical structure of a specific molecule of the pathogen, but mimetics which are only distantly related to such chemical structures may also be successfully used.

An "adjuvant" is an active component of the formulation to assist in inducing an immune response to the antigen. Adjuvant activity is the ability to increase the immune response to a heterologous antigen (i.e., antigen which is a separate chemical structure from the adjuvant) by inclusion of the adjuvant itself in a formulation or in combination with other components of the formulation or particular immunization techniques. As noted above, a molecule may contain both antigen and adjuvant activities by chemically conjugating antigen and adjuvant or genetically fusing coding regions of antigen and adjuvant; thus, the formulation may contain only one ingredient or component.

The term "effective amount" is meant to describe that amount of adjuvant or antigen which induces an antigen-specific immune response. A "subunit" immunogen or vaccine is a formulation comprised of active components (e.g., adjuvant, antigen) which have been isolated from other cellular or viral components of the pathogen (e.g., membrane or polysaccharide components like endotoxin) by recombinant techniques, chemical synthesis, or at least partial purification from a natural source.

Induction of an immune response may provide a treatment such as, for example, prophylactic or therapeutic vaccination for an infectious disease. A product or method "induces" when its presence or absence causes a statistically significant change in the immune response's magnitude and/or kinetics; change in the induced elements of the immune system (e.g., humoral vs. cellular, Th1 vs. Th2); effect on the health and well-being of the subject; or combinations thereof.

The term "draining lymph node field" as used in the invention means an anatomic area over which the lymph collected is filtered through a set of defined lymph nodes (e.g., cervical, axillary, inguinal, epitrochelear, popliteal, those of the abdomen and thorax). Thus, the same draining lymph node field may be targeted by immunization (e.g., enteral, mucosal, parenteral, transcutaneous, transdermal) within the few days required for antigen presenting cells to migrate to the lymph nodes if the sites and times of immunization are spaced to bring different components of the formulation together (e.g., two closely spaced patches with either adjuvant or antigen may be effective when neither alone could successfully used). For example, a patch delivering adjuvant by the transcutaneous technique may be placed on the same arm as is injected with a conventional vaccine to boost its effectiveness in elderly, pediatric, or other immunologically compromised populations. In contrast, applying patches to different limbs may prevent an adjuvant-containing patch from boosting the effectiveness of a patch containing only antigen.

Without being bound to any particular theory for the operation of the invention but only to provide an explanation for our observations, we hypothesize that this transcutaneous delivery system carries antigen to cells of the immune system where an immune response is induced. The antigen may pass through the normally present protective outer layers of the skin (i.e., stratum corneum) and induce the immune response directly, or through an antigen presenting cell population in the epidermis (e.g., macrophage, tissue macrophage, Langerhans cell, other dendritic cells, B lymphocyte, or Kupffer cell) that presents processed antigen to lymphocytes. Thus, with or without penetration enhancement techniques, the dermis is not penetrated as in subcutaneous injection or transdermal techniques. Optionally, the antigen may pass through the stratum corneum via a hair follicle or a skin organelle (e.g., sweat gland, oil gland).

Transcutaneous immunization with bacterial ADP-ribosylating exotoxins (bARE) as an example, may target the epidermal Langerhans cell, known to be among the most efficient of the antigen presenting cells (APC). Maturation of APC may be assessed by morphology and phenotype (e.g., expression of MHC Class II molecules, CD83, or co-stimulatory molecules). We have found that bARE appear to activate Langerhans cells when applied epicutaneously to intact skin. Adjuvants such as trypsin-cleaved bARE may enhance Langerhans cell activation. Langerhans cells direct specific immune responses through phagocytosis of the antigens, and migration to the lymph nodes where they act as APC to present the antigen to lymphocytes, and thereby induce a potent antibody response. Although the skin is generally considered a barrier to pathogens, the imperfection of this barrier is attested to by the numerous Langerhans cells distributed throughout the epidermis that are designed to orchestrate the immune response against organisms invading through the skin. According to Udey (Clin Exp Immunol, 107:s6-s8, 1997):

Langerhans cells are bone-marrow derived cells that are present in all mammalian stratified squamous epithelia. They comprise all of the accessory cell activity that is present in uninflamed epidermis, and in the current paradigm are essential for the initiation and propagation of immune responses directed against epicutaneously applied antigens. Langerhans cells are members of a family of potent accessory cells ('dendritic cells') that are widely distributed, but infrequently represented, in epithelia and solid organs as well as in lymphoid tissue.
>
> It is now recognized that Langerhans cells (and presumably other dendritic cells) have a life cycle with at least two distinct stages. Langerhans cells that are located in epidermis constitute a regular network of antigen-trapping 'sentinel' cells. Epidermal Langerhans cells can ingest particulates, including microorganisms, and are efficient processors of complex antigens. However, they express only low levels of MHC class I and II antigens and costimulatory molecules (ICAM-1, B7-1 and B7-2) and are poor stimulators of unprimed T cells. After contact with antigen, some Langerhans cells become activated, exit the epidermis and migrate to T-cell-dependent regions of regional lymph nodes where they localize as mature dendritic cells. In the course of exiting the epidermis and migrating to lymph nodes, antigen-bearing epidermal Langerhans cells (now the 'messengers') exhibit dramatic changes in morphology, surface phenotype and function. In contrast to epidermal Langerhans cells, lymphoid dendritic cells are essentially non-phagocytic and process protein antigens inefficiently, but express high levels of MHC class I and class II antigens and various costimulatory molecules and are the most potent stimulators of naive T cells that have been identified."

The potent antigen presenting capability of Langerhans cells can be exploited for transcutaneously-delivered immunogens and vaccines. An immune response using the skin's immune system may be achieved by delivering the formulation only to Langerhans cells in the stratum corneum (i.e., the outermost layer of the skin consisting of cornified cells and lipids) and subsequently activating the Langerhans cells to take up antigen, migrate to B-cell follicles and/or T-cell dependent regions, and present the antigen to B and/or T lymphocytes. If antigens other that bARE (e.g., toxin, colonization or virulence factor) are to be phagocytosed by Langerhans cells, then these antigens could also be transported to the lymph node for presentation to T lymphocytes and subsequently induce an immune response specific for that antigen. Thus, a feature of TCI is the activation of the Langerhans cell, presumably by bARE or derivatives thereof, chemokines, cytokines, PAMP, or other Langerhans cell activating substance including contact sensitizers and adjuvants. Increasing the size of the skin population of Langerhans cells or their state of activation would also be expected to enhance the immune response (e.g., acetone pretreatment). In aged subjects or Langerhans cell-depleted skin (i.e., from UV damage), it may be possible to replenish the population of Langerhans cells (e.g., tretinoin pretreatment).

Adjuvants such as bARE are known to be highly toxic when injected or given systemically. But if placed on the surface of intact skin (i.e., epicutaneous), they are unlikely to induce systemic toxicity. Thus, the transcutaneous route may allow the advantage of adjuvant effects without systemic toxicity. A similar absence of toxicity could be expected if the skin were penetrated only below the stratum corneum (e.g., near or at the epidermis), but not through the dermis. Thus, the ability to induce activation of the immune system through the skin confers the unexpected advantage of potent immune responses without systemic toxicity.

The magnitude of the antibody response induced by affinity maturation and isotype switching to predominantly IgG antibodies is generally achieved with T-cell help, and activation of both Th1 and Th2 pathways is suggested by the production of IgG1 and IgG2a. Alternatively, a large antibody response may be induced by a thymus-independent antigen type 1 (TI-1) which directly activates the B lymphocyte or could have similar activating effects on B lymphocytes such as up-regulation of MHC Class II, B7, CD40, CD25, and ICAM-1 molecules.

The spectrum of commonly known skin immune responses is represented by atopy and contact dermatitis. Contact dermatitis, a pathogenic manifestation of Langerhans cell activation, is directed by Langerhans cells which phagocytose antigen, migrate to lymph nodes, present antigen, and sensitize T lymphocytes that migrate to the skin and cause the intense destructive cellular response that occurs at affected skin sites. Such responses are not generally known to be associated with antigen-specific IgG antibodies. Atopic dermatitis may utilize the Langerhans cell in a similar fashion, but is identified with Th2 cells and is generally associated with high levels of IgE antibody.

On the other hand, transcutaneous immunization with bARE provides a useful and desirable immune response. There are usually no findings typical of atopy or contact dermatitis given the high levels of IgG that are induced. Cholera toxin or *E. coli* heat-labile enterotoxin epicutaneously applied to skin can achieve immunization in the absence of lymphocyte infiltration 24, 48 and 120 hours after immunization. The minor skin reactivity seen in preclinical trials were easily treated. This indicates that Langerhans cells engaged by transcutaneous immunization as they "comprise all of the accessory cell activity that is present in uninflamed epidermis, and in the current paradigm are essential for the initiation and propagation of immune responses directed against epicutaneously applied antigens" (Udey, 1997). The uniqueness of the transcutaneous immune response here is also indicated by the both high levels of antigen-specific IgG antibody, and the type of antibody produced (e.g., IgM, IgG1, IgG2a, IgG2b, IgG3 and IgA) and generally the absence of antigen specific IgE antibody. Transcutaneous immunization could conceivably occur in tandem with skin inflammation if sufficient activation of antigen presenting cells and T lymphocytes were to occur in a transcutaneous response coexisting with atopy or contact dermatitis.

Transcutaneous targeting of Langerhans cells may also be used in tandem with agents to deactivate all or part of their antigen presenting function, thereby modifying immunization or preventing sensitization. Techniques to modulate Langerhans activation or other skin immune cells include, for example, the use of anti-inflammatory steroidal or non-steroidal agents (NSAID); cyclosporin, FK506, rapamycin, cyclophosphamide, glucocorticoids, or other immunosuppressants; interleukin-10; interleukin-1 monoclonal antibodies (mAB) or soluble receptor antagonists (RA); interleukin-1 converting enzyme (ICE) inhibitors; or depletion via superantigens such as through Staphylococcal enterotoxin A (SEA) induced epidermal Langerhans cell depletion. Similar compounds may be used to modify the innate response of Langerhans cells and induce different T-helper responses (Th1 or Th2) or may modulate skin inflammatory responses to decrease potential side effects of the immunization. Similarly, lymphocytes may be immunosuppressed before, during or after immunization by administering immunosuppressant separately or by coadministration of immunosuppressant with the formulation. For example, it may be possible to induce a potent systemic protective immune responses with agents that would normally result in allergic or irritant contact hypersensitivity but adding inhibitors of ICE may alleviate adverse skin reactions.

TCl may be accompished through the ganglioside GM1 binding activity of CT, LT, or subunits thereof (e.g., CTB or LTB). Ganglioside GM1 is a ubiquitous cell membrane glycolipid found in all mammalian cells. When the pentameric CT B subunit binds to the cell surface, a hydrophilic pore is formed which allows the A subunit to insert across the lipid bilayer. Other binding targets on the APC may be utilized. The LT B subunit binds to ganglioside GM1 in addition to other gangliosides and its binding activities may account for its the fact that LT is highly immunogenic on the skin.

TCl with bARE or B subunit-containing fragments or conjugates thereof may require their GM1 ganglioside binding activity. When mice were transcutaneously immunized with CT, CTA and CTB, CT and CTB were required for induction of an immune response. CTA contains the ADP-ribosylating exotoxin activity but only CT and CTB containing the binding activity are able to induce an immune response indicating that the B subunit was necessary and sufficient to immunize through the skin. We conclude that the Langerhans cells or other APC may be activated by CTB binding to its cell surface resulting in a transcutaneous immune response.

Antigen

A transcutaneous immunization system delivers agents to specialized cells (e.g., antigen presentation cell, lymphocyte) that produce an immune response. These agents as a class are called antigens. Antigen may be composed of chemical structures such as, for example, carbohydrate, glycolipid, glycoprotein, lipid, lipoprotein, phospholipid, polypeptide, conjugates thereof, or any other material known to induce an immune response. Antigen may be provided as a whole organism such as, for example, a bacterium or virion; antigen may be obtained from an extract or lysate, either from whole cells or membrane alone; or antigen may be chemically synthesized or produced by recombinant technology.

Antigen of the invention may be expressed by recombinant technology, preferably as a fusion with an affinity or epitope tag; chemical synthesis of an oligopeptide, either free or conjugated to carrier proteins, may be used to obtain antigen of the invention. Oligopeptides are considered a type of polypeptide. Oligopeptide lengths of 6 residues to 20 residues are preferred. Polypeptides may also by synthesized as branched structures (e.g., U.S. Pat. Nos. 5,229,490 and 5,390,111). Antigenic polypeptides include, for example, synthetic or recombinant B-cell and T-cell epitopes, universal T-cell epitopes, and mixed T-cell epitopes from one organism or disease and B-cell epitopes from another. Antigen obtained through recombinant technology or peptide synthesis, as well as antigen obtained from natural sources or extracts, may be purified by the antigen's physical and chemical characteristics, preferably by fractionation or chromatography. Recombinants may combine B subunits or chimeras of bARE. A multivalent antigen formulation may be used to induce an immune response to more than one antigen at the same time. Conjugates may be used to induce an immune response to multiple antigens, to boost the immune response, or both. Additionally, toxins may be boosted by the use of toxoids, or toxoids boosted by the use of toxins. Transcutaneous immunization may be used to boost responses induced initially by other routes of immunization such as by oral, nasal or parenteral routes. Antigen includes, for example, toxins, toxoids, subunits thereof, or combinations thereof (e.g., cholera toxin, tetanus toxoid); additionally, toxins, toxoids, subunits thereof, or combinations thereof may act as both antigen and adjuvant. Such oral/transcutaneous or transcutaneous/oral immunization may be especially important to enhance mucosal immunity in diseases where mucosal immunity correlates with protection.

Antigen may be solubilized in a buffer or water or organic solvents such as alcohol or DMSO, or incorporated in gels, emulsion, microemulsions, and creams. Suitable buffers include, but are not limited to, phosphate buffered saline $Ca^{++}/Mg^{++}$ free, phosphate buffered saline, normal saline (150 mM NaCl in water), and Hepes or Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH may be used as a diluent after solubilization in dilute acetic acid. Glycerol may be a suitable non-aqueous buffer for use in the invention.

A hydrophobic antigen can be solubilized in a detergent or surfactant, for example a polypeptide containing a membrane-spanning domain. Furthermore, for formulations containing liposomes, an antigen in a detergent solution (e.g., cell membrane extract) may be mixed with lipids, and liposomes then may be formed by removal of the detergent by dilution, dialysis, or column chromatography. Certain antigens (e.g., membrane proteins) need not be soluble per se, but can be inserted directly into a lipid membrane (e.g., a virosome), in a suspension of virion alone, or suspensions of microspheres or heat-inactivated bacteria which may be taken up by activate antigen presenting cells (e.g., opsonization). Antigens may also be mixed with a penetration enhancer as described in WO 99/43350.

Many antigens are known in the art which can be used to vaccinate human or animal subjects and induce an immune response specific for particular pathogens, as well as methods of preparing antigen, determining a suitable dose of antigen, assaying for induction of an immune response, and treating infection by a pathogen (e.g., bacterium, virus, fungus, or protozoan).

The effect of *Escherichia coli* infection of mammals is dependent on the particular strain of organism. Many beneficial *E. coli* are present in the intestines. Since the initial association with diarrheal illness, five categories of diarrheagenic *E. coli* have been identified: enterotoxigenic (ETEC), enteropathogenic (EPEC), enterohemorrhagic (EHEC), enteroaggregative (EAggEC), and enteroinvasive (EIEC). They are grouped according to characteristic virulence properties, such as elaboration of toxins and colonization factors and/or by specific types of interactions with intestinal epithelial cells. ETEC are the most common of the diarrheagenic *E. coli* and pose the greatest risk to travelers. Strains which have been cultured from humans include B7A (CS6, LT, STa), H10407 (CFA/I, LT, STa) and E24377A (CS3, CS1, LT, STa). They may be used singly or in combination as whole-cell sources of antigen providing a variety of different toxins and colonization factors.

There is a need for vaccines which are specific against enterotoxigenic *E. coli* that give rise to antibodies that cross-react with and cross-protect against the more common colonization and virulence factors. The CS4-CFA/I family of fimbrial proteins are found on some of the more prevalent enterotoxigenic *E. coli* strains: there are six members of this family of ETEC antigens, CFA/I, CS1, CS2, CS4, CS17, and PCF 0166.

Colonization factor antigens (CFA) of ETEC are important in the initial step of colonization and adherence of the bacterium to intestinal epithelia. In epidemiological studies of adults and children with diarrhea, CFA/I is found in a large percentage of morbidity attributed to ETEC. The CFA/I is present on the surfaces of bacteria in the form of pili (fimbriae), which are rigid, 7 nm diameter protein fibers composed of repeating pilin subunits. The CFA/I antigens promote mannose-resistant attachment to human brush borders with an apparent sialic acid sensitivity. Hence, it has been postulated that a vaccine that establishes immunity against these proteins may prevent attachment to host tissues and subsequent disease.

Other antigens including CS3, CS5, and CS6. CFA/I, CS3 and CS6 may occur alone, but with rare exception CS1 is only found with CS3, CS2 with CS3, CS4 with CS6 and CS5 with CS6. Serological studies show these antigens occur in strains accounting for up to about 75% or as little as about 25% of ETEC cases, depending on the location of the study.

Consensus peptides have been described in U.S. Pat. No. 5,914,114 which raise antibodies against the antigens of all members of the *E. coli* family CS4-CFA/I. While the N-terminus of members of this family shows a high degree of identity, the remainder of the sequence of the proteins shows less relatedness across the strains. Consensus peptides encompass known linear B- and T-cell epitopes, and bears a high degree of evolutionary relatedness across the six different colonization factors. For example, consensus peptides have the amino acid sequence (an amino acid residue may be added to either termini or modified internally to provide a reactive linkage): VEKNITVTASVDPTIDLLQADGSALP-SAVALTYSPA (SEQ ID NO: 1) and VEKNITVTASVDP-TIDLLQADGSALPASVALTYSPA (SEQ ID NO: 2).

These consensus peptides were constructed based on the homologous regions of the CFA/I, CS1, CS2, CS4, CS17, and PCF 0166 antigens.

TABLE 1

Alignment of antigens of the CS4-CFA/I family
(SEQ ID NOS: 3-8)

| Antigen | Amino Acid Sequence |
|---------|---------------------|
| CFA/I | VEKNITVTASVDPVIDLLQADGSALPSAVALTYSPAS |
| CS1 | VEKTISVTASVDPTVDLLQSDGSALPNSVALTYSPAV |
| CS2 | AEINITVTASVDPVIDLLQA |
| CS4 | VEKNITVTASVDPTIDILQADGSYLPTAVELTYSPAA |
| CS17 | VEKNITVRASVDKLIDLLQADGTSLPDSIALTYSVA |
| PCF0166 | VEKNITVTASVDPTIDILQANGSAL |

CS6, a component of colonization factor IV (CFA/IV), can also be found in more than about 25% of ETEC strains in serological surveys (e.g., soldiers in the Middle East). The nucleotide sequences of CS3 and CS6 antigens, along with a process for producing them, are described in U.S. Pat. No. 5,698,416.

Other antigens which may be used are toxins that cause enteric disease such as, for example, shiga toxin and *E. coli* enterotoxins. Heat-labile enterotoxin (LT) is described below, but heat-stable enterotoxins (e.g., STa, STb) which cause disease symptoms may also be neutralized by antibody. LT is a periplasmic toxin and ST is an extracellular toxin. STa is methanol soluble and STb is methanol insoluble. Two different precursors are used: STa is a 18-19 amino acid peptide and STb is a 48 amino acid peptide with no sequence similarity between them. Conjugates between LT and ST or ST multimers may also be used (see U.S. Pat. No. 4,886,663).

It would be advantageous for a vaccine to be developed for a broad range of common traveler's diseases, especially enteric infectious diseases. For example, campylobacteriosis (*Campylobacter jejuni*), giardiasis (*Giardia intestinalis*), hepatitis (hepatitis virus A or B), malaria (*Plasmodium falciparum*, *P. vivax*, *P. ovale*, and *P. malarae*), shigellosis (*Shigella boydii*, *S. dysenterae*, *S. flexneri*, and *S. sonnet*), viral gastroenteritis (rotavirus), and combinations thereof may be treated by including antigens derived from the responsible pathogen. Systemic or mucosal antibodies that neutralize toxicity or block attachment and entry into the cell are desirable. An immune response which is specific for molecules associated with pathogens (e.g., toxins, membrane proteins) may be induced by various routes of administration (e.g., enteral, mucosal, parenteral, transcutaneous).

Adjuvant

The formulation contains an adjuvant, although a single molecule may contain both adjuvant and antigen properties (e.g., *E. coli* heat-labile enterotoxin). Adjuvants are substances that are used to specifically or non-specifically potentiate an antigen-specific immune response, perhaps through activation of antigen presenting cells (e.g., dendritic cells in various layers of the skin, especially Langerhans cells). See also Elson et al. (in *Handbook of Mucosal Immunology*, Academic Press, 1994). Although activation may initially occur in the epidermis or dermis, the effects may persist as the dendritic cells migrate through the lymph system and the circulation. Adjuvant may be formulated and applied with or without antigen, but generally, activation of antigen presenting cells by adjuvant occurs prior to presentation of antigen. Alternatively, they may be separately presented within a short interval of time but targeting the same anatomical region (e.g., the same draining lymph node field).

Adjuvants include, for example, chemokines (e.g., defensins, HCC-1, HCC4, MCP-1, MCP-3, MCP4, MIP-1α, MIP-1β, MIP-1δ, MIP-3α, MIP-2, RANTES); other ligands of chemokine receptors (e.g., CCR1, CCR-2, CCR-5, CCR-6, CXCR-1); cytokines (e.g., IL-1β, IL-2, IL-6, IL-8, IL-10, IL-12; IFN-γ; TNF-α; GM-CSF); other ligands of receptors for those cytokines, immunostimulatory CpG motifs in bacterial DNA or oligonucleotides; muramyl dipeptide (MDP) and derivatives thereof (e.g., murabutide, threonyl-MDP, muramyl tripeptide); heat shock proteins and derivatives thereof; Leishmania homologs of eIF4a and derivatives thereof; bacterial ADP-ribosylating exotoxins and derivatives thereof (e.g., genetic mutants, A and/or B subunit-containing fragments, chemically toxoided versions); chemical conjugates or genetic recombinants containing bacterial ADP-ribosylating exotoxins or derivatives thereof; C3d tandem array; lipid A and derivatives thereof (e.g., monophosphoryl or diphosphoryl lipid A, lipid A analogs, AGP, AS02, AS04, DC-Chol, Detox, OM-174); ISCOMS and saponins (e.g., QUIL A, QS-21); squalene; superantigens; or salts (e.g., aluminum hydroxide or phosphate, calcium phosphate). See also Nohria et al. (Biotherapy, 7:261-269, 1994) and Richards et al. (in *Vaccine Design*, Eds. Powell et al., Plenum Press, 1995) for other useful adjuvants.

Adjuvant may be chosen to preferentially induce antibody or cellular effectors, specific antibody isotypes (e.g., IgM, IgD, IgA1, IgA2, secretory IgA, IgE, IgG1, IgG2, IgG3, and/or IgG4), or specific T-cell subsets (e.g., CTL, Th1, Th2 and/or $T_{DTH}$). For example, antigen presenting cells may present Class II-restricted antigen to precursor CD4+ T cells, and the Th1 or Th2 pathway may be entered. T helper cells actively secreting cytokine are primary effector cells; they are memory cells if they are resting. Reactivation of memory cells produces memory effector cells. Th1 characteristically secrete IFN-γ (TNF-β and IL-2 may also be secreted) and are associated with "help" for cellular immunity, while Th2 characteristically secrete IL-4 (IL-5 and IL-13 may also be secreted) and are associated with "help" for humoral immunity. Depending on disease pathology, adjuvants may be chosen to prefer a Th1 response (e.g., antigen-specific cytolytic cells) vs. a Th2 response (e.g., antigen-specific antibodies).

Unmethylated CpG dinucleotides or similar motifs are known to activate B lymphocytes and macrophages (see U.S. Pat. No. 6,218,371). Other forms of bacterial DNA can be used as adjuvants. Bacterial DNA is among a class of structures which have patterns allowing the immune system to recognize their pathogenic origins to stimulate the innate immune response leading to adaptive immune responses. These structures are called pathogen-associated molecular patterns (PAMP) and include lipopolysaccharides, teichoic acids, unmethylated CpG motifs, double-stranded RNA, and mannins. PAMP induce endogenous signals that can mediate the inflammatory response, act as costimulators of T-cell function and control the effector function. The ability of PAMP to induce these responses play a role in their potential as adjuvants and their targets are antigen presenting cells such as dendritic cells and macrophages. The antigen presenting cells of the skin could likewise be stimulated by PAMP transmitted through the skin. For example, Langerhans cells, a type of dendritic cell, could be activated by PAMP in solution on the skin with a transcutaneously poorly immunogenic molecule and be induced to migrate and present this poorly immunogenic molecule to T-cells in the lymph node, inducing an antibody response to the poorly immunogenic molecule. PAMP could also be used in conjunction with other skin adjuvants such as cholera toxin to induce different costimulatory molecules and control different effector functions to guide the immune response, for example from a Th2 to a Th1 response.

Most ADP-ribosylating exotoxins (bARE) are organized as A:B heterodimers with a B subunit containing the receptor binding activity and an A subunit containing the ADP-ribosyltransferase activity. Exemplary bARE include cholera toxin (CT) *E. coli* heat-labile enterotoxin (LT), diphtheria toxin, Pseudomonas exotoxin A (ETA), pertussis toxin (PT), *C. botulinum* toxin C2, *C. botulinum* toxin C3, *C. limosum* exoenzyme, *B. cereus* exoenzyme, *Pseudomonas* exotoxin S, *S. aureus* EDIN, and *B. sphaeticus* toxin. Mutant bARE, for example containing mutations of the trypsin cleavage site (e.g., Dickenson et al., Infect Immun, 63:1617-1623, 1995) or mutations affecting ADP-ribosylation (e.g., Douce et al., Infect Immun, 65:28221-282218, 1997) may be used.

CT, LT, ETA and PT, despite having different cellular binding sites, are potent adjuvants for transcutaneous immunization, inducing IgG antibodies but not IgE antibodies. CTB without CT can also induce IgG antibodies. Thus, both bARE and a derivative thereof can effectively immunize when epicutaneously applied to the skin. Native LT as an adjuvant and antigen, however, is clearly not as potent as native CT. But activated bARE can act as adjuvants for weakly immunogenic antigens in a transcutaneous immunization system. Thus, therapeutic immunization with one or more antigens could be used separately or in conjunction with immunostimulation of the antigen presenting cell to induce a prophylactic or therapeutic immune response.

In general, toxins can be chemically inactivated to form toxoids which are less toxic but remain immunogenic. We envision that the transcutaneous immunization system using toxin-based immunogens and adjuvants can achieve antitoxin levels adequate for protection against these diseases. The anti-toxin antibodies may be induced through immunization with the toxins, or genetically-detoxified toxoids themselves, or with toxoids and adjuvants. Genetically toxoided toxins which have altered ADP-ribosylating exotoxin activity or trypsin cleavage site, but not binding activity, are envisioned to be especially useful as non-toxic activators of antigen presenting cells used in transcutaneous immunization and may reduce concerns over toxin use.

bARE can also act as an adjuvant to induce antigen-specific CTL through transcutaneous immunization. The bARE adjuvant may be chemically conjugated to other antigens including, for example, carbohydrates, polypeptides, glycolipids, and glycoprotein antigens. Chemical conjugation with toxins, their subunits, or toxoids with these antigens would be expected to enhance the immune response to these antigens when applied epicutaneously. To overcome the problem of the toxicity of the toxins (e.g., diphtheria toxin is known to be so toxic that one molecule can kill a cell) and to overcome the problems of working with such potent toxins as tetanus, several workers have taken a recombinant approach to producing genetically-produced toxoids. This is based on inactivating the catalytic activity of the ADP-ribosyl transferase by genetic deletion. These toxins retain the binding capabilities, but lack the toxicity, of the natural toxins. Such genetically toxoided exotoxins would be expected to induce a transcutaneous immune response and to act as adjuvants. They may provide an advantage in a transcutaneous immunization system in that they would not create a safety concern as the toxoids would not be considered toxic. Activation through a technique such as trypsin cleavage, however, would be expected to enhance the adjuvant qualities of LT through the skin which lacks trypsin-like enzymes. Additionally, several techniques exist to chemically modify toxins and can address the same problem. These techniques could be important for certain applications, especially pediatric applications, in which ingested toxins might possibly create adverse reactions.

Adjuvant may be biochemically purified from a natural source (e.g., pCT or pLT) or recombinantly produced (e.g., rCT or rLT). ADP-ribosylating exotoxin may be purified either before or after proteolysis (i.e., activation). B subunit of the ADP-ribosylating exotoxin may also be used: purified from the native enzyme after proteolysis or produced from a fragment of the entire coding region of the enzyme. The subunit of the ADP-ribosylating exotoxin may be used separately (e.g., CTB or LTB) or together (e.g., CTA-LTB, LTA-CTB) by chemical conjugation or genetic fusion.

Point mutations (e.g., single, double, or triple amino acid substitutions), deletions (e.g., protease recognition site), and isolated functional domains of ADP-ribosylating exotoxin may also be used as adjuvant. Derivatives which are less toxic or have lost their ADP-ribosylation activity, but retain their adjuvant activity have been described. Specific mutants of $E.$ $coli$ heat-labile enterotoxin include LT-K63, LT-R72, LT (H44A), LT (R192G), LT (R192G/L211A), and LT ($\Delta$192-194). Toxicity may be assayed with the Y-1 adrenal cell assay (Clements and Finkelstein, Infect Immun, 24:760-769, 1979). ADP-ribosylation may be assayed with the NAD-agmatine ADP-ribosyltransferase assay (Moss et al., J Biol Chem, 268:6383-6387, 1993). Particular ADP-ribosylating exotoxins, derivatives thereof, and processes for their production and characterization are described in U.S. Pat. Nos. 4,666,837; 4,935,364; 5,308,835; 5,785,971; 6,019,982; 6,033,673; and 6,149,919.

An activator of Langerhans cells may also be used as an adjuvant. Examples of such activators include: inducers of heat shock protein; contact sensitizers (e.g., trinitrochlorobenzene, dinitrofluorobenzene, nitrogen mustard, pentadecylcatechol); toxins (e.g., Shiga toxin, Staph enterotoxin B); lipopolysaccharide (LPS), lipid A, or derivatives thereof; bacterial DNA; cytokines (e.g., TNF-$\alpha$, IL-1$\beta$, IL-10, IL-12); members of the TGF$\beta$ superfamily, calcium ions in solution, calcium ionophores, and chemokines (e.g., defensins 1 or 2, RANTES, MIP-1$\alpha$, MIP-2, IL-8).

If an immunizing antigen has sufficient Langerhans cell activating capabilities then a separate adjuvant may not be required, as in the case of LT which is both antigen and adjuvant. Alternatively, such antigens can be considered not to require an adjuvant because they are sufficiently immunogenic. It is envisioned that live cell or virus preparations, attenuated live cells or viruses, killed cells, inactivated viruses, and DNA plasmids could be effectively used for transcutaneous immunization. It may also be possible to use low concentrations of contact sensitizers or other activators of Langerhans cells to induce an immune response without inducing skin lesions.

Other techniques for enhancing activity of adjuvants may be effective, such as adding surfactants and/or phospholipids to the formulation to enhance adjuvant activity of ADP-ribosylating exotoxin by ADP-ribosylation factor. One or more ADP-ribosylation factors (ARF) may be used to enhance the adjuvanticity of bARE (e.g., ARF1, ARF2, ARF3, ARF4, ARF5, ARF6, ARD1). Similarly, one or more ARF could be used with an ADP-ribosylating exotoxin to enhance its adjuvant activity.

Undesirable properties or harmful side effects (e.g., allergic or hypersensitive reaction; atopy, contact dermatitis, or eczema; systemic toxicity) may be reduced by modification without destroying its effectiveness in transcutaneous immunization. Modification may involve, for example, removal of a reversible chemical modification (e.g., proteolysis) or encapsulation in a coating which reversibly isolates one or more components of the formulation from the immune system. For example, one or more components of the formulation may be encapsulated in a particle for delivery (e.g., microspheres, nanoparticles) although we have shown that encapsulation in lipid vesicles is not required for transcutaneous immunization and appears to have a negative effect. Phagocytosis of a particle may, by itself, enhance activation of an antigen presenting cell by upregulating expression of MHC Class I and/or Class II molecules and/or costimulatory molecules (e.g., CD40, B7 family members like CD80 and CD86).

Formulation

Processes for manufacturing a pharmaceutical formulation are well known. The components of the formulation may be combined with a pharmaceutically-acceptable carrier or vehicle, as well as any combination of optional additives (e.g., at least one diluent, binder, excipient, stabilizer, dessicant, preservative, coloring, or combinations thereof. See, generally, *Ullmann's Encyclopedia of Industrial Chemistry*, $6^{th}$ Ed. (electronic edition, 1998); *Remington's Pharmaceutical Sciences*, $22^{nd}$ (Gennaro, 1990, Mack Publishing); *Pharmaceutical Dosage Forms*, $2^{nd}$ Ed. (various editors, 1989-1998, Marcel Dekker); and *Pharmaceutical Dosage Forms and Drug Delivery Systems* (Ansel et al., 1994, Williams & Wilkins).

Good manufacturing practices are known in the pharmaceutical industry and regulated by government agencies (e.g., Food and Drug Administration). Sterile liquid formulations may be prepared by dissolving an intended component of the formulation in a sufficient amount of an appropriate solvent, followed by sterilization by filtration to remove contaminating microbes. Generally, dispersions are prepared by incorporating the various sterilized components of the formulation into a sterile vehicle which contains the basic dispersion medium. For production of solid forms that are required to be sterile, vacuum drying or freeze drying can be used. Solid dosage forms (e.g., powders, granules, pellets, tablets) or liquid dosage forms (e.g., liquid in ampules, capsules, vials) can be made from at least one active ingredient or component of the formulation.

Suitable procedures for making the various dosage forms and production of patches are known. The formulation may also be produced by encapsulating solid or liquid forms of at least one active ingredient or component, or keeping them separate in compartments or chambers. The patch may include a compartment containing a vehicle (e.g., a saline solution) which is disrupted by pressure and subsequently solubilizes the dry formulation of the patch. The size of each dose and the interval of dosing to the subject may be used to determine a suitable size and shape of the container, compartment, or chamber.

Formulations will contain an effective amount of the active ingredients (e.g., antigen and adjuvant) together with carrier or suitable amounts of vehicle in order to provide pharmaceutically-acceptable compositions suitable for administration to a human or animal. Formulation that include a vehicle may be in the form of an cream, emulsion, gel, lotion, ointment, paste, solution, suspension, or other liquid forms known in the art; especially those that enhance skin hydration.

The relative amounts of active ingredients within a dose and the dosing schedule may be adjusted appropriately for efficacious administration to a subject (e.g., animal or human). This adjustment may depend on the subject's particular disease or condition, and whether therapy or prophylaxis is intended. To simplify administration of the formulation to the subject, each unit dose would contain the active ingredients in predetermined amounts for a single round of immunization.

There are numerous causes of protein instability or degradation, including hydrolysis and denaturation. In the case of denaturation, the protein's conformation is disturbed and the protein may unfold from its usual globular structure. Rather than refolding to its natural conformation, hydrophobic interaction may cause clumping of molecules together (i.e., aggregation) or refolding to an unnatural conformation. Either of these results may entail diminution or loss of antigenic or adjuvant activity. Stabilizers may be added to lessen or prevent such problems.

The formulation, or any intermediate in its production, may be pretreated with protective agents (i.e., cryoprotectants and dry stabilizers) and then subjected to cooling rates and final temperatures that minimize ice crystal formation. By proper selection of cryoprotective agents and the use of preselected drying parameters, almost any formulation might be cryoprepared for a suitable desired end use.

It should be understood in the following discussion of optional additives like excipients, stabilizers, dessicants, and preservatives are described by their function. Thus, a particular chemical may act as some combination of excipient, stabilizer, dessicant, and/or preservative. Such chemicals would be considered immunologically-inactive because it does not directly induce an immune response, but it increases the response by enhancing immunological activity of the antigen or adjuvant: for example, by reducing modification of the antigen or adjuvant, or denaturation during drying and dissolving cycles.

Stabilizers include cyclodextrin and derivatives thereof (see U.S. Pat. No. 5,730,969). Suitable preservatives such as sucrose, mannitol, sorbitol, trehalose, dextran, and glycerin can also be added to stabilize the final formulation. A stabilizer selected from nonionic surfactants, D-glucose, D-galactose, D-xylose, D-glucuronic acid, salts of D-glucuronic acid, trehalose, dextrans, hydroxyethyl starches, and mixtures thereof may be added to the formulation. Addition of an alkali metal salt or magnesium chloride may stabilize a polypeptide, optionally including serum albumin and freeze-drying to further enhance stability. A polypeptide may also be stabilized by contacting it with a saccharide selected from the group consisting of dextran, chondroitin sulfuric acid, starch, glycogen, insulin, dextrin, and alginic acid salt. Other sugars that can be added include monosaccharides, disaccharides, sugar alcohols, and mixtures thereof (e.g., glucose, mannose, galactose, fructose, sucrose, maltose, lactose, mannitol, xylitol). Polyols may stabilize a polypeptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize polpeptides, including serum albumin, amino acids, heparin, fatty acids and phospholipids, surfactants, metals, polyols, reducing agents, metal chelating agents, polyvinyl pyrrolidone, hydrolyzed gelatin, and ammonium sulfate.

Single-dose formulations can be stabilized in poly(lactic acid) (PLA) and poly (lactide-co-glycolide) (PLGA) microspheres by suitable choice of excipient or stabilizer. Trehalose may be advantageously used as an additive because it is a non-reducing saccharide, and therefore does not cause aminocarbonyl reactions with substances bearing amino groups such as proteins.

It is conceivable that a formulation that can be administered to the subject in a dry, non-liquid form, may allow storage in conditions that do not require a cold chain. An antigen (e.g., CS6) in solution may be mixed in solution with an adjuvant such as LT and is placed on a gauze pad with an occlusive backing such as plastic wrap and allowed to dry. This patch can then be placed on skin with the gauze side in direct contact with the skin for a period of time and can be held in place covered with a simple occlusive such as plastic wrap and adhesive tape. The patch may have many compositions. The substrate may be cotton gauze, combinations of rayon-nylon or other synthetic materials and may have occlusive solid backings including polyvinyl chloride, rayons, other plastics, gels, creams, emulsions, waxes, oils, parafilm, rubbers (synthetic or natural), cloths, or membranes. The patch can be held onto the skin and components of the patch can be held together using various adhesives. One or more of the adjuvant and/or antigen may be incorporated into the substrate or adhesive parts of the patch.

A liquid or quasi-liquid formulation may be applied directly to the skin and allowed to air dry; rubbed into the skin or scalp; placed on the ear, inguinal, or intertriginous regions, especially in animals; placed on the anal/rectal tissues; held in place with a dressing, patch, or absorbent material; immersion; otherwise held by a device such as a stocking, slipper, glove, or shirt; or sprayed onto the skin to maximize contact with the skin. The formulation may be applied in an absorbent dressing or gauze. The formulation may be covered with an occlusive dressing such as, for example, AQUAPHOR (an emulsion of petrolatum, mineral oil, mineral wax, wool wax, panthenol, bisabol, and glycerin from Beiersdorf), plastic film, COMFEEL (Coloplast) or VASELINE petroleum jelly; or a non-occlusive dressing such as, for example, TEGADERM (3M), DUODERM (3M) or OPSITE (Smith & Napheu). An occlusive dressing excludes the passage of water. Such a formulation may be applied to single or multiple sites, to single or multiple limbs, or to large surface areas of the skin by complete immersion. The formulation may be applied directly to the skin. Other substrates that may be used are pressure-sensitive adhesives such as acrylics, polyisobutylenes, and silicones. The formulation may be incorporated directly into such substrates, perhaps with the adhesive per se instead of adsorption to a porous pad (e.g., gauze) or bilious strip (e.g., filter paper).

Whether or not a patch is used, polymers added to the formulation may act as an excipient, stabilizer, and/or preservative of an active ingredient as well as reducing the concentration of the active ingredient that saturates a solution used to dissolve a dry form of the active ingredient. Such reduction occurs because the polymer reduces the effective volume of the solution by filling the "empty" space. In this way, quantities of antigen/adjuvant can be conserved without reducing the amount of saturated solution. An important thermodynamic consideration is that an active ingredient in the saturated solution will be "driven" into regions of lower concentration (e.g., through the skin). In solution, polymers can also stabilize and/or preserve the antigen/adjuvant-activity of solubilized ingredients of the formulation. Such polymers include ethylene or propylene glycol, vinyl pyrrolidone, and β-cyclodextrin polymers and copolymers.

Transcutaneous Delivery

Transcutaneous delivery of the formulation may target Langerhans cells and, thus, achieve effective and efficient immunization. These cells are found in abundance in the skin and are efficient antigen presenting cells (APC), which can lead to T-cell memory and potent immune responses. Because of the presence of large numbers of Langerhans cells in the skin, the efficiency of transcutaneous delivery may be related to the surface area exposed to antigen and adjuvant. In fact, the reason that transcutaneous immunization is so efficient may be that it targets a larger number of these efficient antigen presenting cells than intramuscular immunization.

The invention will enhance access to immunization, while inducing a potent immune response. Because transcutaneous immunization does not require injection with a hypodermic needle (i.e., penetration to or through the dermis) and the complications and difficulties thereof, the requirements of medically-sophisticated personnel, sterile technique, and sterile equipment are reduced. Furthermore, the barriers to immunization at multiple sites or to multiple immunizations are diminished. Immunization by a single application of the formulation is also envisioned.

Immunization may be achieved using topical or epicutaneous application of a simple formulation of antigen and adjuvant, optionally covered by an occlusive dressing or using other patch technologies, to intact skin with or without chemical or physical penetration. The immunization could be given by untrained personnel, and is amenable to self-application. Large-scale field immunization could occur given the easy accessibility to immunization. Additionally, a simple immunization procedure would improve access to immunization by pediatric, elderly, and Third World populations. Transcutaneous immunization according to the invention may provide a method whereby antigens and adjuvant can be delivered to the immune system, especially specialized antigen presentation cells underlying the skin (e.g., Langerhans cells).

For traditional vaccines, their formulations were injected through the skin with needles. Injection of vaccines using needles carries certain drawbacks including the need for sterile needles and syringes, trained medical personnel to administer the vaccine, discomfort from the injection, needle-born diseases, and potential complications brought about by puncturing the skin with the potentially reusable needles. Immunization through the skin without the use of hypodermic needles represents an advance for vaccine delivery by avoiding the hypodermic needles.

Moreover, transcutaneous immunization may be superior to immunization using hypodermic needles as more immune cells would be targeted by the use of several locations targeting large surface areas of skin. A therapeutically-effective amount of antigen sufficient to induce an immune response may be delivered transcutaneously either at a single cutaneous location, or over an area of skin covering multiple draining lymph node fields (e.g., cervical, axillary, inguinal, epitrochelear, popliteal, those of the abdomen and thorax). Such locations close to numerous different lymphatic nodes at locations all over the body will provide a more widespread stimulus to the immune system than when a small amount of antigen is injected at a single location by intradermal, subcutaneous, or intramuscular injection.

Antigen passing through or into the skin may encounter antigen presenting cells which process the antigen in a way that induces an immune response. Multiple immunization sites may recruit a greater number of antigen presenting cells and the larger population of antigen presenting cells that were recruited would result in greater induction of the immune response. It is conceivable that use of the skin may deliver antigen to phagocytic cells of the skin such as, for example, dendritic cells, Langerhans cells, macrophages, and other skin antigen presenting cells; antigen may also be delivered to phagocytic cells of the liver, spleen, and bone marrow that are known to serve as the antigen presenting cells through the blood stream or lymphatic system.

Langerhans cells, other dendritic cells, macrophages, or combinations thereof may be specifically targeted using their asialoglycoprotein receptor, mannose receptor, Fcγ receptor CD64, high-affinity receptor for IgE, or other highly expressed membrane proteins. A ligand or antibody specific for any of those receptors may be conjugated to or recombinantly produced as a protein fusion with adjuvant, antigen, or both. Furthermore, adjuvant, antigen, or both may be conjugated to or recombinantly produced as a protein fusion with protein A or protein G to target surface immunoglobulin of B lymphocytes. The envisioned result would be widespread distribution of antigen to antigen presenting cells to a degree that is rarely, if ever achieved, by current immunization practices.

Genetic immunization has been described in U.S. Pat. Nos. 5,589,466, 5,593,972, and 5,703,055. The nucleic acid(s) contained in the formulation may encode the antigen, the adjuvant, or both. The nucleic acid may or may not be capable of replication; it may be non-integrating and non-infectious. For example, the nucleic acid may encode a fusion polypeptide comprising antigen and a ubiquitin domain to direct the immune response to a class I restricted response. The nucleic acid may further comprise a regulatory region operably linked to the sequence encoding the antigen or adjuvant. The nucleic acid may be added with an adjuvant. The nucleic acid may be complexed with an agent that promotes transfection such as cationic lipid, calcium phosphate, DEAE-dextran, polybrene-DMSO, or a combination thereof. Immune cells can be targeted by conjugation of DNA to Fc receptor or protein A/G, or attaching DNA to an agent linking it to $\alpha_2$-macroglobulin or protein A/G or similar APC targeting material.

A specific immune response may comprise humoral (i.e., antigen-specific antibody) and/or cellular (i.e., antigen-specific lymphocytes such as B lymphocytes, CD4$^+$T cells, CD8$^+$T cells, CTL, Th1 cells, Th2 cells, and/or $T_{DTH}$ cells) effector arms. Moreover, the immune response may comprise NK cells and other leukocytes that mediate antibody-dependent cell-mediated cytotoxicity (ADCC).

The immune response induced by the formulation of the invention may include the elicitation of antigen-specific antibodies and/or lymphocytes. Antibody can be detected by immunoassay techniques. Detection of the various antibody isotypes (e.g., IgM, IgD, IgA1, IgA2, secretory IgA, IgE, IgG1, IgG2, IgG3, or IgG4) can be indicative of a systemic or regional immune response. Immune responses can also be detected by a neutralizing assay. Antibodies are protective proteins produced by B lymphocytes. They are highly specific, generally targeting one epitope of an antigen. Often, antibodies play a role in protection against disease by specifically reacting with antigens derived from the pathogens causing the disease. Immunization may induce antibodies specific for the immunizing antigen (e.g., bacterial toxin).

CTL are immune cells produced to protect against infection by a pathogen. They are also highly specific. Immunization may induce CTL specific for the antigen, such as a synthetic oligopeptide based on a malaria protein, in association with self-major histocompatibility antigen. CTL induced by immunization with the transcutaneous delivery system may kill pathogen-infected cells. Immunization may also produce a memory response as indicated by boosting responses in antibodies and CTL, lymphocyte proliferation by culture of lymphocytes stimulated with the antigen, and delayed type hypersensitivity responses to intradermal skin challenge of the antigen alone.

Successful protection could also be demonstrated by challenge studies using infection by the pathogen or administration of toxin, or measurement of a clinical criterion (e.g., high antibody titers or production of IgA antibody-secreting cells in mucosal membranes may be used as a surrogate marker).

The following is meant to be illustrative of the invention, but practice of the invention is not limited or restricted in any way by the following examples.

ANIMAL EXAMPLES

BALB/c and C57BL/6 mice were obtained from Jackson Laboratories. Mice (6-10 wks of age) were maintained in pathogen-free conditions and fed rodent chow and water ad libitum. Female Hartley guinea pigs, 4-6 weeks of age, were procured from Charles River Laboratories, and maintained in pathogen-free conditions receiving food and water ad libitum.

Cholera toxin (CT) was purchased from List Biologicals. E. coli heat labile enterotoxin (LT) was purchased from Swiss Serum and Vaccine Institute (SSVI).

To prepare recombinant CS6 (rCS6), the complete four-gene operon for CS6 (approximately 5 kb) was cloned into E. coli strain HB101 (Wolf et al., 1997; Wolf et al., 1997) on a pUC19 derivatized plasmid containing a kanamycin resistance gene. rCS6 was produced using this clone in a New Brunswick BioFlo 3000 fermentor. The fermentation broth was harvested by centrifugation, and the rCS6 purified by tangential flow filtration followed by precipitation in ammonium sulfate (Wolf et al., 1997). The rCS6 was then buffer exchanged with phosphate buffered saline (PBS). This purified rCS6 was stored at −30° C. until immunization. The purity of rCS6 was determined as >98% by sodium dodecyl sulfate-polyacrylamide gel electrophoresis (SDS-PAGE), Coomassie blue staining, and densitometric scanning (Cassels et al., 1992; Schagger & von Jagow, 1987).

Clinical ETEC strains E8775 and E9034A were utilized as the sources for native CS6 (nCS6) and CS3, respectively. Heat and saline extracts of the two strains grown on CFA agar (Evans et al., 1977) were treated with ammonium sulfate sequentially at 10% saturation intervals (Wolf et a., 1997). The precipitate at 60% and 30% saturation contained the greatest quantity and highest purity of native CS6 and native CS3, respectively, as determined by SDS-PAGE and ELISA assay.

P. falciparum MSP (MSP-$1_{42}$, 3D7) was expressed in E. coli BL21 (DE3) with a polyhistidine tag (Novagen). Antigen was purified to near homogeneity using three chromatographic steps: nickel affinity, Q anion exchange, and CM cation exchange.

Mice were transcutaneously immunized as described previously (Scharton-Kersten et al., 2000). Briefly, the animals were shaved on the dorsum with a No. 40 clipper, which leaves no visible irritation or changes in the skin, and rested for 48 hr. Mice and guinea pigs were anesthetized in the hind thigh intramuscularly (IM) or intraperitoneally (IP) with a ketamine/xylazine mixture during the immunization procedure to prevent self-grooming. The exposed skin surface was hydrated with water-drenched gauze for 5-10 min, and lightly blotted with dry gauze prior to immunization. Twenty-five to 100 µl of immunizing solution was placed on the shaved skin over a 2-cm² area for one hour. The animals were then extensively washed, tails down, under running tap water for approximately 30 sec, patted dry, and washed again.

Passive immunization was accomplished by tail vein injection of pooled hyper-immune serum from a matched strain of mice containing an anti-LT IgG titer greater than 10,000 ELISA units. Naïve BALB/c mice were injected with 0.5 ml of serum one hour before oral challenge with LT or bicarbonate buffer. Naïve C57BL/6 mice were also passively immunized using the same procedure 12 hr before challenge.

An exotoxin challenge model has been described (Richardson et al, 1984). BALB/c mice were fed LT (10 µg in 500 µl) suspended in 10% sodium bicarbonate ($NaHCO_3$) solution. C57BL/6 mice were fed LT (100 pg per gram weight in 500 µl of 10% $NaHCO_3$) based on body weight. Control animals received 500 µl of 10% $NaHCO_3$ alone. To prevent coprophagy, the mice were transferred to cages with wire mesh flooring. Mice were given 10% glucose water but no food for 12 hr before challenge and during challenge. Six hours after the challenge, the animals were weighed and sacrificed. The small intestines were then dissected (pyloric valve to ileal-cecal junction), tied off to prevent fluid loss, and weighed. Fluid accumulation was calculated using the formula: $FA=(G/(B-G))*1000$, where G=gut weight+fluid in grams and B=body weight in grams. Using this formula, baseline fluid accumulation in untreated or bicarbonate fed animals is 30 to 150, depending upon the initial body weight of the animal.

Histopathological studies were performed by Gary M. Zaucha, AVP, ABT, and ACVPM of the Comparative Pathology Division at the Walter Reed Army Institute of Research. Two guinea pigs per treatment group and one control animal were designated for pathology. Animals were euthanized on day two post-exposure for each of the three vaccinations and subject to a complete gross necropsy. Histopathologic examination of the high dose group included examination of a full complement of tissues with skin (haired skin and the dorsal lumbar exposure site) and liver evaluated in the remaining groups. Tissues collected and formalin fixed in the high dose group were brain, pituitary, tongue, lung, trachea, esophagus, thyroid, thymus, heart, pancreas, spleen, liver (with associated gallbladder), stomach, small intestine, cecum, colon, mesenteric lymph node, kidney, adrenal, urinary bladder, ovary, uterus, salivary glands, submandibular lymph node, bone marrow (sternum), haired skin, dorsal lumbar exposure site, and gross lesions. Histopathologic findings for individual animals were graded on a scale of 1 to 5 (1=minimal, 2=mild, 3=moderate, 4=marked, and 5=severe).

Antibody levels against CT, LT, native CS3, native CS6, rCS6 and MSP-$1_{42}$ were determined by ELISA. Immulon-2 polystyrene plates (Dynex Laboratories) were coated with 0.1 µg/well of antigen, incubated at room temperature overnight, blocked with a 0.5% casein buffer in PBS, washed, serial dilutions of specimen applied, and the plates incubated for 2 hr at room temperature. IgG (H+L) antibody was detected using HRP-linked goat anti-mouse IgG (H+L) (Biorad) for 1 hr. Anti-LT specific IgA levels were determined as above with HRP-linked goat anti-mouse IgA (Zymed) substituted as the secondary antibody. Secretory IgA (S-IgA) antibody levels were also measured by ELISA, wherein LT coated plates were sequentially incubated with stool, lung wash, or vaginal wash from naive and immunized animals, purified rabbit anti-secretory chain (SC) antibody (16-24 hr at 4° C.) (Crottet et al., 1999), and peroxidase-labeled goat anti-rabbit IgG (H+L) (Kirkegaard and Perry) for 2 hr at room temperature.

Bound antibody was revealed using 2,2'-azino-di (3-ethylbenzthiazoline sulphonic acid) substrate (ABTS; Kirkegaard and Perry) and the reaction stopped after 30 min using a 1% SDS solution. Plates were read at 405 nm. Antibody titer results are reported in either OD (405 nm) or ELISA Units, which are defined as the inverse dilution of the sera that yields an optical density (OD) of 1.0. Guinea pig anti-rCS6 ELISAs were conducted as above with peroxidase-conjugated goat anti-guinea pig IgG (Jackson ImmunoResearch) included in the detection step. Anti-SC secondary antibody reacted with antigen coated (rCS6) plates, resulting in high background, which rendered this assay unsuitable for anti-rCS6 SC detection.

One microliter of rCS6 (0.5 µg), native CS6 (1.6 µg) and native CS3 (0.5 µg) were spotted onto nitrocellulose strips (Schleicher and Schuell), and dried overnight. Strips were blocked by incubation in PBS with 0.05% Tween 20 (PBS-T, Sigma) and 1% bovine serum albumin for 2 hr. Primary mouse antibody was diluted to 1:1000 and 1:4000 and incubated with the strips for 1 hr, followed by three washes of 1, 5, and 10 min, all in PBS-T. Strips were then incubated in goat anti-mouse IgG labeled with horseradish peroxidase (1:5000 in PBS-T, 30 min). After washing in PBS three times for 10 min each, the strips were developed with 3,3' diaminobenzidine (DAB, Sigma), hydrogen peroxide (Sigma), and cobalt chloride (Mallinckrodt), as described in Harlow & Lane (1988). All incubations and washes took place on an orbital shaker at room temperature.

Seven days after the last immunization, mononuclear cells were isolated from the spleen and superficial ventral cervical nodes and washed in RPMI 1640 with 50 mg of gentamycin per ml prior to use in the ELISPOT assay as previously described (Hartman et al., 1994; Hartman et al., 1999). Washed spleen and lymph node cells were counted and diluted in culture medium (RPMI 1640 with 2 mM glutamine, 50 mg of gentamycin per ml, and 10% fetal bovine serum) to a density of $2.5 \times 10^6$/ml. One hundred ml of the cell suspension were inoculated into microwells previously coated with 0.1 µg/well of CS6 antigen in carbonate coating buffer, pH 9.6, or coating buffer alone. Each sample was assayed in quadruplicate. After incubation at 37° C. for 4 hr, plates were washed and rabbit anti-guinea pig IgG (1:1200), IgA (1:700), or IgM (1:800) (ICN Laboratories) was added. After overnight incubation at 4° C., plates were washed and alkaline phosphatase-conjugated goat anti-rabbit anti-sera (Sigma) at a dilution of 1:1200 was added. After 2 hr at 37° C., plates were washed and spots were visualized by the addition of 100 ml of molten agarose containing 100 mg of 5-bromo-4-chloro-3-indolyl phosphate per ml. Spot-forming cells were then counted with a stereomicroscope.

Blood contamination was not apparent upon visual inspection of freshly collected murine stool, lung wash or vaginal wash specimen. Further testing with HEMASTIX strips (Bayer) indicated that blood contamination was ≦5-20 intact red blood cells per µl or ≦0.015-0.062 mg free hemoglobin per dL.

Stool pellets were collected the day before challenge by spontaneous defecation, weighed, homogenized in 1 ml of PBS per 100 mg of fecal material, centrifuged, and the supernatant collected and stored at −20° C.

Mice were exsanguinated, the trachea transected, 22-gauge polypropylene tubing inserted, and PBS gently infused to inflate the lungs. The infused material was then withdrawn, re-infused for a total of three cycles, and stored at −20° C.

The vaginal cavity was gently lavaged by repeated insertion and aspiration of PBS (80 µl) into the vaginal cavity for a total of three cycles. The vaginal material was spun for 10 min at 3,000 rpm and the supernatant transferred to a clean container and stored at −20° C.

BALB/c mice were immunized on the skin with MSP1 alone or CT and MSP1 at 0, 4, 8 and 12 weeks. Spleen and draining lymph node (inguinal) tissues were removed 24 weeks after the primary immunization. Single cell suspensions were prepared from spleen tissue from individual mice or from LNs pooled within each group. Cells were cultured at $4 \times 10^5$ per well in 96-well plates for 5 days at 37° C., 5% $CO_2$ in the presence or absence of 10 µg/ml of MSP1 antigen. Concanavalin A (ConA) at 5 µg/ml was used as a positive control. Culture media contained RPMI 1640 (BioWhittaker) supplemented with 10% fetal calf serum (Gibco), penicillin (10 U/ml, BioWhittaker), streptomycin (100 µg/ml, BioWhittaker), L-glutamine (2 mM, Sigma), and Hepes (10 µM, Bio-Rad). [$^3$H]-thymidine (1 µCi/well) was added to the cultures during the last 20 hr of the 5-day culture period. Thymidine incorporation was assessed by harvesting cellular DNA onto glass fiber filters, followed by liquid scintillation counting.

$CD4^+$T cells were isolated from pooled spleen cells from the CT/MSP1 immunization group using a $CD4^+$T cell selection column and the manufacturer's instructions (R&D Systems). Cells eluted from the column ($CD4^+$) were cultured in 96-well plates at $1 \times 10^5$ cells per well in the presence or absence of $3 \times 10^5$ irradiated (3000 rad) feeder cells from naïve mice. Proliferation assays were conducted in the presence or absence of antigen stimulation as described above.

Unless otherwise indicated, the ELISA data shown are the geometric mean of values from individual animals, and error bars represent two standard deviations from the mean. Comparisons between antibody titers and fluid accumulation (FA) in groups were performed using an unpaired, two-tailed Student's t test and p values <0.05 regarded as significant.

Immunization on the skin with bacterial adjuvant and the colonization factor CS6 results in a protective antibody response. To determine if TCI would be an effective method for inducing relevant ETEC immune responses, mice were immunized four times by TCI with CT and rCS6, assayed for anti-CS6 responses, subsequently challenged orally with CT holotoxin, and the degree of acute intestinal swelling (fluid accumulation) quantified 6 hr later. A positive control group was immunized by the intramuscular route (IM) with 5 µg of rCS6 in alum, and a negative control group received rCS6 alone on the skin. Antibodies reacting with rCS6 antigen were apparent after the first immunization in animals receiving either a low (10 µg) or high (100 µg) dose of adjuvant, and the titers continued to rise after the $1^{st}$ and $2^{nd}$ booster immunizations. The immune response to CS6 in the presence of adjuvant (10 or 100 µg) was greater (p<0.05) than the response seen to antigen alone delivered by TCI at 12 weeks. The geometric mean anti-CS6 titers were greatest in the high dose (CT 100 µg) group following the third immunization, and a higher geometric mean anti-CS6 titer was produced using TCI compared to intramuscular immunization, but neither difference was statistically significant. Anti-CT titers were elevated in both of the CT adjuvanted groups at all time points. Animals immunized with CS6 alone on the skin failed to develop a consistent antibody response to the antigen or the adjuvant.

Naïve, antigen alone, and CT+CS6 (100 µg/100 µg) on the skin groups were selected for oral challenge with CT after immunization using TCI. The CS6 alone and CT/CS6 groups were boosted 11 weeks after the $3^{rd}$ immunization (19-week study point). Two weeks later, the animals were fed either bicarbonate buffer alone (10% $NaHCO_3$) or bicarbonate buffer containing 10 µg of CT, and the resulting intestinal swelling was determined. The intestines from naïve mice fed bicarbonate alone had a baseline fluid accumulation of 103 (range 78 to 146). Oral administration of CT in naïve mice resulted in a two-fold increase in fluid accumulation (mean 209; range 164 to 359). Similarly, mice vaccinated with rCS6 alone and subsequently fed CT also displayed an approximate two-fold increase in fluid accumulation (mean 192; range 119 to 294). In contrast, mice vaccinated with CT by TCI developed negligible intestinal swelling following challenge (mean 105; range 84 to 120), and the fluid response was indistinguishable from that observed in the naïve group fed bicarbonate buffer alone (p<0.5).

Comparable adjuvant effects of CT and LT for transcutaneously administered CS6 antigen. Use of LT as an adjuvant for an ETEC vaccine may be desirable, as LT is the causative agent in a significant number of cases of ETEC diarrhea (Wolf et al., 1993), and thus can function both as antigen and adjuvant. To test the relative potencies of CT and LT adjuvants for rCS6, mice were immunized on the skin three times at 4-week intervals with 100 µg of rCS6 and a range of doses of CT or LT (10, 20, and 100 µg). The resulting serum anti-rCS6 and adjuvant titers were assessed two weeks after the final immunization. As expected, anti-adjuvant (CT or LT) IgG titers were apparent at all adjuvant doses, and the titers were higher and most consistent among the high (100 µg) dose animals. In contrast, while all of the CS6 and LT/CT groups developed elevated anti-CS6 titers, the responses were greatest at the lowest LT doses (10 µg vs. 100 µg), and generally comparable to previous experience by the IM route.

Serum antibodies from mice immunized with rCS6 and LT recognize native CS6. Mice immunized with rCS6 produced a high titer of serum IgG that reacted with the recombinant protein used in the ELISA assay. While these results suggested that TCI might be effective in attenuating ETEC infection and disease, it was important to determine if the induced antibodies reacted with the native CS6 (nCS6) present on *E. coli* isolates. To test the specificity of the anti-CS6 response, sera from rCS6-immunized mice were analyzed for reactivity to native CS6 protein in ELISA and immunodot blot assays. In the ELISA, each of the three samples with reactivity to rCS6 and LT demonstrated specificity for native CS6 protein, but not for native CS3 protein. Similarly, by immunodot blot assay, mice immunized with rCS6 and LT reacted with both the immunizing rCS6 antigen and partially purified native CS6, with little or no reaction by preimmune sera. None of the mouse sera reacted with the native CS3 antigen control. Serum from a mouse that was parenterally immunized (IM injection) with rCS6 responded in a similar way to both native CS6 and rCS6 as did sera from transcutaneously immunized mice. In addition the BALB/c mouse responded in a similar fashion as did the C57BL/6 mice. Thus, TCI using rCS6 induced serum antibody capable of recognizing native antigen.

Antibodies to LT actively and passively protect mice from oral challenge with LT. Although LT, the causative agent in LT-mediated ETEC disease, is very similar to CT and shows cross-protection with cholera toxin B subunit (CTB) antibodies (Clemens et al., 1988), direct protection against LT oral challenge using LT antibodies has not been previously shown. Mice immunized with LT and rCS6 by TCI were orally challenged with LT as described. High levels of anti-LT IgG were detected in the sera of immunized mice (geometric mean for BALB/c=36,249 ELISA units; C57BL/6=54,792 ELISA units). For oral toxin challenge, two strains of mice with different sensitivities to challenge were used. C57BL/6 mice are highly sensitive to the effects of LT toxin challenge compared to BALB/c, and protection in both strains suggests the protective effect might be observed in more genetically diverse settings. Significant protection against LT challenge was seen in both strains (p<0.05).

Studies of dog and human ETEC disease suggest that serum antibody contributes to protection against diarrhea from intact bacteria as well as isolated toxin (Pierce et al., 1980; Pierce et al., 1972; Pierce & Reynolds, 1974). Consistent with this premise, we, and others, have previously reported that a transcutaneously elicited serum factor protects animals from a lethal intranasal challenge with CT (Beignon et al., 2001; Glenn et al., 1998b). Thus, we postulated that a serum factor, presumed to be antitoxin antibody, might also contribute to the prevention of toxin-induced intestinal swelling in transcutaneously immunized mice. The host-protective role of antitoxin antibody serum was evaluated by quantitating the intestinal swelling elicited by oral toxin challenge of naïve and passively immunized mice that received serum from animals which were treated by TCI. The effect of passive immunization was evaluated in both BALB/c and C57BL/6 mouse strains. Oral administration of LT to naïve mice consistently induced fluid accumulation that was apparent upon visual inspection. In contrast, passively immunized mice developed negligible fluid accumulation of a magnitude comparable to that observed in the groups fed buffer alone. Thus, the passively immunized mice given antibody from transcutaneously immunized mice were protected from the sequelae of oral toxin challenge. Together, these results indicate that transcutaneously immunized mice produce serum antibodies capable of protecting animals from toxin exposure.

Mucosal IgG, IgA and secretory IgA responses specific for ETEC antigen following TCI. While serum IgG responses are associated with host protection against many infectious agents, mucosal immune responses are considered to be important for attenuation and prevention of mucosally acquired pathogens, particularly intestinal pathogens, such as ETEC. To determine if TCI with rCS6 induces mucosally detectable antibody responses, IgG and S-IgA responses were analyzed in fecal, lung and vaginal specimens harvested from mice immunized on the skin with rCS6 and adjuvant. C57BL/6 mice were immunized three times with CS6 alone, LT/CS6, or CT/CS6. CS6-specific IgG was evaluated in fecal, lung and vaginal wash specimen collected nine weeks after the $3^{rd}$ immunization. Immunization with rCS6 alone failed to induce elevated CS6-specific IgG in either fecal, lung or vaginal wash specimen. In contrast, 3 of 3 animals in the CT/CS6 group contained detectable anti-CS6 IgG in both lung and vaginal wash specimens. Similarly, CS6 specific IgG antibody was observed in lung and vaginal specimen from the LT adjuvanted group and in fecal specimen from CT and LT adjuvanted groups, although the responses were less consistent. The method of collection with fecal samples may have hampered the consistency of fecal antibody results, especially if the responses were modest, and other collection methods are being investigated.

Locally produced IgA is typically a dimeric protein associated with secretory chain (SC) that allows transport across the epithelial membranes. To determine if TCI could induce secretory IgA (S-IgA) production, animals were immunized twice on the skin with LT and the antigen-specific IgG, IgA and S-IgA titers evaluated in mucosal specimen by ELISA. As compared to specimen from naïve animals, immunization with LT induced antigen-specific IgG and IgA in the fecal and vaginal specimen of 10 of 10 immunized mice. More importantly, S-IgA was readily detected in all 10 fecal and vaginal specimens tested.

Induction of protective antitoxin immunity following co-administration of CT and a malarial vaccine antigen. Targeted vaccination against multiple infectious agents is desirable in developing countries where relatively low life expectancies and high morbidity and mortality rates are associated with infection of individuals with more than one pathogen. To determine whether TCI might be employed for inducing protection against multiple unrelated infectious agents, mice were simultaneously vaccinated with CT and a C-terminal 42 kDa fragment of a *Plasmodium falciparum* protein, merozoite surface protein 1 (MSP-$1_{42}$). CT (0, 10 or 100 µg) and MSP (100 µg) proteins were applied to the skin at 0, 4, 8, and 13 weeks. Mice were considered responsive to MSP if the post-immunization titer was 3-fold the OD measured in the pre-immunization serum at a 1:100 dilution. Based on this criterion, MSP antibodies were detected in serum from mice immunized with CT and MSP together but not in serum collected from the control group (MSP alone) nor that harvested prior to immunization (prebleed). To evaluate the effectiveness of the anti-CT antibody response in the dual immunized mice, animals from the CT (100 µg) plus MSP (100 µg) group that developed high levels of anti-CT antibodies were orally challenged with CT and the degree of intestinal swelling (fluid accumulation) was compared with that induced in mice vaccinated with MSP alone. All of the animals immunized on the skin with CT and MSP together exhibited lower fluid accumulation levels ($p<0.01$) than comparably challenged mice in the MSP alone exposure group. Moreover, spleen and draining lymph node cells from the immunized mice exhibited a strong antigen-specific proliferative response in vitro in the draining lymph node and spleen, to which $CD4^+$T cells contributed. These results suggest that the antibodies to the adjuvant may confer protection against LT-mediated disease while functioning as an adjuvant for other antigens, such as candidate malaria vaccine antigens.

Immune responses to ETEC antigens in guinea pigs. To assess the capability for induction of antibody secreting cells (ASC) by TCI, an established guinea pig ASC animal model was selected. The guinea pig is a conventional model for assessment of toxic reactions in response to epicutaneous administration of adjuvant and antigen. Guinea pigs were exposed to increasing doses of LT (12 to 100 µg) and rCS6 (25 to 200 µg) on the skin on days 0, 21 and 42. Serum was collected for serology on days 1, 20, 41 and 56, and antibody titers to the antigen and adjuvant determined by ELISA. Similar to the results of the mouse studies, TCI administration of the rCS6 and LT vaccine resulted in induction of CS6 and LT antibody responses that appeared to be dose related with respect to CS6 and LT concentration (Table 2). The finding of serum antibody to CS6 was confirmed by the observation of ASC specific for CS6 in spleen and draining lymph node tissues. ELISPOT assay conducted on freshly isolated cells from sham PBS and CS6/LT immunized animals revealed a significant elevation ($p<0.05$) in the number of rCS6-specific IgG producing cells in 4 of 4 of the antigen exposed animals. Antigen-specific IgA and IgM producing cells also seemed enhanced although the actual number of cells detected was smaller and less consistent (Table 3).

TABLE 2

Serum anti-CS6 and anti-LT IgG in guinea pigs after TCI with CS6 and LT

| Adjuvant/Antigen per mouse (µg) | Mean serum IgG (ELISA Units) | | | |
|---|---|---|---|---|
| | Pre-bleed | 3 wk | 6 wk | 8 wk |
| LT(100)/CS6 (200) | n = 7 | n = 7 | n = 5 | n = 3 |
| Anti-CS6 IgG | 30 | 55 | 1588 | 4383 |
| Anti-LT IgG | 57 | 104 | 1258 | 3764 |
| LT(50)/CS6 (100) | n = 10 | n = 10 | n = 8 | n = 1 |

TABLE 2-continued

Serum anti-CS6 and anti-LT IgG in guinea pigs after TCI with CS6 and LT

| Adjuvant/Antigen per mouse (µg) | Mean serum IgG (ELISA Units) | | | |
|---|---|---|---|---|
| | Pre-bleed | 3 wk | 6 wk | 8 wk |
| Anti-CS6 IgG | 23 | 55 | 1155 | 12471 |
| Anti-LT IgG | 52 | 87 | 297 | 4933 |
| LT(25)/CS6 (50) | n = 6 | n = 6 | n = 4 | n = 2 |
| Anti-CS6 IgG | 24 | 26 | 103 | 1084 |
| Anti-LT IgG | 43 | 77 | 106 | 381 |
| LT(12)/CS6 (25) | n = 6 | n = 6 | n = 4 | n = 2 |
| Anti-CS6 IgG | 13 | 26 | 68 | 243 |
| Anti-LT IgG | 35 | 65 | 112 | 153 |
| PBS | n = 6 | n = 6 | n = 5 | n = 2 |
| Anti-CS6 IgG | 18 | 27 | 54 | 36 |
| Anti-LT IgG | 42 | 73 | 113 | 95 |

Two guinea pigs were designated for pathology per treatment group and one from the control group at each of the three exposures (Table 2). A full complement of tissues was subject to histopathologic evaluation in the high dose group. Tissues collected from the remaining groups (control, low, and mid range) were limited to the skin and liver. Gross necropsy and histopathology of the high dose group failed to demonstrate systemic lesions that could be attributed to the administration of the test article at any of the exposures. Hepatic necrosis was observed grossly in all animals including the PBS controls, but there was no correlation of the finding with the treatment groups. Serum alanine aminotransferase, aspartate aminotransferase, alkaline phosphatase, sodium, potassium, and blood urea nitrogen were evaluated and determined to be normal in all treatment groups.

TCI with LT/CS6 resulted in minimal to mild inflammatory changes limited to the local site of exposure and increases in the dose above 25 µg LT/50 µg CS6 had no appreciable effect on the severity of the local response. Typical findings were infiltration of the superficial dermis by low numbers of granulocytes and lymphocytes (inflammation), mild thickening of the epidermis by hyperplasia of keratinocytes (acanthosis), and occasional small foci where epidermal cells had lost cohesion, resulting in the formation of intraepidermal vesicles containing free keratinocytes (acantholysis). Minimal changes were seen in the lowest dose group (LT 12 µg/CS6 125 µg) at the three time points, and no skin changes were observed in the PBS exposed controls. In both mice and guinea pigs, there was no clinical progression in the severity of the skin findings with repeated immunization, and where seen, the vesicles either resolved or crusted and resolved spontaneously over several days.

TABLE 3

Individual guinea pig anti-CS6 ASC and IgG antibodies induced by TCI

| Immunization Group | Animal | ASC per Million Cells | | |
|---|---|---|---|---|
| | | IgG | IgA | IgM |
| PBS | 1 | 1 | 1 | 2 |
| | 2 | 2 | 0 | 4 |
| CS6/LT | 1 | 8 | 1 | 12 |
| | 2 | 42 | 3 | 1 |
| | 3 | 31 | 1 | 4 |
| | 4 | 63 | 5 | 7 |

HUMAN EXAMPLES

Healthy male and female volunteers, aged 18 to 45 years were recruited from the Washington, D.C. metropolitan area. Exclusion criteria included travel to an ETEC-endemic area in the previous year, recent history of traveler's diarrhea, pregnancy, infection with HIV, hepatitis B virus, hepatitis C virus, and allergy to antibiotics.

The vaccine components consisted of CS6 antigen mixed with LT. CS6 was produced under current good manufacturing practices (GMP) at the Forest Glen Pilot BioProduction Facility of the Walter Reed Army Institute of Research. The bacterial strain used for the production of CS6 was constructed from E. coli strain HB101 and a plasmid containing the four-gene operon necessary for CS6 expression inserted by recombinant techniques. The CS6 genes were cloned from ETEC strain E8875 (Wolf et al., 1997). The major steps in the production of CS6 included: bacterial fermentation; purification of the CS6 from the fermentation broth by tangential flow filtration followed by ammonium sulfate precipitation; intermediate storage of the bulk CS6 protein in phosphate buffered saline (PBS) solution at $-80°$ C.; thawing, stirring, and distribution into vials; and storage at $-80°$ C. CS6 was formulated as purified protein in 2 ml serum vials with gray split rubber stoppers sealed with aluminum crimps. Each vial contained 0.9 ml of (1.3 mg/ml) CS6 protein in PBS. Native LT of E. coli was produced under current GMP at the Swiss Serum and Vaccine Institute (SSVI). The LT was produced from E. coli strain HE22 TP 235 Km. The LT was supplied as lyophilized powder. Each vial contained 500 µg of lyophilized LT, and was reconstituted with 1 ml sterile water. The doses of adjuvant (LT) and antigen (CS6) by vaccination group are shown in Table 4.

The vaccine was administered in three doses. The first dose was administered on day 0, and the second and third immunizations on days 28 and 84 respectively after the first immunization. The vaccine was administered transcutaneously using a semi-occlusive patch consisting of a 2×2 inch cotton gauze matrix (two-ply Kendall #2556) with a 2×2 inch polyethylene (SARAN WRAP) backing covered by a 4×4 inch TEGARDERM dressing (semi-occlusive, 3M cat # 1616).

At the time of vaccination the vaccine was applied in 500 µl of sterile saline and administered as a split dose on each upper arm. Each split dose contained the corresponding dose of CS6 (antigen) alone or in combination with 250 µg of LT (adjuvant). The upper arm was positioned in a half-extended manner on an examination table and prepared by gently rubbing five times with an isopropyl alcohol (70%) swab. The cotton gauze was placed on each upper arm and the immunization solution was applied to the gauze with a syringe. The polyethylene backing was then placed over the impregnated cotton gauze and covered with the Tegaderm dressing. Volunteers remained in the research clinic for 20 min following patch application for observation. Volunteers were instructed not to touch the patches or engage in strenuous physical activity during the time the patches were worn. The patches were removed 6 hr after application (range: 4-8 hr). The immunization sites were then rinsed with 500 ml of water and patted dry. The volunteers were instructed to bathe or shower in the evening but to refrain from heavy scrubbing of the immunization site with soap to avoid unusual irritation of the skin. Volunteers were re-immunized at 28 and 84 days after the first immunization. Each volunteer received the same dose of vaccine on each immunization.

Volunteers were observed for 20 min after each dose for occurrence of immediate adverse effects. The volunteers were given a diary to record signs and symptoms observed after vaccination. Reported symptoms were graded as mild (noticeable), moderate (affecting normal daily activities), or severe (suspending normal daily activities). The volunteers were evaluated at 24 hr and 48 hr for clinical assessment and evaluation of possible side effects. Volunteers who showed signs of vaccine skin reactions were instructed to return to the clinic at 72 hr for additional clinical assessment. Volunteers were then followed as needed until side effects had completely resolved. One of the volunteers who developed a skin rash in the site of immunization was asked to undergo a skin biopsy. This biopsy was performed by a dermatologist, following standard procedure, and under a separate written informed consent.

Antibody-secreting cells (ASC) immune responses to the vaccine antigens were chosen as an immunological endpoint for this study, since previous studies have shown that ASC responses correlate with mucosal intestinal immune responses (Wenneras et al, 1992). Venous blood samples were obtained from the volunteers on day 0 before immunization, and on days 7, 28, 35, 56, 84, 91, 98, and 112 after the first immunization. Blood specimens were collected using the VACUTAINER system of EDTA-treated tubes (Becton Dickinson). Peripheral blood mononuclear cells (PBMC) were isolated from the blood sample by gradient centrifugation on Ficoll-Hypaque (Sigma) and were assayed for total and vaccine-specific numbers of IgA and IgG ASC by the ELISpot technique (Czerkinsky et al., 1988; Wenneras et al, 1992). Individual wells of nitrocellulose-bottomed 96-well plates (Millititer HA; Millopore, Bedford, Mass.) were coated with 0.1 ml of purified CS6 (20 µg/ml) or $GM_1$ ganglioside (0.5 µg/ml) and incubated overnight at 4° C. After a PBS wash, GM1-coated wells were exposed to LT (0.5 µg/ml) for 2 hr at 37° C. After being washed with PBS, the plates were blocked with complete RPMI medium (Gibco) supplemented with 5% fetal calf serum (Gibco) and 50 µg/ml gentamicin (Gibco). The PBMC were adjusted to $2\times10^7$ viable cells/ml in complete RPMI medium. A final 0.1 ml suspension of PBMC was added to each well ($1\times10^6$ PBMC added per well), and plates were incubated for 4 hr at 37° C. in 5.0% $CO_2$. Plates were washed, incubated overnight at 4° C. with a mixture of two affinity-purified goat anti-human immunoglobulin antibodies with distinct isotype specificities, one conjugated to alkaline phosphatase (IgG) and the other conjugated to horseradish peroxidase (IgA) (Southern Biotech Associates) and exposed to the appropriate chromogen-enzyme substrate (Sigma). Spots, corresponding to a zone of antibodies secreted by individual cells, were enumerated in triplicate wells under 40× magnification, with data expressed as the number of spot-forming cells per $10^6$ PBMC.

As previously described (Ahren et al., 1998; Jertborn et al., 1998; Jertborn et al., 2001), we defined a positive ASC response as a ≧2-fold increase over baseline value of the ASCs per $10^6$ PBMC, when the number of ASCs was ≧0.5 per $10^6$ PBMC in the baseline sample. If the number of pre-immune ASCs was less than 0.5 per $10^6$ PBMC, a value of >1.0 per $10^6$ PBMC after dosing was considered a positive response.

Venous blood samples were obtained from the volunteers before immunization and on days 14 and 28 after each immunization for measurements of serum antibody titers. IgA and IgG antibody titers against LT were measured by the GM1-ELISA method (Jertborn et al., 1998; Svennerholm et al., 1983), and those against the CS6 were determined by ELISA methods as previously described (Hall et al., 2001; Stoll et al., 1986). LT (provided by SSVI) and CS6 (GMP Lot 0695, WRAIR) were used as solid-phase antigens. The LT and CS6 used for the ELISA essays were from the same lots used for the vaccine preparation. Individual microtiter wells (Nunc-Immunoplates) were coated with GM1 ganglioside (0.5 µg/ml) (Sigma) at room temperature overnight, or with 0.1 ml of a 1.0 µg/ml preparation of CS6 at 37° C. overnight. GM1-coated wells were then washed with PBS and incubated with 0.1 ml of LT (0.5 µg/ml) for 2 hr at 37° C. After blocking with 0.1% bovine serum albumin (Sigma), the serum samples were threefold serially diluted (initial dilution 1:5) and then incubated at room temperature for 90 min. Bound antibodies were demonstrated by addition of rabbit anti-human IgA or IgG conjugated with horseradish peroxidase (Jackson ImmunoResearch Laboratories, PA) and incubated at room temperature for 90 min, followed by addition of O-phenylenediamine (OPD)-$H_2O_2$ (Sigma). The endpoint titers were assigned as the interpolated dilutions of the samples giving an OD of 450 nm of 0.4 above background (absorbance at 450 nm). Titers were adjusted in relation to a reference specimen included in each test to compensate for day-to-day variation. For both antigens, pre- and post-dosing serum samples from the same volunteer were always tested side by side. The antibody titer ascribed to each sample represented the geometric mean of duplicate determinations performed on different days. Reciprocal endpoint titers <5 were assigned a value of 2.5 for computational purposes. Based on our calculations of the methodological error of each ELISA, previous to the study, we defined a significant response (seroconversion) as ≧two-fold increase in endpoint titer between pre- and post-immunization specimens (Jertborn et al., 1986), with the added criterion that the post-immunization reciprocal titer be ≧10.

All volunteers receiving the three scheduled doses of vaccine were included in the post-dosing safety and immunogenicity analyses. Proportions were compared using the $2 \times n\chi^2$ test at $\alpha=0.05$, power=0.80. The Fisher's exact test was used in 2×2 tables when the number contained in one of the cells was less than 5 (Sahai & Khurshid, 1995). The median number of ASC and median plasma antibody titer fold increases were compared separately using the Wilcoxon rank test to assess the boosting effect of each consecutive dose of vaccination (Forrester & Ury, 1969). All statistical tests were two-tailed.

Informed consent was obtained from all volunteers, and the human use guidelines of the U.S. Department of Defense were followed in the conduct of this trial. Thirty-three volunteers were enrolled and received at least one dose of the study vaccine. The protocol was approved by the Institutional Review Board of the Office of The Surgeon General, U.S. Army. The volunteers were 21 to 44 years of age; 17 females and 16 males; 15 black, 16 white, and two Asian. Of the 33 volunteers, seven did not complete the study for reasons unrelated to the study: conflict with their work schedule (4), moving from the D.C. metropolitan area (2), and admission to a local clinic for illegal drug use (1). Twenty-six volunteers received the three scheduled doses of the vaccine and completed all the post-vaccination follow-up visits, and the data on these volunteers is shown. These volunteers were 21 to 44 years of age; 13 females and 13 males; 12 black, 12 white, and two Asian. The number of volunteers by vaccine dose is shown in Table 4.

TABLE 4

Number of volunteers by vaccine group (n = 26)

| Dose of antigen (CS6)* | Dose of Adjuvant (LT)* | |
|---|---|---|
| | 500 µg | 0 µg |
| 250 µg | 5 | 2 |
| 500 µg | 5 | 1 |
| 1000 µg | 5 | 1 |
| 2000 µg | 4 | 3 |
| Total | 19 | 7 |

*Dose was split between two patches

Of the volunteers receiving a combination of LT/CS6, 74% (14/19) developed a maculo-papular rash at the site of vaccination. No volunteers receiving CS6 alone developed a rash. The reaction was mild in 13 volunteers and moderate in one volunteer. White volunteers developed the rash significantly more frequently than black volunteers (11/11 vs. 3/8, p<0.005). Seven reactions occurred after the administration of the 2nd dose and 14 occurred after the third dose; all 7 volunteers with a 2nd dose-related rash also developed the rash after the application of the 3rd dose. The clinical diagnosis was contact dermatitis (delayed type hypersensitivity-DTH). One volunteer with the characteristic rash underwent a biopsy of the affected skin after receiving the third dose of LT/CS6. The biopsy showed mild dermal chronic inflammation (lymphocytic) with focal spongiosis. The pathological diagnosis was sub acute spongiotic dermatitis, characteristic of DTH. The rash usually began within 24 hrs after patch application. Rash developing after the second dose lasted a median of 9 days, (range 1-14); the third dose rash lasted a median of 6 days, (range 1-11). Volunteers were offered 0.1% triamcinolone cream for relief of potential vaccine related symptoms. None of the subjects used the cream after the first or second immunizations. Eight patients with rashes that occurred after the third dose were treated with the triamcinolone cream. There were no apparent clinical differences regarding the appearance and severity of local symptoms (pruritus) or signs (erythema, papules) when compared by vaccination dose. There were no statistically significant differences in the magnitude of the serological immune responses between the users of triamcinolone cream as compared to non-users.

Immune responses were detected only in volunteers receiving both adjuvant and antigen, although one volunteer who received only two doses of CS6 alone had a positive anti-CS6 IgA response (but no CS6 IgG) at a single time point. There were no significant differences in the frequency or the magnitude of the serum antibody or ASC responses to LT and CS6 between the four groups that received the adjuvant and antigen combination; therefore, data were pooled for further statistical analysis and presentation. All volunteers (100%) receiving LT demonstrated a serum anti-LT IgG response, and 90% produced anti-LT IgA. Anti-CS6 serum antibody responses rates were lower than the anti-LT response rate with 68% and 53% of volunteers showing greater than two-fold rise in anti-CS6 IgG and IgA titers, respectively. The individual peak fold rises in serum antibodies to LT and CS6 are depicted in FIG. 1. Robust responses to both LT and CS6 were observed with serum antibodies, although there was a great deal of variability in the magnitude of the response. The mean anti-LT IgG response to LT exceeded the mean fold response previously described by nearly a log (Glenn et al., 2000), and was greater than the response to CS6.

The kinetics of the serum antibody responses are depicted in FIG. 2. The post-dose serum antibody titers for each group were combined and are presented as geometric mean titers with 95% confidence intervals. The kinetics of the immune responses to LT differ markedly from the kinetics of the response to CS6 in that strong priming and boosting responses to LT were seen whereas the CS6 responses were primarily seen with boosting. Memory responses to CS6 appear to occur, as suggested by the significant difference in the pooled anti-CS6 IgG and IgA responses after both the second and third immunization.

The percent of ASC response rate and median number of antigen-specific ASC×$10^6$ PBMC are shown in Table 5. Both CS6 and LT-specific ASC were detected. The time and magnitude of peak number ASC for each individual responder by specific ASC type are depicted in FIG. 3. In the majority of responders, peak ASC were detected after the second or third immunization. All seven volunteers that demonstrated anti-CS6 IgG ASC had their peak number of ASC after the third immunization.

TABLE 5

Antigen-specific ASC responses (n = 19)

| ASC type | Number of responders (%)* | Median Number ASC per $10^6$ PBMC (range)** |
|---|---|---|
| Anti-LT IgG | 15 (79) | 9 (1.3-49) |
| Anti-LT IgA | 7 (37) | 2.4 (1.3-46) |
| Anti-CS6 IgG | 7 (37) | 6 (1.7-77) |
| Anti-CS6 IgA | 8 (42) | 2.4 (1.7-12) |

*A positive ASC response was defined as a ≧2-fold increase over baseline value of the ASCs per $10^6$ PBMC, when the number of ASCs was ≧0.5 per $10^6$ PBMC in the baseline sample. If the number of preimmune ASCs was less than 0.5 per $10^6$ PBMC, a value of >1.0 per $10^6$ PBMC after dosing was considered a positive response.
**Only positive responses were included when calculating the median number of ASC (range).

Enterotoxigenic *Escherichia coli* (ETEC) is one of the most common causes of childhood diarrhea in developing countries. It is also the principal cause of traveler's diarrhea. Clinical manifestations of disease are caused by the bacteria secreting one or two enterotoxins, heat-labile enterotoxin (LT) and the poorly immunogenic heat-stable enterotoxin (ST), both interact with the intestine to cause watery diarrhea characteristic of the disease. A requirement for infection is the ability of ETEC organism to adhere to the intestinal epithelium. This occurs through structures on the outer membrane called fimbrie. As a class, these structures are antigenically distinct and named colonization factor antigens (CFA). To date, 20 different colonization factors (CF) have been identified. The most prevalent, and relevant to human disease, include CFA/I, CFA/II and CFA/IV. CFA/II is composed of three separate antigens named as coli surface antigen 1 (CS1), CS2 and CS3. CFA/IV is composed of three antigens, CS4, CS5 and CS6.

The age-associated decline in the incidence of ETEC infections in the developing world has been attributed to the development of protective immunity. Epidemiology studies demonstrate that infants infected become resistant (protected) from reinfection with the same strain. It was shown that volunteers experimentally infected are protected from rechallenge with a homologous strain. Human volunteers challenged with a heterologous ETEC strain are not protected against clinical disease.

The CFA's have been identified as likely candidates for evaluation of ETEC vaccines. However, for broad range coverage against natural infection, an ETEC vaccine must consist of multiple colonization factor antigens. The broadest range of coverage (80% -95%) requires the development of a multivalent vaccine consisting of several CFA (CS3, CS6 and CFA/I) and enterotoxin (LT and ST). Although oral administration is possible, these protein antigens are sensitive to hydrolysis at low pH and enzymatic degradation in the stomach. In addition, large doses of the vaccine are required for oral vaccination are not practical as a product. ETEC vaccine is not amenable to other routes of administration since the enterotoxins (LT and ST) are reactogenic (diarrhea) and inflammatory when administered by other routes, including oral, nasal, pulmonary, rectal and parenteral.

The efficiency and safety of TCI has been applied to this vaccination problem. In the following examples, it is demonstrated that multivalent combinations of CS3, CS6, CFA/I, LT and ST can be effectively delivered through the stratum corneum with or without penetration enhancement and they induce an immune response against each component of the multivalent vaccine. Vaccination by TCI requires a low dose of the antigens (CS3, CS6 and CFA/I) and the immune response is significantly augmented by simultaneous co-administration of an adjuvant. TCI can be preformed safely and without eliciting serious, adverse side effects. We describe antigen and adjuvant doses that are effective, dosing regimens, methods for optimizing delivery of the vaccine into the skin to antigen presenting cells, and formulations which are stabilizing and pharmaceutically acceptable for transcutaneous immunization.

Materials and Methods

Preclinical studies were conducted to establish the optimal method for TCI with a complex mixture of CFA and LT. The objective of the following study was to demonstrate the feasibility of transcutaneous vaccination with mixtures of CS3, CS6, CFA/I, LT and STa. In these studies, adult C57BL/6 mice (7-8 weeks old) were used.

Mice were shaved on the dorsal, ventral surface at the base of the tail (24-48 hrours) prior to vaccination. All mice were anesthetized by intraperitoneal injection of 25 µl of a mixture of ketamine (100 mg/ml) and xylazine (100 mg/ml). The shaved site was pretreated by hydration with saline or a mixture of 10% glycerol and 70% isopropyl alcohol. While still fully hydrated, the skin was gently treated by one of two methods to disrupt the outermost layer of skin, the stratum corneum (SC). Tape stripping was preformed by applying 3 M or D-squame® adhesive tape to the prepared surface followed by gentle removal of the tape 10 times. Alternatively, the hydrated skin was pretreated by mild abrasion with emery paper (GE Medical Systems) or a swab containing pumice (PDI/NicePak). The skin surface was gently buffed 10 times using an up-and-down motion. Immediately prior to application, a Nu-gauze pad (~1 cm²), affixed on an adhesive backing, was loaded with 25 µl volume containing different combinations of CS3 (25 µg), CS6 (25 µg), CFA/I (25 µg), STa (8 µg) and LTR192G (25 µg). The vaccine-loaded patches were applied overnight (~18 hr), removed, and the skin rinsed with water. All mice received two or three doses two weeks apart on day 0, 14 and 28.

Peripheral blood was obtained by lacerating the tail vein. The blood was collected in a tube, allowed to clot, centrifuged, and the serum collected. Serum samples were collected on day 0 (pre-immune), day 14, day 28 and day 42 (two weeks after the third dose). The serum was frozen at −20° C. until evaluated for antibodies to the vaccinating antigens (CS3, CS6, CFA/I and STa) and adjuvant (LTR192G). The latter was provided by the U.S. Navy Medical Research Center.

Fecal samples were collected on day 35 (7 days after the third immunization). Fresh samples were collected from each mouse and extracted with PMSF (3 µg/ml in saline). The samples were agitated (VORTEX mixer) to form a suspension and clarified by centrifugation (3,000 rpm, MICROFUGE). The clarified supernatants were recovered and stored at −20° C. until evaluated with an ELISA method for mucosal IgG and IgA.

An enzyme linked immunosorbent assay (ELISA) method was used to assess the serum IgG. Ninety-six well plates were coated with 1 µg antigen/100 µl per well overnight at 4° C. After washing with phosphate buffered saline and Tween 20 (PBS-T), the plates were blocked with 100 µl of blocking buffer (0.5% casein and 0.5% bovine serum albumin) for 1 hr at room temperature. After washing the plates with PBS-T, the samples were serially diluted (serum samples 3-fold serial dilution and fecal samples 2-fold serial dilution). The plates were incubated overnight at 4° C. The plates were washed with PT buffer and 100 µl of optimally diluted (1:2,000) goat anti-mouse IgG conjugated with HRP (Bio Rad) or HRP conjugated goat anti-mouse IgA (Zymed) was added to each well. The plates were incubated for 2 hr at room temperature, washed with PT buffer and 100 µl of substrate ABTS (KPL) was added to the wells and the reaction allowed to develop for 30 min. The reaction was stopped by adding 100 µl of 1% SDS solution (Gibco). The optical density was read at 405 nm with an ELISA plate reader and the data analyzed using Softmax Pro 2.4 software (Molecular Devices).

Serum antibodies to formalin inactivated ETEC whole cells were determined by the ELISA method. Enterotoxigenic E. coli strain E243778 were cultured in on agar plates, the cells harvested and inactivated in 2.5% formalin overnight at room temperature. The wells were coated with $5 \times 10^5$ killed whole cells (EWC). The plates were prepared as described for other antigens. Serum antibodies to EWC was determined by the method described above.

Mice were sacrificed by asphyxiating with carbon dioxide and the spleen and inguinal lymph nodes removed. The tissues were maintained on ice in tubes containing RPMI 1640 medium (Gibco). Single cell suspensions were prepared by grinding the tissue with the barrel of a 5 cc syringe. Tissue debris was allowed to settle to the bottom of the tube and the cell suspension was transferred to another tube. The cells were washed twice with RPMI 1640 medium and suspended in culture medium (RPMI 1640, 10% FBS, 2 mmol of L-glutamine and 2 mmol pen-strep).

Ninety-six well filtration plates (Millipore Bedford, Mass.) were coated with 100 µl of 3 µg/ml antigens in PBS and incubated overnight at 4° C. The plates were rinsed three times with PBS, blocked with 2% BSA (Sigma) for 1 hr and rinsed with PBS. Cells were dispensed at 100 µl per well in culture medium (RPMI 1640, 10% FBS, 2 mmol of L-glutamine and 2 mmol pen-strep) and plates were incubated overnight at 37° C. in a humidified 5% $CO_2$ incubator. The plates were washed four times with PBS-0.05% Tween 20 (PBS-T). The cells were lysed by hypotonic shock with water. One hundred µl of biotin conjugated goat anti-mouse IgA (Southern Biotechnology) or biotin conjugated goat anti-mouse IgG (Amershan) 1:2000 dilution in 2% BSA in PBS. The plates were incubated at room temperature for 2 hr. After the plates were washed with PBS-T, 100 µl of alkaline phosphatase-labeled avid in D antibody (Vector) 1:2000 were added to each well and incubated for an additional 2 hr at room temperature. The plates were washed with PBS-T and 100 µl of BCIP/NBT solution (Kirkegaard & Perry) was added to the wells and the plates incubated 5 to 30 min at room temperature until blue spots develop. The plates were washed with distilled water to stop the reaction. Antigen specific ASC were visualized as blue spots, which were counted with a dissecting microscope and recorded as IgG-ASC or IGA-ASC per $10^6$ cells.

In Vitro Assay for Characterizing Neutralizing Antibodies to the ETEC Enterotoxin LT Heat-labile enterotoxins from E. coli (LT) is produced as a multisubunit toxins with A and B subunits. After the initial interaction of the enterotoxin with the host cell membrane receptor (GM1 ganglioside), the B subunit facilitates the penetration of the A subunit through the cell membrane and into the eukaryotic cell. With chemical reduction, this A subunit dissociates into two smaller peptides: $A_1$ catalyzes the ADP-ribosylation of the stimulatory GTP-binding protein in the adenylate cyclase enzyme complex on the basolateral surface of the epithelial cells. This results in increasing the intracellular level of cyclic AMP (cAMP). The increase in cAMP causes secretion of water and electrolytes into the small intestine resulting in clinical disease.

In cell culture, LT binds with high affinity ($K_D = 7.3 \times 10^{-10}$) to the GM1 gangiloside receptor, which is expressed by many eukaryotic tissues and cells. LT causes striking morphologic changes to many eukaryotic cells (for example, CHO and Y1) in cell culture. Using this property, an in vitro assay method was developed to determine if antibodies elicited through TCl inhibit LT (neutralize) binding to the GM1 ganglioside receptor. In these studies, CHO cell were cultured in F12 medium supplemented with 10% fetal calf serum (FCS). The cells were maintained in log phase growth at 37° C. in 5% $CO_2$. The cells were trypsinized from T flasks and plated into 96 well plates at $5 \times 10^3$ in 0.2 ml of F12 supplemented with 1% FCS. Pre-immune (day 0) and post-immune (day 321) sera were collected from volunteers that had been transcutaneously vaccinated with LT and determined by the ELISA method to have antibodies to LT. These sera were diluted 1:4 with culture media and 2-fold serially diluted up to 1:8192. An equal volume of diluted serum was mixed with LT for 1 hr at 37° C. Fifty µl of serum/LT (containing 6.5 ng LT) was transferred to duplicate freshly plated CHO cells cultures ($5 \times 10^3$ cells in 150 µl medium). The cells were cultured at 37° C. for 24 hr. At the end of the culture period, the media was removed, the cells washed with F12, fixed with methanol and stained with Giemsa stain. The cultures were examined with a inverted light microscope and cultures graded for normal appearance or elongated morphology. The results were expressed as the lowest dilution of serum that blocked (neutralized) cell elongation by greater than 90% within the culture.

Methods for Conjugating Heat Stable Toxin (STa) to LT or Other Carrier Protein to Improve Immunogenicity and Transcutaneous Delivery STa (lot 1184A, List Biological) conjugation to LT involves two steps. The first step was to maleimide activate LT, 400 µg of LT (lot 200100, Berna Biotech) was dissolved in 400 µl of 0.1 M phosphate buffer 0.15 M NaCl buffer (pH 7.2). 160 µl of succinmidyl-6[((β-maleimidopropipropionamido0 hexanoate] (SMPH, Pierce) about 8 µl to LT solution and incubated for 90 min at room temperature. The reaction was desalted on a desalting column (Pierce) by using PBS and fractions were collected. The activated LT peak was pooled and protein determined by a BCA assay (Pierce). The second step is conjugation; 80 µg of STa was mixed with the maleimide activated LT and incubated overnight at 4° C. The ST-LT conjugate was dialyzed against 500 ml PBS buffer.

Purified STa (100 μg) was coupled to 800 μg of chicken egg ovalbumin (OVA, Sigma) in 1 ml of reaction mixture containing 10 mg of 1-ethyl-3-(3-dimethyl-aminopropyl)-carbodiimide (Pierce) and 0.1 M sodium phosphate buffer (pH 5.5). The reaction mixture was dialyzed against phosphate buffer saline (20 nm, pH 7.2, PBS) for 4 hr.

Conjugation was confirmed by shift in the molecular weight of ovalbumin and LT-B using SDS-PAGE method. Each sample was dissolved in 4× sample buffer (Invitrogen) and heated 100° C. for 5 min and analyzed the NuPAGE 4-12% Bis-Tris gel (Invitrogen). After electrophoresis, protein bands were visualized using a silver staining kit (Invitrogen) and molecular weights of the conjugates were determined relative to internal reference standards run on the gels.

Example 1

Comparison of the Serum IgG Response to Transcutaneous and Intradermal Vaccination with ETEC Colonization Factors The purpose of this study was to compare the immune response elicited by transcutaneous vaccination, to that of intradermal, vaccination with CS3 and CS6. Groups of mice were pretreated by tape stripping 10 times to remove the stratum corneum. Groups of 5 mice then transcutaneously vaccinated with CS3 (25 μg), CS6 (25 μg) with and without 10 μg of LTR192G adjuvant. Patches were loaded with a 25 μl volume containing CS3 or CS6 alone or CS3 plus LTR192G or CS6 plus LTR192G. The patches were applied overnight (~18 hr). Separate groups of mice were injected intradermal with 25 μg of CS3 or CS6. All mice received three vaccinations (day 0, 14 and 28). Sera were collected two weeks after the third immunization and evaluated for antibodies to CS3, CS6 and LTR192G.

The results shown in FIG. 4 demonstrate that CS3 and CS6 elicit serum antibodies when epicutaneously applied to the skin. The serum antibody response were further enhanced by co-administration of low doses of LTR192G (10 μg). As depicted in FIG. 4, serum titers to CS3 and CS6 were increased 2-fold and 12-fold, respectively, by addition of LTR192G adjuvant. Intradermal injection of CS3 elicited a high titer response (1:273,695) compared to epicutaneous application (1:30,581). Transcutaneous vaccination with CS6 elicited very high-titer antibodies (1:188,984), which were 10-fold greater compared to intradermal injection of CS6 (1:17,036). In addition, high antibody titers to LTR192G were also detected whether the LTR192G was epicutaneously applied alone or in combination with CS3 or CS6. These results demonstrate that high molecular weight ETEC antigens (CS3, ~3 megadaltons and CS6 ~1 megadalton) are immunogenic when administered in a patch on skin that has been pretreated to remove the stratum corneum. The magnitude of the immune response is greatly enhanced by co-administration of an adjuvant (LTR192). The mutant LTR192G also elicits production of high titer antibodies against itself when epicutaneously applied alone or in combination with CS3 or CS6.

Example 2

Transcutaneous Vaccination with Divalent and Trivalent Combinations of ETEC Subunit Vaccines Skin was pretreated as described in Example 1. Mice were transcutaneously vaccinated with patches containing 25 μg CS3/10 μg LTRL 192G; 25 μg CS6/10 μg LTR192G; or a cocktail of 25 μg CS3/25 μg CS6/10 μg LTR192G. The results are shown in FIG. 5. These results demonstrate that the trivalent vaccine combination (CS3/CS6/LTR192G) elicited serum IgG titers that were comparable to the divalent vaccines (CS3/LTR192G and CS6/LTR192G).

This clearly demonstrates the feasibility of combining multiple ETEC subunit vaccines into a single patch and that multiple subunits vaccines can be co-administered without negatively affecting the magnitude of the immune response to either subunit (i.e., CS3 or CS6)

Example 3

TCI with CS3/CS6 with and Without Co-Administered LTR192G Adjuvant

The next study was undertaken to determine if LTR192G would adjuvant the immune response to an epicutaneously administered combination of CS3 and CS6. The animals were pretreated as described in Example 1 and the vaccine loaded patches were applied (overnight) to the pretreated skin (base of tail). The results shown in FIG. 6 demonstrate that the immune responses to CS3 and CS6 were greatly enhanced 5-fold and 24-fold, respectively, be addition of 10 μg LT to the trivalent mixture. This establishes that it is feasible to transcutaneously vaccinate with three ETEC antigens. LTR192G is an important adjuvant and antigen, and it enhances the immune response to CS3 by 5-fold and CS6 by 24-fold.

Example 4

CS3 and CS6 Molecules are Antigenically Distinct

The specificity of the immune response to CS3 and CS6 was determined. Mice were pretreated with tape stripping and received two patches: one on day 0 and the other on day 14. Groups of animals were vaccinated with 25 μg CS3/10 μg LTR192G or with 25 μg CS6/10 μg LTR192G. Ten days after the second dose (day 24) serum was collected and evaluated for antibodies to CS3 and CS6. The results shown in FIG. 7 demonstrate that vaccination with CS3 elicits specific antibodies that did not exhibit cross-reactivity with CS6. Likewise, antibodies to CS6 did not recognize CS3. These results clearly show that immunity to CS3 and CS6 is highly specific and that ETEC vaccines intended for broad range protection against enterotoxigenic *E. coli* strains will need to be multivalent.

Example 5

TCI with CS3 and LTR192G Elicits IgG1 and IgG2a Subclass Antibodies

Mice were pre-shaved at the base of their tails and the skin was hydrated with 10% glycerol and 70% isopropyl alcohol. Their hydrated skin was pretreated with emery paper 10 times. Groups of mice were vaccinated with 25 μg CS3 alone or with a combination of 25 μg CS3/10 μg LTR192G. The mice were transcutaneously vaccinated on three times (day 0, 14 and 28) and serum collected 30 days after the third immunization (day 58). The results shown in FIG. 8 demonstrate that IgG1 is the major IgG subclass elicited here. IgG1 titers were greater when the LTR192G adjuvant was co-administered with CS3. In addition, measurable antigen specific IgG2a was also detected. IgG2a subclass, however, was only detected when the adjuvant was co-administered. These results confirm and extend the previous observation that the LTR192G adjuvant does augment the serum antibody response to CS3 and further demonstrates that the adjuvant may also direct Th2 and Th1 immune responses to antigens delivered by the epicutaneous route.

Example 6

TCI with CS6 and LTR192G Elicits IgG1 and IgG2a Subclass Antibodies

The mice were shaved and pretreated as described in Example 5. Groups of mice were transcutaneously vaccinated with 25 µg CS6 alone or with a combination of 25 µg CS6/10 µg LTR192G. The mice received three vaccinations (day 0, 14 and 28) and serum was collected 30 days after the third immunization. The results in FIG. 9 demonstrate that LTR192G did adjuvant (i.e., augment) the serum IgG response to CS6. As with CS3, antibodies to CS6 were both IgG1 and IgG2a subclasses. The generations CS6-specific IgG2a, however, was dependent upon use of the LTR192G adjuvant.

Example 7

Serum IgG Subclasses Elicited to LTR192G Following TCI

Mice were pretreated by the same procedure described in Examples 5 and 6. The mice received three transcutaneous-vaccinations (day 0, 14 and 28) and serum was collected 30 days after the third immunization (day 58). The results shown in FIG. 10 show that IgG1 was a major serum antibody subclass elicited by TCI. As with CS3, CS6, LTR192G-specific IgG2a subclass was also elicited by TCI.

Example 8

Serum IgG Subclasses Elicited to LTR192G when Co-Administered with CS3 or CS6 in TCI Mice were pretreated by the procedures described in Examples 5-7. In this study, 10 µg of LTR192G was admixed with 25 µg of CS3 or 25 µg CS6. Groups of mice received three transcutaneous vaccinations on day 0, 14 and 28 and serum was collected 30 days after the third immunization (day 58). As was observed in Example 7, serum IgG1 was the major subclass antibody elicited against LTR192G (FIG. 11). Measurable IgG2a was also produced. This study further demonstrates that vaccination with a combination of CS3/LTR192G or CS6/LTR192G did not negatively affect the production of antibodies to the adjuvant. These results indicates that as a component of the ETEC vaccine LTR192G serves a dual purpose, as an adjuvant and as an antigen in the vaccine.

The significance of IgG subclass characterization is related to the mechanism by which a transcutaneous ETEC vaccine might protect against natural infection. These results demonstrate that transcutaneous vaccination elicits two subclasses of IgG antibody that are expected to function differently in protecting the host against natural infection. These mechanisms are by "neutralization" and "complement mediated cytotoxicity." IgG1 antibodies to CS3 and CS6, for example, are expected to function by blocking (neutralizing) the ability of $CS3^+$ and $CS6^+$ ETEC strains from colonizing the small intesting, a step that is essential to pathogenesis. IgG2a class antibodies are expected to protect the host from infection by a different mechanism. This class of antibody, when in complex with CS3 or CS6 antigens on the surface of enterotoxigenic *E. coli*, will mediate the activation of complement, which through a series of enzymatic steps, will result in the lysis (killing) of the bacterial cells. Both mechanism are effective in protecting the subject against infection.

Example 9

Mucosal Immune Response to CS3 Antigen After TCI

Figure 12A:
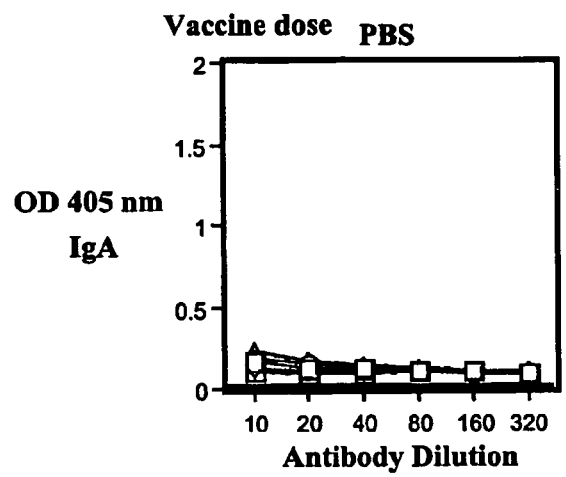
Figure 12B:
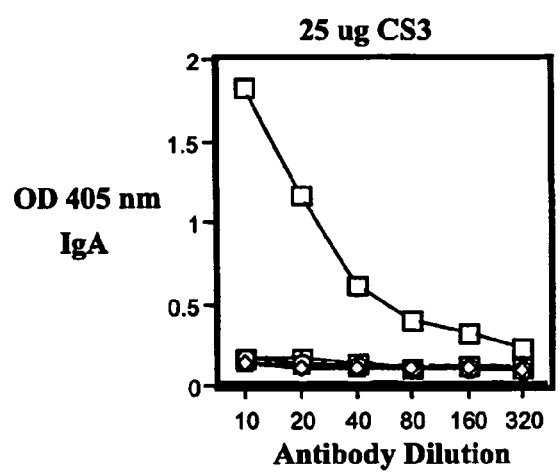
Figure 12C:
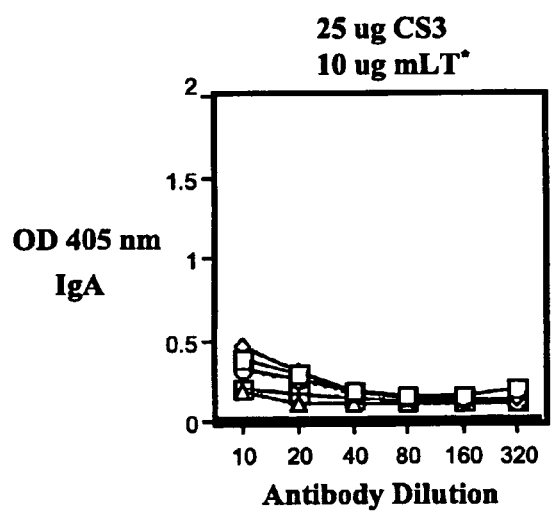
Figure 12D:
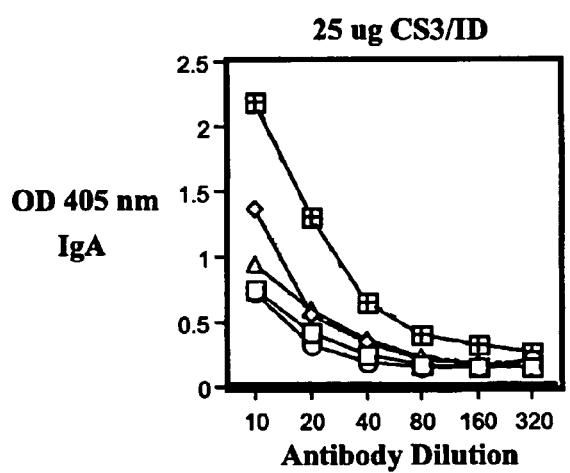
Figure 12E:
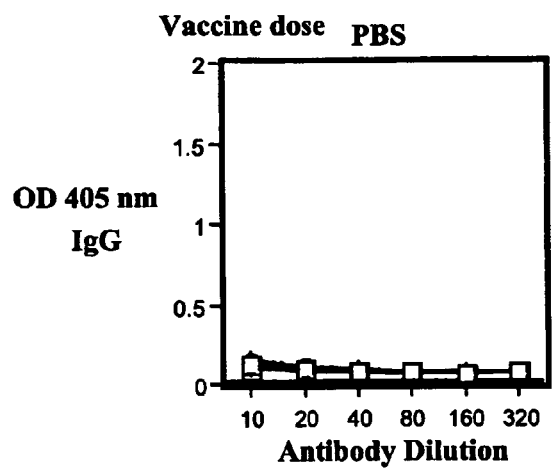
Figure 12F:
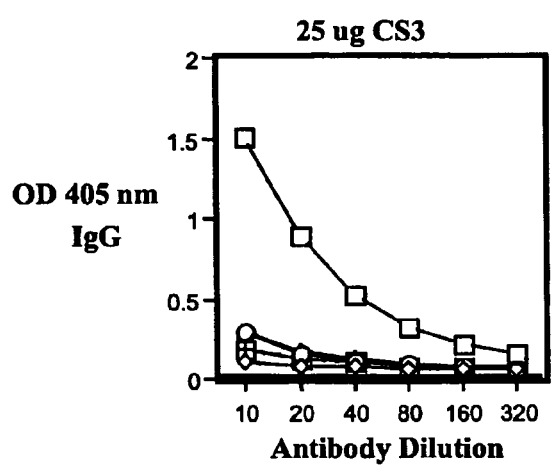
Figure 12G:
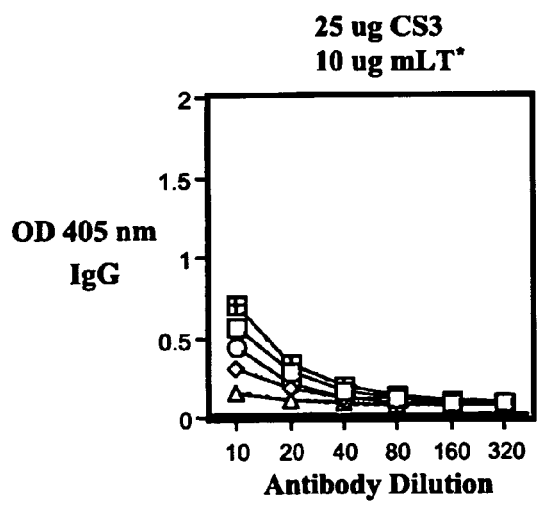
Figure 12H:
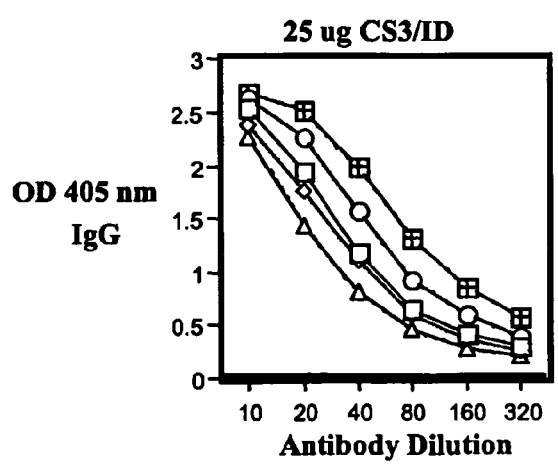
Figure 13A:
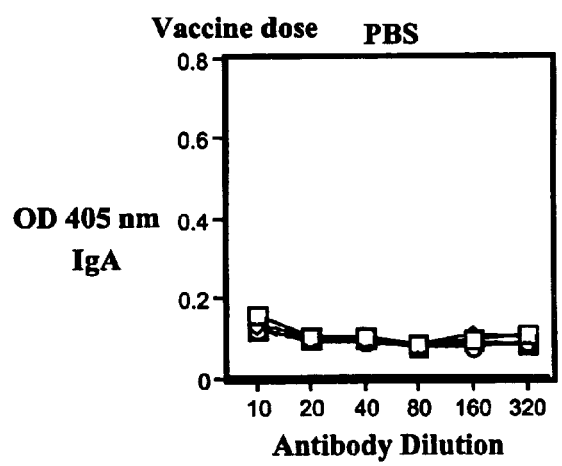
Figure 13B:
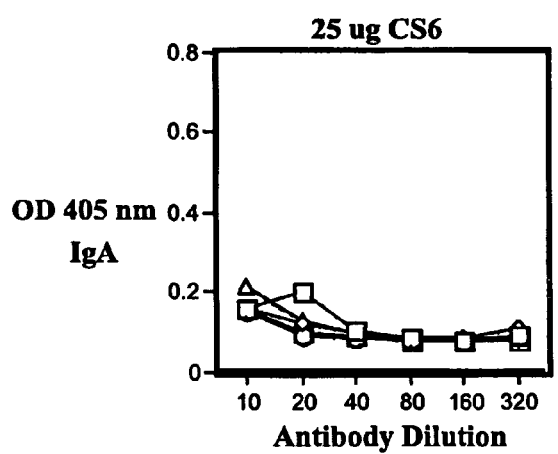
Figure 13C:
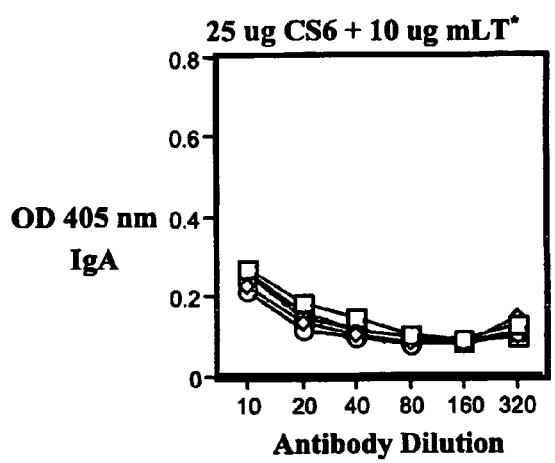
Figure 13D:
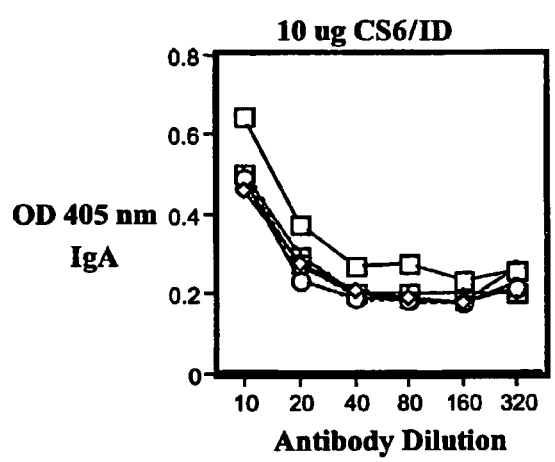
Figure 13E:
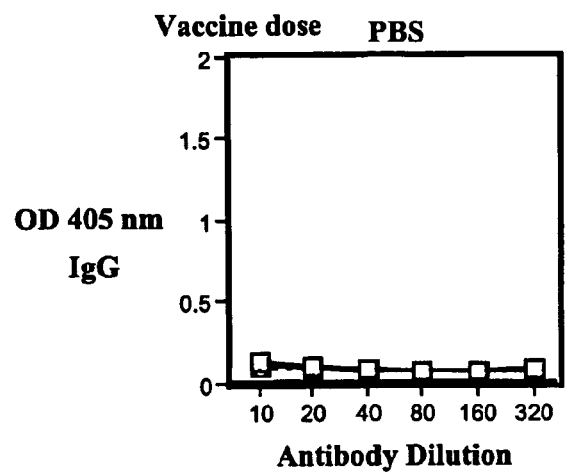
Figure 13F:
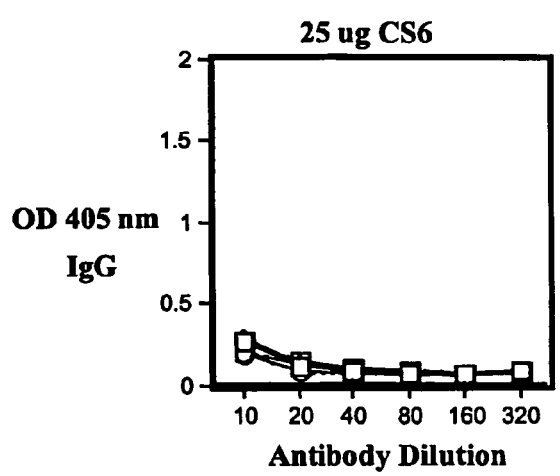
Figure 13G:
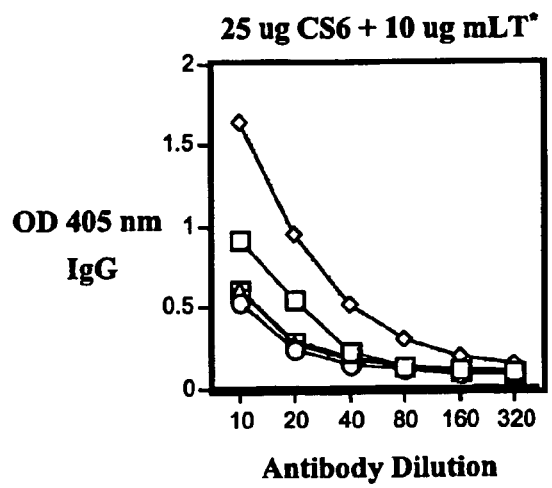
Figure 13H:
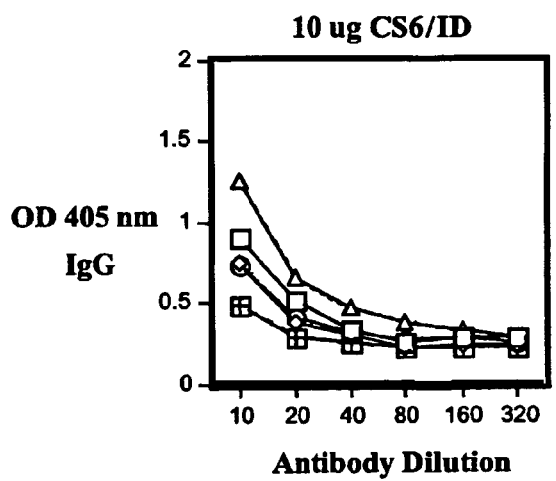
Figure 14A:
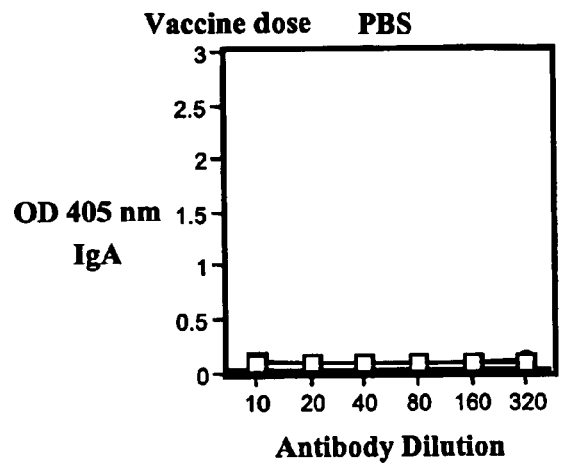
Figure 14B:
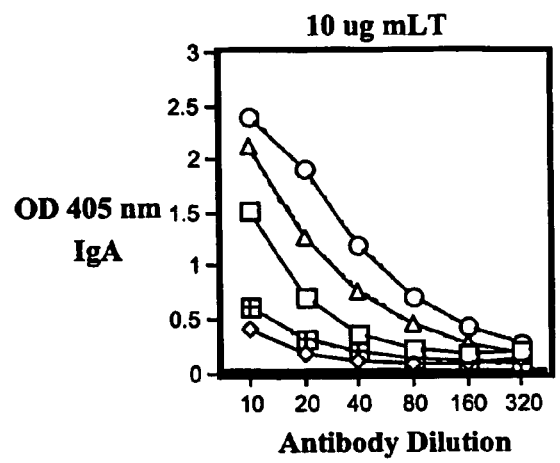
Figure 14C:
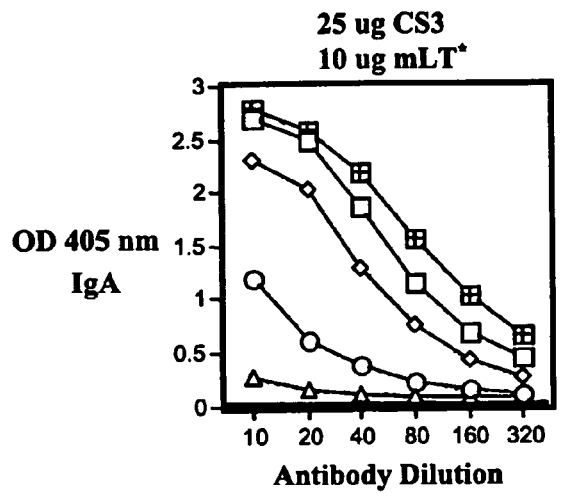
Figure 14D:
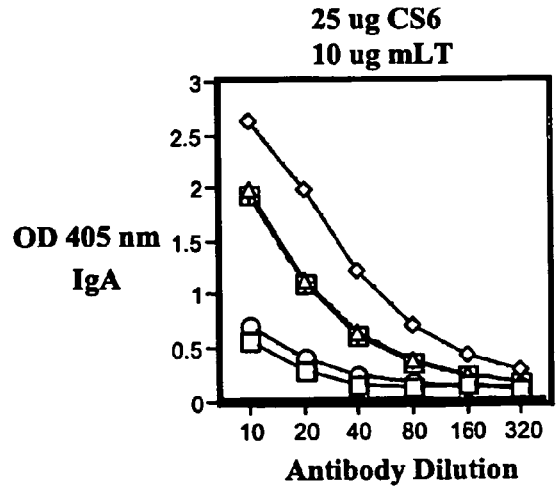
Figure 14E:
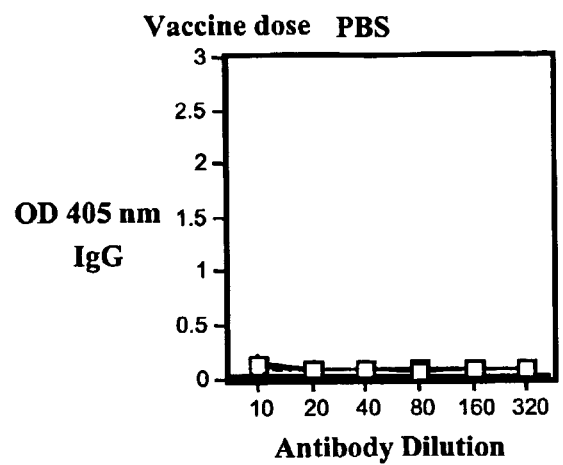
Figure 14F:
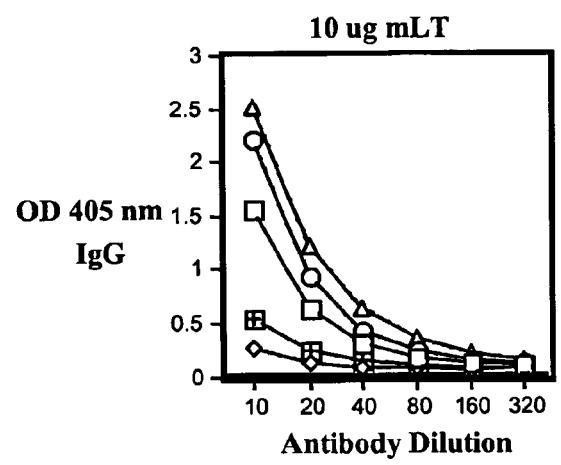
Figure 14G:
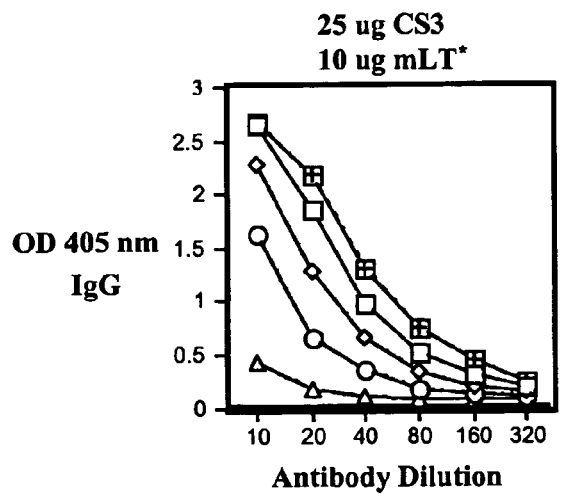
Figure 14H:
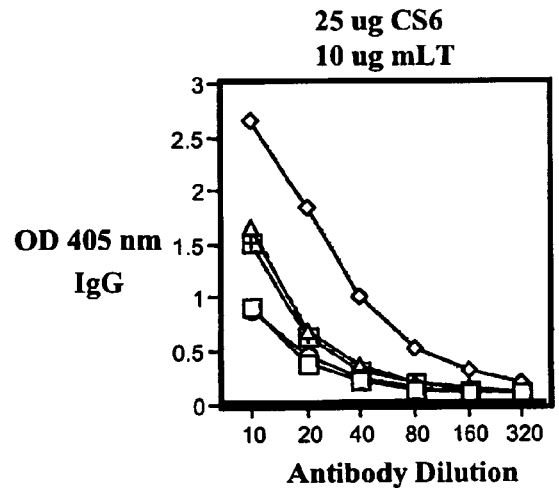
Figure 15A:
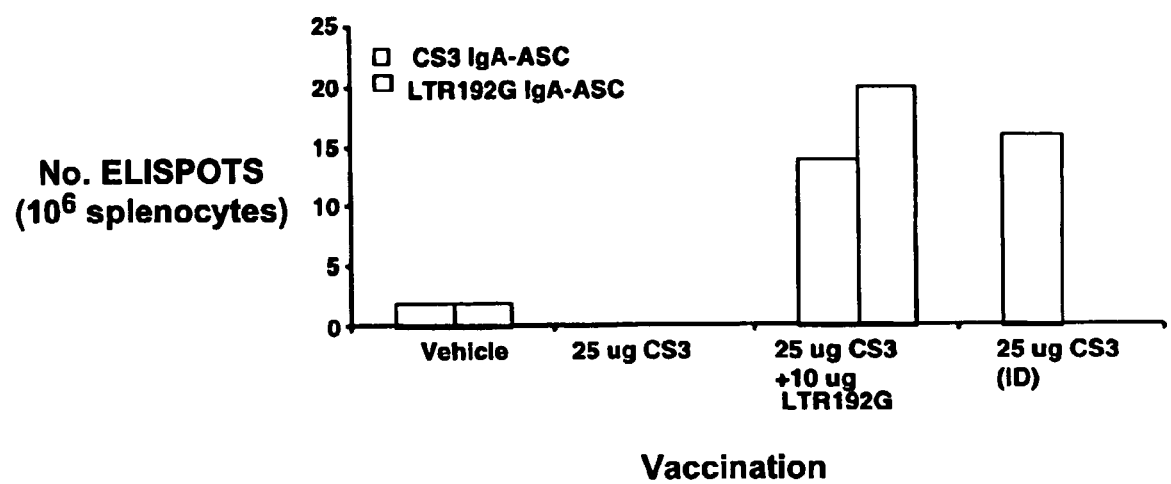
Figure 15B:
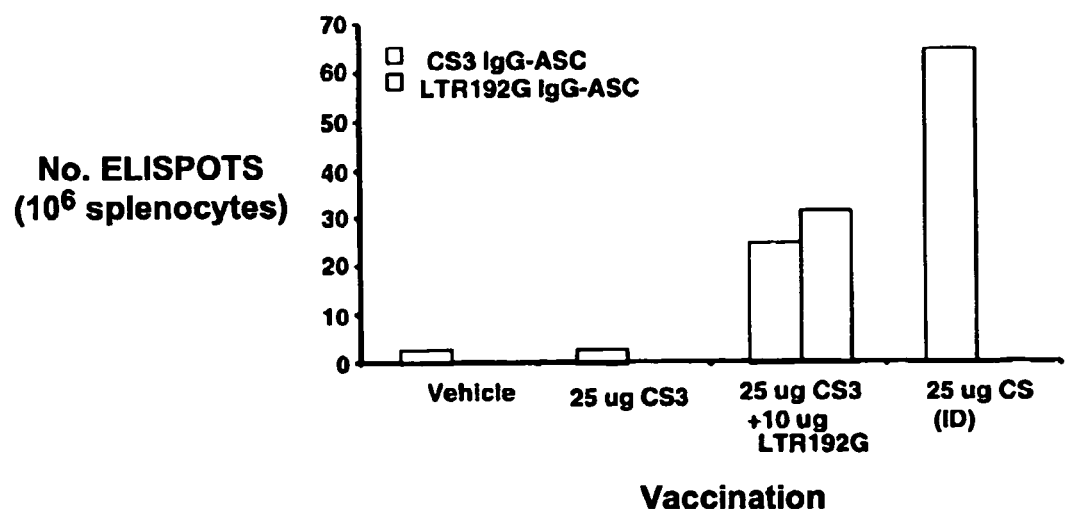
Figure 15C:
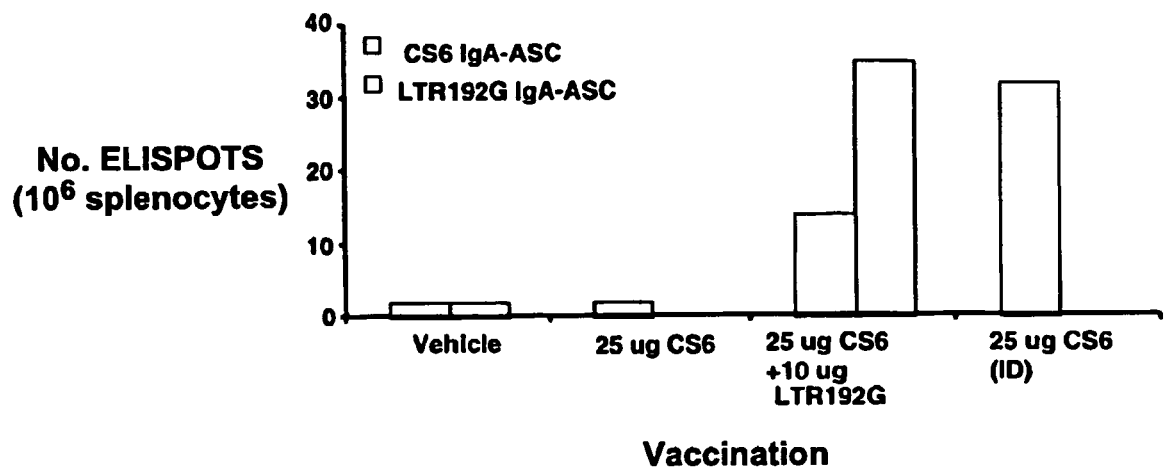
Figure 15D:
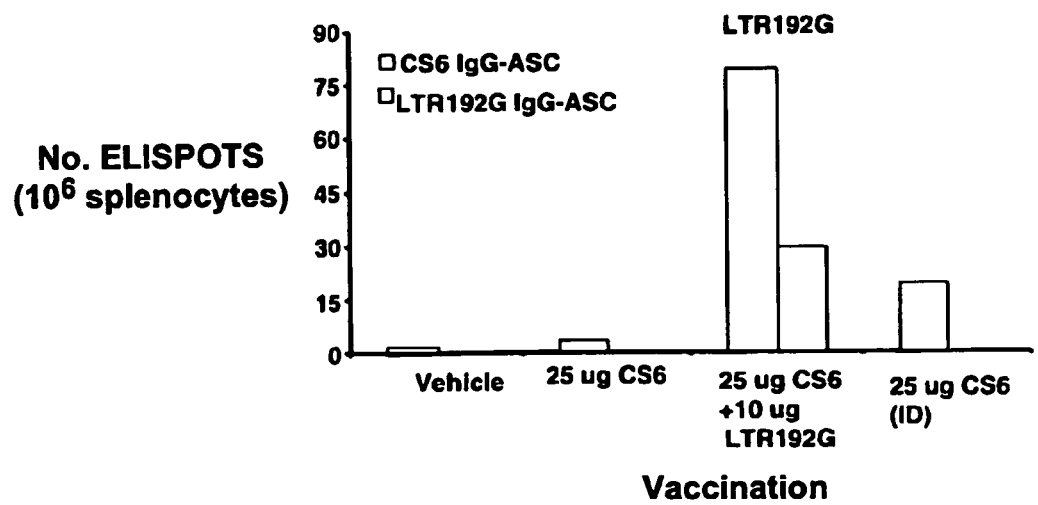

The mucosal (gastrointestinal) immune response elicited by TCI with ETEC subunit vaccines was characterized. A study was conducted to determine if TCI with CS3 with and without the LTR192G would result in the production of antibodies in gastric mucosa. Mice were shaved (48 hr in advance) at the base of the tail, the skin hydrated and tape stripped 10 times. Vaccine-loaded patches were placed over the pretreated skin. Groups of mice received patches with the following formulations: phosphate buffered saline (PBS); 25 µg CS3 alone; and 25 µg CS3/10 µg LTR192G. The patches were applied overnight. A separate group of mice was vaccinated by intradermal injection of 25 µg CS3. All mice received three vaccinations on day 0, 14 and 28. Fresh fecal samples were collected 7 days after the third immunization (day 35). Samples were processed as described in Materials and Methods. Vaccination with CS3 alone did not elicit antigen-specific antibody, with the exception of one animal (FIGS. 12B and C). Mice vaccinated with CS3/LTR192G developed detectable fecal IgG to CS3. Fecal IgA to CS3 was low level (FIGS. 12C and G). Intradermal vaccination with CS3 resulted in measurable fecal IgA and IgG titers to CS3.

Example 10

Mucosal Immune Responses to CS6 Antigen After TCI

Mice were pretreated and immunized as described in Example 9. Groups of mice were transcutaneously vaccinated with patches containing the following formulations: phosphate buffered saline (PBS); 25 µg CS6; and 25 µg CS6 with 10 µg LTR192G. The patches were applied overnight. A separate group of mice was immunized by intradermal injection with 25 µg CS6 alone. All mice received three vaccinations (days 14 and 28) and fecal samples were collected 7 days after the third immunization. These results are shown in FIG. 13. Mice receiving CS6 alone developed little or no detectable fecal IgA or IgG (panels B and F). Mice which were transcutaneously vaccinated with CS6/LTR192G had low-titer, but measurable, CS6-specific IgA (panel C). The CS6-specific IgG was readily detected in samples from all mice (panel G). Mice receiving intradermal CS6 did develop measurable antigen-specific IgA and IgG (panels D and H, respectively).

Example 11

Mucosal Immune Responses to LTR192G Antigen After TCI

Mice were pretreated and immunized as described in Example 9. Groups of mice were transcutaneously vaccinated with patches containing the following formulations: phosphate buffered saline (PBS); 10 µg LTR192G alone; 25 µg CS3/10 µg LTR192G; and 25 µg CS6/10 µg LTR192G. The patches were applied overnight. A separate group of mice was immunized by intradermal injection with 25 μg CS6 alone. All mice received three vaccinations (day 0, 14 and 28) and fecal samples were collected 7 days after the third immunization. These results are shown in FIG. 14. Mice receiving LTR192G alone by TCI developed measurable fecal IgA and IgG (panels B and F). Mice transcutaneously vaccinated with CS3/LTR192G developed measurable LTR192G-specific IgA (panel C) and fecal IgG (panel G). Mice which were transcutaneously vaccinated with CS6/LTR192G developed measurable fecal IgA and IgG to LTR192G (panels D and H). These results support the dual role of the LTR192G in a multivalent ETEC vaccine as a potent adjuvant for boosting systemic and mucosal immune responses to colonization factor antigens and as an vaccine for heat-labile enterotoxin, a toxin responsible for clinical disease.

Example 12

TCI with Divalent ETEC Vaccines Elicits Antigen-Specific Antibody Secreting Cells (ASC) in the Spleen Antigen-specific B cells were next detected in the spleen of vaccinated mice. Mice were pretreated and transcutaneously vaccinated as described in Example 9. Groups of mice were vaccinated with one of the following formulations: 25 μg CS3; 25 μg CS3/10 μg LTR192G; 25 μg CS6; or 25 μg CS6/10 μg LTR192G. The patches were applied overnight to the pretreated skin. Separate groups of mice were vaccinated by intradermal injection at the base of the tail with 25 μg CS3 and 25 μg CS6. All mice received three vaccinations (day 0, 14 and 28). Spleens were collected 30 days after the third immunization (day 58) and single-cell suspensions were prepared and the cells cultured and stained for identification of B cells producing antigen-specific IgG (IgG-ASC) and IgA (IgA-ASC) as described in the Materials and Methods. No IgA- or IgG-ASCs were detected in spleens from mice transcutaneously immunized with CS3 alone (FIG. 15, panels A and B) or CS6 alone (FIG. 15, panels C and D). In contrast, mice transcutaneously immunized with CS3/LTR192G or CS6/LTR192G did develop CS3- and CS6-specific IgA- and IgG-ASCs, indicating that the generation of ASC's in the spleen was dependent upon co-administration of the adjuvant. In addition, LTR192G specific IgA- and IgG-ASC were present in spleen cell suspensions of mice vaccinated with the divalent vaccines (i.e., CS3/LTR192G and CS6/LTR192G). These results demonstrate that the generation of antigen-specific B-cell immunity by TCI is dependent upon co-administration of LTR192G for these antigens.

Example 13

TCI with Trivalent ETEC Vaccine (CS3, CS6 and LTR192G) Elicits Antigen-Specific Antibody Secreting Cells in the Spleen The purpose of this study was to characterize the B-cell response in the spleen after TCI with a trivalent ETEC vaccine. Mice were pretreated and vaccinated as described in Example 12. Mice were vaccinated with patches containing a cocktail of 25 μg CS3/25 μg CS6/10 μg LTR192G. The patches were applied overnight and all mice received three transcutaneous vaccinations (day 0, 14 and 28). Spleens were collected 30 days after the third immunization (day 58). The splenocytes were cultured and antigen-specific ASC stained and counted as described in the Materials and Methods. The results are shown in FIG. 16. Mice vaccinated with the trivalent vaccine (CS3, CS6 and LTR192G) were found to have generated IgA-ASC (panel A) and IgG-ASC (panel B) for each of the ETEC antigens in the vaccine. These results demonstrate that it is feasible to transcutaneously vaccinate with a mixture of ETEC subunit antigens and to elicit clonal expansion of antigen-specific B cells within the spleen.

Example 14

TCI with Monovalent and Divalent ETEC Subunit Vaccines Elicits Antigen Specific Antibody Secreting Cells in Lymph Nodes It was hypothesized that transcutaneous vaccination at the base of the tail may result in clonal expansion of B cells within lymph nodes that drain the dorsal caudal skin surface. To test this hypothesis, mice were epicutaneously immunized at the base of the tail on skin that had been tape stripped 10 times. Groups of mice received three doses of the following formulations: 25 μg CS3; 25 μg CS6; 25 μg CS3/10 μg LTR192G; and 25 μg CS6/10 μg LTR192G. The patches were applied overnight. Separate groups received intradermal injections of 25 μg CS3 or 25 μg CS6. All groups were vaccinated three times (day 0, 12 and 28) and the inginual lymph nodes collected 30 days after the third immunization. Single cell suspensions were prepared and cultured with antigens that were plated onto the microwells. IgG- and IgA-ASC were visualized by staining as described in Materials and Methods. The results shown in FIG. 17 demonstrate that generation of CS3- or CS6-specific IgG-ASC (panels A and B, respectively) was dependent upon co-administration of the adjuvant. It was also observed that CS3, CS6 and LTR192G specific ASC's were more numerous in the inguinal lymph node than in spleen (FIG. 15). This is consistent with the hypothesis that skin immunization likely involves the mobilization and activation of resident skin Langerhans cells to become activated by LTR192G interaction with the GM1 receptor. Antigen loaded and activated Langerhans cells are believed to egress from the epidermis, migrate through the dermis, and into the drain lymphatics. The antigen laden Langerhans cell takes up residence in the lymph node were B cell clonal expansion takes place, hence the relative abundance of CS3, CS6 and LTR192G within the draining inguinal lymph node.

Example 15

Generation of B-Cell Immunity to Complex Mixtures of ETEC Antigens Delivered by TCI We also demonstrate that TCI is suitable for immunizing with a complex mixture of antigens. Mice were pretreated and immunized as described in Example 14. The patch was loaded with a cocktail of three ETEC antigens in the following formulation: 25 μg CS3, 25 μg CS6 and 10 μg LTR192G. After three epicutaneous immunizations, the inguinal lymph nodes were collected and CS3, CS6 and LTR192G specific IgG-ASC was determined. FIG. 18 shows TCI with the trivalent ETEC vaccine did stimulate the generation of ASC specific for each of the subunit antigens in the vaccine.

Example 16

Transcutaneous Vaccination with CFA/I Elicits Systemic Immunity

Having established that it is possible to immunize via the skin with mixtures of high molecular weight antigens, we next investigated the feasibility of TCI with a tetravalent ETEC vaccine. CFA/I is widely expressed by ETEC strains isolated throughout the world. It is estimated that 30% of all human ETEC strains express CFA/I. Initially, we determined if CFA/I was immunogenic when delivered into the skin. In these studies, mice were shaved at the base of the tail, the skin hydrated and gently abraded with emery paper 5 times to disrupt the stratum corneum. The patch was loaded with one of the following formulations: 25 µg CFA/I or 25 µg CFA/I/10 µg LTR192G. The patches were applied overnight. A separate group was immunized by intradermal injection with 25 µg CFA/I. All mice received two doses (day 0 and 14) and serum was collected for analysis 10 days after the second immunization (day 24). As shown in FIG. 19, mice transcutaneously vaccinated with CFA/I did develop serum antibodies after two immunizations (panel A). Co-administration with LTR192G increased the serologic response approximately 8-fold, indicating that LTR192G is a general adjuvant for stimulating immune responses to antigens presented in the skin. As expected, transcutaneously vaccinated mice also developed antibodies to LTR192G (panel B).

Example 17

Transcutaneous Vaccination with CFA/I Elicits Mucosal Immunity

Fresh fecal samples were collected from mice that had been transcutaneously immunized with CFA/I in Example 16. The fecal samples were tested for CFA/I-specific IgA and IgG. As shown in FIG. 20, CFA/I alone did not elicit the generation of detectable fecal IgA (panel B) or fecal IgG (panel F). Mice that received CFA/I and LTR192G did produce fecal IgA (panel C) and IgG (panel G) following vaccination. Interestingly, mice that received CFA/I by intradermal injection did not generate fecal antibodies to the antigen (panels D and H).

Examples 16 and 17 demonstrate that it is feasible to transcutaneously vaccinate with CFA/I and that production of a systemic and mucosal responses that were, to great extent, dependent upon co-administration of the adjuvant.

Example 18

Transcutaneous Vaccination with a Tetravalent ETEC Vaccine Elicits Systemic Immunity Broad coverage by a vaccine to prevent ETEC infection will require the use of a multivalent vaccine. Epidemiology studies demonstrate that a broad coverage (80%-90% of ETEC strains) ETEC vaccine will likely require a combination of at least three colonization factor antigens with *E. coli* heat-labile enterotoxin (LT). The following studies were conducted to demonstrate the feasibility of transcutaneous vaccination with a tetravalent vaccine. Mice were preshaved about 48 hr before TCI and the skin hydrated with 10% glycerol and 70% isopropyl alcohol. The vaccination site was pretreated with emery paper 5 times and the vaccine loaded patch applied to the skin. The formulation used here was 25 µg CFA/I, 25 µg CS3, 25 µg CS6 and 10 µg LTR192G. The mice were vaccinated twice on day 0 and 14 and serum was collected for evaluation 10 days after the second immunization (day 24). The results in FIG. 21 show that all four components of the vaccine elicited serum responses after two immunizations. It should also be pointed out that the LTR192G-adjuvant dose (10 µg) did not need to be increased further in order to achieve immunization. This observation is significant since it clearly indicates that complex mixtures of subunit vaccines can be delivered via the skin and that the adjuvanting activity of the LTR192G does not require further increase in the dose of the adjuvant. Furthermore, the antigenicity of LTR192G was not diminished by co-administration with multiple antigens (CS3, CS6 or CFA/I).

Example 19

Transcutaneous Vaccination with a Tetravalent ETEC Vaccine Elicits Mucosal Immunity to Colonization Factor Antigens Mice were pretreated as described in Example 18. Groups of mice were vaccinated with patches containing the following formulation: 25 µg CFA/I, 25 µg CS3, 25 µg CS6 and 10 µg LTR192G. All mice were transcutaneously vaccinated at the base of the tail on day 0, 14 and 28. Fecal samples were collected two weeks after the third immunization (day 42). The samples were processed and evaluated for antibodies to each of the antigens in the vaccine. The results shown in FIG. 22 demonstrate that fecal IgA and IgG were elicited to CFA/I (panels A and D), CS3 (panels B and E), and CS6 (panels C and F).

Example 20

TCI with a Tetravalent ETEC Vaccine Elicits Anti-Toxin (LT) Immunity

Fecal samples were collected from mice that were vaccinated as in Examples 18 and 19. The samples were processed as described in Materials and Methods and evaluated for fecal IgA and IgG to LTR192G. As shown in FIG. 23, LTR192G elicited significant titers of antigen-specific IgA and IgG antibodies, whether the adjuvant was administered alone (panels A and D), with CFA/I (panels B and E), or as a tetravalent cocktail (panels C and F).

These above examples clearly demonstrate that multivalent vaccines can be efficiently delivered via the skin without the use of a hypodermic needle, jet injector, or other barrier disruptors. These examples also demonstrate the LT adjuvant has a significant role in stimulating the production of high titer serum antibodies; directing the humoral response by mediating the production antigen-specific IgG2a and IgG1; and it is essential in some cases to promoting a mucosal antibody response to ETEC colonization factor antigens. We have demonstrated that multivalent vaccine are effectively delivered by TCI without deleterious competition among the cocktail of antigens. This is important in the treatment of diseases caused by pathogens which express a variety of antigenic specificities because assuring coverage of the many different isolates will probably require including four, five, six, seven, eight or more antigens in a vaccine. Neutralization of toxin and prevention of infection provides treatment (therapeutic and/or prophylactic) at two critical points of host-pathogen interaction. This is an unexpected improvement over the prior art.

Example 21

TCI Elicits Long-Lived Neutralizing Antibodies Against LT

Human volunteers were enrolled into a phase I clinical trial. The volunteers were transcutaneously immunized on the skin over the deltoid muscle. The skin was pretreated with isopropyl alcohol and hydrated with a mixture of 10% glycerol and 70% isopropyl alcohol. A gauze patch (4×4 inches) was affixed to an adhesive backing and an aqueous solution of LT was applied to the patch. The wet patch formulations were in PBS with 5% lactose containing one of the following amounts of LT: 50 µg, 100 µg, 250 µg or 500 µg. The volunteers received two doses (day 0 and 30). Serum was collected prior to immunization (pre-immune) and 312 days after the first immunization (post-immunization). By ELISA, the sera exhibited antibody titers to LTR192G that were above their pre-immune titers (Table 6).

TABLE 6

Detection of serum antibodies after two rounds of TCI

| Volunteer number | Endpoint serum antibody titer to LT (ELISA units[1]) | | LT neutralizing titer in CHO cell culture[2] | | Fold increase in neutralizing antibody (day 312/day 0) |
|---|---|---|---|---|---|
| | Day 0 | Day 312 | Day 0 | Day 312 | |
| 12 | 583 | 10271 | <1:2 | 1:16 | 8 |
| 13 | 1079 | 5098 | <1:2 | 1:16 | 8 |
| 15 | 804 | 13468 | <1:2 | 1:16 | 8 |
| 16 | 1231 | 12317 | <1:2 | 1:8 | 4 |
| 18 | 671 | 18301 | <1:2 | 1:16 | 8 |
| 19 | 730 | 8238 | <1:2 | 1:8 | 4 |

[1]ELISA unit is the endpoint titer that is equal to 1 OD at 405 nm
[2]Lowest serum dilution that blocked (neutralized) CHO cell elongation by >90%

An in vitro CHO cell assay was used to determine if these sera contained antibodies that would neutralize LT receptor binding and in vitro toxicity. All sera were found to have antibodies that blocked (neutralized) LT toxicity in vitro. This result shows that TCI does elicit antibodies that function to neutralize the toxic effects of heat-labile enterotoxin LT on cells. TCI elicits long-lived immunity to LT and the antibodies induced thereby neutralize the toxin.

Example 22

Transcutaneous Vaccination with CS3 and LTR192G Subunit Vaccines Elicit Serum Antibodies that Recognize Antigens on CS3$^+$ETEC Whole Cells We next show that antibodies elicited by transcutaneous vaccination are immunoreactive with native conformational epitopes expressed by enterotoxigenic *E. coli* organism. Mice were pre-shaved and the skin hydrated. The patch was prepared by directly applying an aqueous solution (25 μl) consisting of 25 μg CS3 and 10 μg LTR192G to the gauze patch. While the skin was still hydrated, the patch was applied and maintained in place for ~18 hr. A group of 10 mice received two patches on day 0 and 14. Serum was collected 10 days after the second immunization on day 24. These sera were evaluated by the ELISA method for antibodies to purified CS3, LTR192G and CS3 expressing enterotoxigenic *E. coli* (strain E243778). The results shown in FIG. 24 demonstrate that the immunized mice developed significant antibody titers to purified CS3 (1:70,464) and LTR192G (1:32,657). These sera were also found to have significant serum antibodies titers to ETEC whole cells (1:11,206). These results demonstrate that TCI with ETEC subunit vaccines (e.g., CS3 and LTR192G) does result in the production of antibodies that recognize native conformational determinants on a CS3-expressing ETEC strain.

Example 23

TCI with Killed ETEC Elicits Immunity Against the Bacterial Pathogen

It is feasible to transcutaneously vaccinate with a killed bacterial organism applied to the skin. ETEC (strain E243778) was grown on a bacterial growth media. The bacteria were harvested from the cultures by centrifugation and washed with phosphate buffered saline. A 2% solution of formalin was added to cell pellet and cells suspended to a single cell suspension. The cells were mixed overnight at room temperature in order kill all bacteria. The killed cells were washed and resuspended in PBS. Mice were shaved and the skin at the base of the tail pretreated by tape stripping 10 times to remove the stratum corneum. The gauze patch was loaded with 25 μl volume containing $10^9$ killed ETEC whole cells (EWC) and 10 μg LTR192G was added to the mixture. The patch was applied overnight. A group of 10 animals were vaccinated on day 0 and 14 and the serum collected 10 days after the second immunization. The serum was evaluated for antibodies to EWC and LTR192G using the ELISA method described in Materials and Methods. The results are depicted in FIG. 25. All mice were found to have serologically converted and to have serum antibodies to the bacterial whole cells (1:324) as well as LTR192G (1:21,044). These results are the first demonstration that it is feasible to transcutaneously vaccinate with killed bacterial whole cells and to elicit an organism-specific immune response.

Example 24

TCI with ETEC Colonization Factor, Heat-Labile Enterotoxin (LT), and Heat-Stable Toxin (ST) Antigens Certain strains of enterotoxigenic *E. coli* are known to produce a second enterotoxin called heat-stable enterotoxin (ST). Like the heat-labile enterotoxin (LT), ST is highly reactogenic in humans and it is a cause of severe diarrhea in children and adults. Strains of ETEC may produce STa alone, LT alone, or a combination of STa and LT. STa is a small molecular weight peptide 19 amino acids and contains 6 cysteines. STa is known to poorly immunogenic when administered by injection. This study was conducted to demonstrate that it is possible to transcutaneously deliver a complex ETEC vaccine that consists of multiple colonization factors (CS3 and CS6) and both enterotoxins (LT and ST). Mice were pretreated by tape stripping 10 times at the base of the tail using the method described herein. The patch formulations used here were the following: 25 μg CS3/25 μg CS6; 25 μg CS3/25 μg CS6/10 μg LTR192G; and 25 μg CS3/25 μg CS6/10 μg LTR192G/8 μg ST. Mice received three transcutaneously vaccinations on day 0, 14 and 28 and serum collected two weeks after the third immunization. The results shown in FIG. 26 demonstrate that immunity to the colonization factors was significantly enhanced by addition of LTR192G. This study also demonstrates that the addition of ST can be added to the multivalent ETEC vaccine without adversely affecting the adjuvanting action of LTR192G or the generation of the immune response to these colonization factors. It suggests that it will be possible to develop a pentavalent ETEC vaccine consisting of CS3, CS6, CFA/I, LT and STa or any other combination of antigens. These antigens can be safely administered via TCI without toxicity or serious, adverse side affects.

Example 25

Wet, Protein-In-Adhesive and Air-Dried Patch Formulations for Delivery of ETEC Antigens Patches are versatile vehicles for delivering ETEC vaccines by TCI. Here, LT was formulated in four different ways. First, LT (10 μg) was formulated in an aqueous solution consisting of neutral pH phosphate buffered saline containing 5% (w/v) lactose. This formulation was applied directly to skin hydrated with 10% glycerol and 70% isopropyl alcohol. The solution was left undisturbed or was over laid with a gauze pad for 1 hr. Second, LT was blended with various adhesives (e.g., Klucel). The formulation was then spread as a thin coat over an occlusive backing. The LT was spread with a Rotograveur press as a fine film to an effective concentration of 10 μg in a 1 cm$^2$ area. The film was air-dried at room temperature and moisture content ranged between less than 0.2% to 5% water. Patches (~1 cm$^2$) were punched from the sheet. The patches were stored at ambient temperature and 4° C. exhibited the same delivery characteristics. Third, LT was directly applied to a gauze pad and spread evenly over the surface to a concentration of 10 μg/cm$^2$. These patches were air-dried overnight. Fourth, LT (10 μg in 25 μl PBS and 5% lactose) in an aqueous formulation was dropped directly onto a gauze pad (~1 cm$^2$) that was affixed to an adhesive backing. These patched were air-dried overnight at ambient temperature. These patches were stored at 4° C. for one month prior to use.

The patches were compared for delivery of LT antigen using the mouse model described in Materials and Methods. The shaved skin at the base of the tail was hydrated and pretreated with a pumice-containing swab (formulated with 10% glycerol and 70% isopropyl alcohol) to disrupt the stratum corneum. Groups of 5 mice received two patches: one on day 0 and the other on day 14. The air-dried patch was re-hydrated with 25 μl of water prior to application. The patches were removed after 24 hr. For the liquid formulation, the LT containing solution was left on the skin for 1 hr prior to rinsing with water to remove excess LT. Serum was collected from each animal 2 weeks after the second immunization (day 28). The results are shown in FIG. 27. These results demonstrate that all methods were suitable for transcutaneous delivery of LT across the skin. This example shows that the patch formulation may be an aqueous liquid that is applied directly to skin and over laid with a patch; a dry patch with the antigens incorporated within the adhesive (protein-in-adhesive) and spread as a thin coating over an occlusive backing; a patch in which the antigens are applied in solution (separately or as a cocktail) directly to a suitable surface and allowed to air-dry; or as a hydrated patch in which the antigens are in a solution and the appropriate amount of the solution is directly applied to patch surface shortly before applying the patch.

Example 26

Protein-In-Adhesive Formulations for Transcutaneous Delivery of ETEC Subunit Vaccines and Enterotoxins The protein-in-adhesive formulations are intended to incorporate one or more ETEC subunit antigens into an adhesive formula. The formula is also suitable for incorporating killed ETEC whole cells (~10$^4$ to 10$^8$ killed bacteria per dose) with or without LT-adjuvant. The blend is then cast over a sheet of occlusive (or semi-occlusive) backing as a thin film. The vaccine/adhesive mixture is allowed to cure (room temperature or 40° C.) until the film is dry (water content may vary between 0.5% and 5%; 1-2% is desired). The cast film is cut from the die-cast to the desired size and shape. The dry patches are then sealed in a light-tight, waterproof plastic or foil pouch. Patches produced in this manner may be stored refrigerated or at ambient temperatures. The protein-in-adhesive is flexible in that the multivalent vaccine blend may be varied to incorporate different amounts and ratios of one or multiple antigens and adjuvant. In addition, the patch size may be varied in order to adjust dosing. Depending upon the age of the individual, patch size (dose) can be varied for use in children and adults.

Protein-in-adhesive formulations are flexible and uniquely allow the vaccines to be coated in layers. These patches are manufactured in a manner wherein each vaccine component is layered separately onto the patch backing. The objective is to create a multilaminar membrane were component 1 is layered onto the backing, component 2 film is layered over 1, component 3 is layered on top of components 1 and 2, and component 4 is the outermost layer. The advantage of this approach is that it provides flexibility to the formulation (i.e., patches may be produced from the same process using different ratios of antigen and adjuvant or in the case were the vaccine is manufactured to contain only one or two components). This multilayered formula also has the advantage of controlling the release rates of each antigen and the adjuvant. In some instances, it will be desirable to have the LT-adjuvant released immediately in order to pre-prime the skin dentritic cells (Langerhans cells) prior to release of other antigens. In such formulations, the LT-primed Langerhans cells may more efficiently capture and process the toxin and colonization factor antigens. Controlled delivery is a more efficient use of the adjuvant and antigens and will allow the doses to be further reduced.

Tables 7-8 describe formulations that may be suitable for stabilizing adjuvants and/or antigens into an adhesive. The following are intended to be examples of such formulations and are not intend to restrict the formulation.

TABLE 7

Eudragit EPO formulation

| Ingredients | % NVC | Wt (gm) | Wt (%) | Dry Wt (gm) | % (w/w) |
|---|---|---|---|---|---|
| EPO polymer | 100 | 22.8 | 22.0 | 22.8 | 58.8 |
| Succinic acid | 100 | 1.0 | 1.0 | 1.0 | 2.6 |
| ATBC | 100 | 15.0 | 14.5 | 15.0 | 38.7 |
| Water | 0 | 55.0 | 62.6 | 0 | 0 |
| Totals | | 104 | 100 | 38.8 | 100 |

TABLE 8

Adhesive formulation with *E. coli* CS6 and LT

| | | Wet Weight | | | | |
|---|---|---|---|---|---|---|
| Ingredients | % NVC | g (nat/water) | g (nat only) | Wet % | Dry Wt (gm) | Dry (% w/w) |
| 1 × PBS | 6.0 | 15.6 | 15.6 | 38.2 | 0.9 | 13.3 |
| EPO | 37.5 | 15.6 | 15.6 | 38.2 | 5.9 | 82.3 |

TABLE 8-continued

Adhesive formulation with E. coli CS6 and LT

| | | Wet Weight | | | | |
|---|---|---|---|---|---|---|
| Ingredients | % NVC | g (nat/water) | g (nat only) | Wet % | Dry Wt (gm) | Dry (% w/w) |
| Natrasol | 2.5 | 9.0 | 0.2 | 22.4 | 0.2 | 3.2 |
| CS6 | 100 | 0.05 | 0.05 | 0.12 | 0.05 | 0.66 |
| LT | 100 | 0.02 | 0.01 | 0.04 | 0.02 | 0.2 |
| Tween 20 | 100 | 0.03 | 0.03 | 0.07 | 0.03 | 0.4 |

Example 27

Gel Formulations for Delivery of ETEC Subunit Vaccines (CS3, CS6, CFA/I, ST and LT) and Killed ETEC Whole Cells Gels are examples of fully hydrated or wet patches. These formulations are intended to incorporate one or more ETEC subunit antigens entrapped within a gel matrix. This formulation is also suitable for transcutaneous delivery of killed ETEC whole cells ($\sim 10^4$ to $10^8$ killed bacteria per dose) with or without LT. The vaccines are formulated by blending a solution containing the antigens in the desired amounts and ratios with a carbomer, pluronic, or a mixture of the two gel components (see below). The gel containing vaccine is then coated onto a strip of the material that holds the gel in-place without spilling. It is important that the material have a low binding capacity for the proteins in the vaccine. The strip may comprise materials such as polymers, natural and synthetic wovens, non-wovens, foil, paper, rubber, or combinations thereof. The strip may be a single layer or a laminate of more than one layer. Generally, the strip is substantially water impermeable and helps to maintain the skin in hydrated condition. The material may be any type of polymer that meets the required flexibility and low binding capacity for proteins. Suitable polymers include, but are not limited to, polyethylene, ethyl vinylacetate, ethylvinyl alcohol, polyesters, or Teflon. The strip of material for holding the gel is less than 1 mm thick, preferably less than 0.05 mm thick, most preferably 0.001 to 0.03 mm thick.

The gel-loaded strip may be of different sizes and shapes. It is preferred that the corners be rounded for ease of application-. The length of the strip can vary and is dependent upon the intended user (i.e., children or adults). It may be from about 2 cm to about 12 cm, and is preferably from about 4 cm to about 9 cm. The width of the strip will vary but it may be from about 0.5 cm to about 4 cm.

The strip may contain shallow pockets or dimples. To hold in place, when the vaccine containing gel is coated onto the strip, the gel should fill the shallow pockets that provide reservoirs for the gel. The shallow pockets may be about 0.4 mm across and about 0.1 mm deep. The gel-loaded patch is about 1 mm thick, with a preferred thickness of about 0.5 mm or less.

The flexural stiffness is important since maximal contact between the gel and the skin must be maintained. The strip will need to conform to the contour of the anatomical location where the patch is applied (e.g., skin over the deltoid muscle, volar forearm, neck, behind the ear, or other locations). Flexural stiffness can be measured with a Handle-O-Meter (Thwing Albert Instruments). The flexural stiffness should be less than 5 gm/cm, more preferably less than 3 gm/cm. The relatively low stiffness enables the strip of material to drape over the contoured surface with little force being exerted.

The gel-loaded strip is held in place by affixing the strip to an adhesive backing with the gel surface facing away from the adhesive backing. The backing material may be occlusive or semi-occlusive (e.g., TEGADERM). The backing is designed to hold the patch in place, to aid in maintaining maximal contact between the skin and gel, and to prevent the gel from dehydrating during wear.

To prevent dehydration of the wet patch during storage and handling, it may be placed on an inert plastic strip, which is fairly rigid. The gel surface would be in direct contact with the plastic strip, and the gel/plastic interface has low peel force making it easy to separate the gel strip from the plastic strip. The plastic strip may be made of polyethylene or similar material. The gel-patch can be packaged in a light-proof and water tight plastic or foil pouch. The pouch can be stored refrigerated or at room temperature.

The following are intended as examples of the hydrated gel formulation and are not intended to restrict it: gels in phosphate buffered saline; 1% CARBOMER 1342; 1.5% CARBOMER 940; 1.5% CARBOMER 934; 1.5% CARBOMER 940, 2% sucrose, 10% isopropyl alcohol, 10% glycerol; 50% PLURONIC F87; and 30% PLURONIC F108.

Carbomer polymers are high molecular weight, acrylic acid-based polymers that may be cross-linked with allyl sucrose or allylpentaerythritol, and/or modified with C10-C30 alkyl acrylates. These may or may not be incorporated into a patch or may be delivered by other means know in the art into the skin.

Formulations may be comprised of carbomers of different average molecular weights. For example, the polymers may be CARBOMER 1342 (e.g., 1% CARBOMER 1342, 0.6 mg/ml LT, 0.3% methylparaben, 0.1% propylparaben, 2.5% lactose, 1× PBS); CARBOMER 940 (e.g., 1.5% CARBOMER 940, 0.6 mg/ml LT, 0.3% methylparaben, 0.1% propylparaben, 2.5% lactose, 1× PBS). Each formulation can be prepared in a phosphate buffered saline solution and contain LT at a concentration of about 0.6 mg/ml or less, but antigens and adjuvants may also be formulated from about 0.001 mg/ml to about 0.6 mg/ml or from about 0.6 mg/ml to about 6 mg/ml. In addition, antimicrobial agents such as methylparaben and propylparaben may be included.

Combinations of CARBOMER 940 and PLURONIC F87 (e.g., 1.5% CARBOMER 940, 0.5% PLURONIC F87, 0.6 mg/ml LT, 0.3% methylparaben, 0.1% propylparaben, 2.5% lactose, 1× PBS) may be used. PLURONICS are another class of hydrogel that contain repeating segments of ethylene oxide-propylene oxide-ethylene oxide. The amount of LT and antimicrobial agents in the formulation may be identical.

Other formulations may enhance delivery using penetration enhancers and carbomers. For example, a gel may comprise CARBOMER 940 with PHARMASOLVE (e.g., 1.5% CARBOMER 940, 10% PHARMASOLVE, 0.6 mg/ml LT, 0.3% methylparaben, 0.1% propylparaben, 2.5% lactose, 1× PBS) while the final gel may contain CARBOMER 940, glycerol, and isopropanol (e.g., 1.5% CARBOMER 940, 10% glycerol, 10% isopropanol, 0.6 mg/ml LT, 0.3% methylparaben, 0.1% propylparaben, 2.5% lactose, 1× PBS). The concentration of LT and antimicrobial agents may remain identical to the previous formulations, or may be in other ranges specified.

Example 28

Dosages for CS3, CS6, CFA/I, ST and LT

The dose range may vary and may be dependent upon the age and medical condition of the subject. Doses of 1 mg to less than 5 µg may elicit antigen-specific immune responses in both human and animal subjects. The desired adult dose may range for colonization factors from about 1 µg to about 100 µg of each (e.g., CS3, CS6 and CFA/I); the preferred dose of each colonization factor is from about 5 µg to about 50 µg. The desired adult dose may range for LT from about 1 µg to about 100 µg; the preferred dose of LT is from about 5 µg to about 50 µg. The desired adult dose may range for ST (not conjugated to a carrier protein) from about 1 µg to about 100 µg. Since ST is poorly immunogenic, the adult dose may be from about 25 µg to about 100 µg. If ST is chemically coupled to LT (LT-ST), the ST equivalent dose may be from about 5 µg to about 50 µg. Immunogenicity can be improved by conjugating ST to other carrier proteins, including, for example, albumins, KLH or aggregated antibodies. In this latter case, the dose of ST may be from about 5 µg to about 50 µg.

REFERENCES

Ahren et al. (1998) Intestinal immune responses to an inactivated oral enterotoxigenic *Escherichia coli* vaccine and associated immunoglobulin A responses in blood, Infect Immun., 66:3311-3316.

Beebe et al. (1972) Long-term mortality follow-up of Army recruits who received adjuvant influenza virus vaccine in 1951-1953, Am J Epidemiol, 95:337-346.

Beignon et al. (2001) Immunization onto bare skin with heat-labile enterotoxin of *Escherichia coli* enhances immune responses to coadministered protein and peptide antigens and protects mice against lethal toxin challenge, Immunol, 102:344-351.

Berardesca & Maibach (1988) Contact dermatitis in blacks, Dermatol Clin, 6:363-368.

Black (1993) Epidemiology of diarrhoeal disease: Implications for control by vaccines, Vaccine, 11:100-106.

Caeiro et al. (1999) Improved detection of enterotoxigenic *Escherichia coli* among patients with travelers' diarrhea, by use of the polymerase chain reaction technique, J Infect Dis, 180:2053-2055.

Cassels & Wolf (1995) Colonization factors of diarrheagenic *E. coli* and their intestinal receptors, J Industr Microbiol, 15:214-226.

Cassels et al. (1992) Analysis of *Escherichia coli* colonization factor antigen I linear B-cell epitopes, as determined by primate responses, following protein sequence verification, Infect Immun, 60:2174-2181.

Cheney et al. (1980) Species specificity of in vitro *Escherichia coli* adherence to host intestinal cell membranes and its correlation with in vivo colonization and infectivity, Infect Immun, 28:1019-1027.

Clemens et al. (1988) Cross-protection by B subunit-whole cell cholera vaccine against diarrhea associated with heat-labile toxin-producing enterotoxigenic *Escherichia coli*: results of a large-scale field trial, J Infect Dis, 158:372-377.

Clements et al. (1980) Properties of homogeneous heat-labile enterotoxin from *Escherichia coli*, Infect Immun, 29:91-97.

Clements et al. (1988) Adjuvant activity of *Escherichia coli* heat-labile enterotoxin and effect on the induction of oral tolerance in mice to unrelated protein antigens, Vaccine, 6:269-277.

Cohen et al. (2000) Safety and immunogenicity of two different lots of the oral, killed enterotoxigenic *Escherichia coli*-cholera toxin B subunit vaccine in Israeli young adults, Infect Immune 68:4492-4497.

Craig (1966) Preparation of the vascular permeability factor of *Vibrio cholerae*, J Bacteriol, 92:793-795.

Cravioto et al. (1990) Risk of diarrhea during the first year of life associated with initial and subsequent colonization by specific enteropathogens, Am J Epidemiol, 131:886-904.

Crottet et al. (1999) Expression, purification and biochemical characterization of recombinant murine secretory component: a novel tool in mucosal immunology, Biochem J, 341:299-306.

Cryz & Gluck (1998) Immunopotentiating reconstituted influenza virosomes as a novel antigen delivery system, Dev Biol Stand, 92:219-223.

Czerkinsky et al. (1988) A novel two colour ELISPOT assay. I. Simultaneous detection of distinct types of antibody-secreting cells, J Immunol Meth, 115:31-37.

Daniels et al. (2000) Traveler's diarrhea at sea: Three outbreaks of waterborne enterotoxigenic *Escherichia coli* on cruise ships, J Infect Dis, 181:1491-1495.

Division of Health Promotion and Disease Prevention and Division of International Health, I.O.M. (1986) The prospects for immunizing against *Escherichia coli* (ETEC), pp.178-185, *New Vaccine Development: Establishing Priorities*, vol. 2, National Academy Press, Washington, D.C.

Edelman (1980) Vaccine adjuvants, Rev Infect Dis, 2:370-383.

El-Ghorr et al. (2000) Transcutaneous immunisation with herpes simplex virus stimulates immunity in mice, FEMS Immunol Med Microbiol, 29:255-261.

Evans et al. (1977) Hemagglutination of human group A erythrocytes by enterotoxigenic *Escherichia coli* isolated from adults with diarrhea: correlation with colonization factor, Infect Immun, 18:330-337.

Evans et al. (1988) Non-replicating oral whole cell vaccine protective against enterotoxigenic *Escherichia coli* (ETEC) diarrhea: stimulation of anti-CFA (CFA/I) and anti-enterotoxin (anti-LT) intestinal IgA and protection against challenge with ETEC belonging to heterologous serotypes, FEMS Microbiol Immunol, 1:117-125.

Forrester & Ury (1969) The Signed-Rank (Wilcoxon) test in the rapid analysis of biological data, Lancet, 1:239-241.

Freedman et al. (1998) Milk immunoglobulin with specific activity against purified colonization factor antigens can protect against oral challenge with enterotoxigenic *Escherichia coli*, J Infect Dis, 177:662-667.

Freytag & Clements (1999) Bacterial toxins as mucosal adjuvants, Curr Topics Microbiol Immunol, 236:215-236.

Fujita & Finkelstein (1972) Antitoxic immunity in experimental cholera: a comparison of immunity induced perorally and parenterally in mice, J Infect Dis, 125:647-655.

Gilligan (1999) *Escherichia coli*. EAEC, EHEC, EIEC, ETEC, Clin Lab Med, 19:505-521.

Glenn et al. (1998a) Skin immunization made possible by cholera toxin, Nature, 391:851.

Glenn et al. (1998b) Transcutaneous immunization with cholera toxin protects mice against lethal mucosal toxin challenge, J Immunol, 161:3211-3214.

Glenn et al. (1999) Transcutaneous immunization with bacterial ADP-ribosylating exotoxins as antigens and adjuvants, Infect Immun, 67:1100-1106.

Glenn et al. (2000) Transcutaneous immunization: A human vaccine delivery strategy using a patch, Nat Med, 6:1403-1406.

Gockel et al. (2000) Transcutaneous immunization induces mucosal and systemic immunity: A potent method for targeting immunity to the female reproductive tract, Mol Immunol, 37:537-544.

Hall et al. (2001) Induction of systemic antifimbria and antitoxin antibody responses in Egyptian children and adults by an oral, killed enterotoxigenic *Escherichia coli* plus cholera toxin B subunit vaccine, Infect Immun, 69:2853-2857.

Hammond et al. (2000) Transcutaneous immunization of domestic animals: opportunities and challenges, Adv Drug Delivery Rev, 43:45-55.

Hammond et al. (2001) Transcutaneous immunization: T cell responses and boosting of existing immunity, Vaccine, 19:2701-2707.

Harlow & Lane (1988) *Antibodies: A laboratory manual.* Cold Spring Harbor Press.

Hartman et al. (1994) Local immune response and protection in the guinea pig keratoconjunctivitis model following immunization with Shigella vaccines, Infect Immun, 62:412-420.

Hartman et al. (1999) Native and mutant forms of cholera toxin and heat-labile enterotoxin effectively enhance protective efficacy of live attenuated and heat-killed Shigella vaccines, Infect Immun, 67:5841-5847.

Helander et al. (1997) Binding of enterotoxigenic *Escherichia coli* to isolated enterocytes and intestinal mucus, Microb Pathogen, 23:335-346.

Helander et al. (1998) Antibody responses in humans against coli surface antigen 6 of enterotoxigenic *Escherichia coli*, Infect Immun, 66:4507-4510.

Hoffman et al. (1994) Safety, immunogenicity, and efficacy of a malaria sporozoite vaccine administered with monophosphoryl lipid A, cell wall skeleton of mycobacteria, and squalane as adjuvant, Am J Trop Med Hyg, 51:603-612.

Hoge et al. (1998) Trends in antibiotic resistance among diarrheal pathogens isolated in Thailand over 15 years, Clin Infect Dis, 26:341-345.

Huerta et al. (2000) A waterborne outbreak of gastroenteritis in the Golan Heights due to enterotoxigenic *Escherichia coli,* Infect, 28:267-271

Hyams et al. (1991) Diarrheal disease during Operation Desert Shield, N Engl J Med, 325:1423-1428.

Jacobs et al. (1982) Adverse reactions to tetanus toxoid, JAMA, 247:40-42.

Jertborn et al. (1986) Saliva, breast milk, and serum antibody responses as indirect measures of intestinal immunity after oral cholera vaccination or natural disease, J Clin Microbiol, 24:203-209.

Jertborn et al. (1998) Safety and immunogenicity of an oral inactivated enterotoxigenic *Escherichia coli* vaccine, Vaccine, 16:255-260.

Jertborn et al. (2001) Dose-dependent circulating immunoglobulin A antibody-secreting cell and serum antibody responses in Swedish volunteers to an oral inactivated enterotoxigenic *Escherichia coli* vaccine, Clin Diag Lab Immunol, 8:424-428.

Jiang et al. (2000) Characterization of enterotoxigenic *Escherichia coli* strains in patients with travelers' diarrhea acquired in Guadalajara, Mexico, 1992-1997, J Infect Dis, 181:779-782.

Jodar et al. (2001) Ensuring vaccine safety in immunization programmes—a WHO perspective, Vaccine, 19:1594-1605.

Keitel et al. (1993.) Pilot evaluation of influenza virus vaccine (IVV) combined with adjuvant, Vaccine, 11:909-913.

Levine (1981) Adhesion of enterotoxigenic *Escherichia coli* in humans and animals, Ciba Found Symp, 80:142-60.

Levine (1983) Travellers' diarrhoea: prospects for successful immunoprophylaxis, Scand J Gastroenterol—Suppl, 84:121-134.

Levine et al. (1979) Immunity to enterotoxigenic *Escherichia coli,* Infect Immun, 23:729-736.

Levine et al. (1983) New knowledge on pathogenesis of bacterial enteric infections as applied to vaccine development, Microbiol Rev, 47:510-550.

Lycke (1997) The mechanism of cholera toxin adjuvanticity, Res Immunol, 148:504-520.

Mattila et al. (1992) Seasonal variation in etiology of travelers' diarrhea. Finnish-Moroccan Study Group, J Infect Dis, 165:385-388.

Michetti et al. (1999) Oral immunization with urease and *Escherichia coli* heat-labile enterotoxin is safe and immunogenic in *Helicobacter pylori*-infected adults, Gastroenterol, 116:804-812.

Murphy et al. (2001) Treatment of traveler's diarrhea, pp. 165-176. In H. L. DuPont, Stephen, R. (ed.), Texbook of travel medicine and health. Books News Inc., Portland.

Nagy & Fekete (1999) Enterotoxigenic *Escherichia coli* (ETEC) in farm animals. Vet. Res. 30:259-284.

Orndorff et al. (1996) Enterotoxigenic *Escherichia coli* diarrhea in children less than five years of age in central Java, Am J Trop Med Hyg, 55:449-451.

Pierce & Reynolds (1974) Immunity to experimental cholera. I. Protective effect of humoral IgG antitoxin demonstrated by passive immunization, J Immunol, 113:1017-1023.

Pierce & Reynolds (1974) Immunity to experimental cholera. I. Protective effect of humoral IgG antitoxin demonstrated by passive immunization, J Immunol, 113:1017-1023.

Pierce et al. (1972) Protection against experimental cholera by antitoxin, J Infect Dis, 126:606-616.

Pierce et al. (1980) Antitoxic immunity to cholera in dogs immunized orally with cholera toxin, Infect Immun, 27:632-637.

Qadri et al. (2000) Safety and immunogenicity of an oral, inactivated enterotoxigenic *Escherichia coli* plus cholera toxin B subunit vaccine in Bangladeshi adults and children, Vaccine, 18:2704-2712.

Richardson et al. (1984) Sealed adult mice: new model for enterotoxin evaluation, Infect Immun, 43:482-486.

Sack et al. (1984) Doxycycline prophylaxis of travelers' diarrhea in Honduras, an area where resistance to doxycycline is common among enterotoxigenic *Escherichia coli,* Am J Trop Med Hyg, 33:460-466.

Sahai & Khurshid (1995) On analysis of epidemiological data involving a 2×2 contingency table: an overview of Fisher's exact test and Yates' correction for continuity, J Biopharm Stat, 5:43-70.

Savarino et al. (1998) Safety and immunogenicity of an oral, killed enterotoxigenic *Escherichia coli*-cholera toxin B subunit vaccine in Egyptian adults, J Infect Dis, 177:796-799.

Savarino et al. (1999) Oral, inactivated, whole cell enterotoxigenic *Escherichia coli* plus cholera toxin B subunit vaccine: results of the initial evaluation in children. PRIDE Study Group, J Infect Dis, 179:107-114.

Schagger & von Jagow (1987) Tricine-sodium dodecyl sulfate-polyacrylamide gel electrophoresis for the separation of proteins in the range from 1 to 100 kDa, Anal Biochem, 166:368-379.

Scharton-Kersten et al. (2000) Transcutaneous immunization with bacterial ADP-ribosylating exotoxins, subunits, and unrelated adjuvants, Infect Immun, 68:5306-5313.

Schultsz et al. (2000) Diarrheagenic *Escherichia coli* and acute and persistent diarrhea in returned travelers, J Clin Microbiol, 38:3550-3554.

Schultz et al. (1995) Effect of DETOX as an adjuvant for melanoma vaccine, Vaccine, 13:503-508.

Scott et al. (1990) Norfloxacin for the prophylaxis of travelers' diarrhea in U.S. military personnel, Am J Trop Med Hyg, 42:160-164.

Stoll et al. (1986) Local and systemic antibody responses to naturally acquired enterotoxigenic *Escherichia coli* diarrhea in an endemic area, J Infect Dis, 153:527-534.

Svennerholm et al. (1983) Serologic differentiation between antitoxin responses to infection with *Vibrio cholerae* and enterotoxin-producing *Escherichia coli,* J Infect Dis, 147:514-522.

Tacket et al. (1988) Protection by milk immunoglobulin concentrate against oral challenge with enterotoxigenic *Escherichia coli,* New Engl J Med, 318:1240-1243.

Tacket et al. (1994) Enteral immunization and challenge of volunteers given enterotoxigenic *E. coli* CFA/II encapsulated in biodegradable microspheres, Vaccine, 12:1270-1274.

Tacket et al. (1999) Lack of prophylactic efficacy of an enteric-coated bovine hyperimmune milk product against enterotoxigenic *Escherichia coli* challenge administered during a standard meal, J Infect Dis, 180:2056-2059.

Taylor et al. (1985) Polymicrobial aetiology of travellers' diarrhoea, Lancet. 1:381-383.

Todd (1997) Epidemiology of foodborne diseases: A worldwide review, World Health Statistics Quarterly, 50:30-50.

Trach et al. (1997) Field trial of a locally produced, killed, oral cholera vaccine in Vietnam, Lancet, 349:231-235.

Vassell et al. (1999) Activation of Langerhans cells following transcutaneous immunization, pg. 13. The 5th National Symprosium, Basic Aspects of Vaccines, Bethesda, Md.

Wenneras et al. (1992) Antibody-secreting cells in human peripheral blood after oral immunization with an inactivated enterotoxigenic *Escherichia coli* vaccine, Infect Immun, 60:2605-2611.

Wolf (1997) Occurrence, distribution, and associations of O and H serogroups, colonization factor antigens, and toxins of enterotoxigenic *Escherichia coli.* Clin. Microbiol Rev, 10:569-584.

Wolf (1997) Occurrence, distribution, and associations of O and H serogroups, colonization factor antigens, and toxins of enterotoxigenic *Escherichia coli,* Clin Microbiol Rev, 10:569-584.

Wolf et al. (1993) Characterization of enterotoxigenic *Escherichia coli* isolated from U.S. troops deployed to the Middle East. J Clin Microbiol, 31:851-856.

Wolf et al. (1997) The CS6 colonization factor of human enterotoxigenic *Escherichia coli* contains two heterologous major subunits. FEMS Microbiol Lett, 148:35-42.

Wolf et al. (1997) U.S. Pat. No. 5,698,416. Methods for production of antigens under control of temperature-regulated promoters in enteric bacteria. Walter Reed Army Institute of Research.

Wolf et al. (1999) Use of the human challenge model to characterize the immune response to the colonization factors of enterotoxigenic *Escherichia coli* (ETEC) The 35th Joint Conference of the U.S.-Japan Cooperative Medical Science Program, Tokyo, Japan.

Wood et al. (1983) Antimicrobial resistance of gram-negative bacteria isolated from foods in Mexico, J Infect Dis, 148:766.

Yu, J., F. J. Cassels, T. Scharton-Kersten, S. A. Hammond, A. Hartman, E. Angov, C. Corthesy, C. R. Alving, and G. M. Glenn Transcutaneous immunization using colonization factor and heat labile enterotoxin induces correlates of protective immunity for enterotoxigenic *Escherichia coli.* Infect Immun, in press.

All references (e.g., articles, books, patents, and patent applications) cited above are indicative of the level of skill in the art and are incorporated by reference.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. No particular relationship between or among limitations of a claim is meant unless such relationship is explicitly recited in the claim (e.g., the arrangement of components in a product claim or order of steps in a method claim is not a limitation of the claim unless explicitly stated to be so). Thus, all possible combinations and permutations of the individual elements disclosed herein are intended to be considered part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification

We claim:

1. A method of preventing traveler's diarrhea in a human that is to be subjected to exposure to pathogens causing traveler's diarrhea comprising applying a vaccine transcutaneously to the skin of the human, prior to exposure to pathogens causing traveler's diarrhea, wherein the vaccine comprises an effective amount of heat-labile enterotoxin of *E. coli* (LT) to prevent traveler's diarrhea.

2. A method of preventing traveler's diarrhea in a human that is to be subjected to exposure to pathogens causing traveler's diarrhea comprising applying a vaccine transcutaneously to the skin of the human, prior to exposure to pathogens causing traveler's diarrhea, wherein the vaccine comprises an effective amount of heat-labile enterotoxin of *E. coli* (LT) to treat traveler's diarrhea.

3. The method of claim 1 or 2, wherein the vaccine comprises LT and an adjuvant.

4. The method of claim 3, wherein the adjuvant is an ADP-ribosylating exotoxin or a derivative thereof having adjuvant activity.

5. The method of claim 1 or 2, wherein the vaccine comprises LT and an *E. coli* colonization factor antigen (CFA).

6. The method of claim 5, wherein the *E. coli* colonization factor antigen is selected from the group consisting of CFA/I, CS1, CS2, CS 4, CS5, CS6, CS17 and PCF 0166.

7. The method of claim 1, wherein the vaccine comprises LT and heat stable enterotoxin of *E. coli* (ST).

8. The method of claim 7, wherein the vaccine comprises a carrier or an excipient.

9. The method of claim 7, wherein LT is conjugated to ST.

10. The method of claim 1, wherein the method comprises pretreating the skin prior to administering the vaccine.

11. The method of claim 10, wherein pretreating comprises chemical penetration enhancement, physical penetration enhancement, or both.

12. The method of claim 1 or 2, wherein the vaccine is applied using a patch.

13. The method of claim 12 wherein the vaccine comprises a carrier or an excipient.

14. The method of claim 1, wherein LT is genetically detoxified.

15. The method of claim 1 or 2, wherein LT is a mutant form of the enterotoxin.

16. The method of claim 1 or 2, wherein LT is both an antigen and an adjuvant.

17. The method of claim 16, wherein LT is a mutant form of the enterotoxin.

* * * * *

UNITED STATES PATENT AND TRADEMARK OFFICE
CERTIFICATE OF CORRECTION

PATENT NO. : 7,527,802 B2 Page 1 of 1
APPLICATION NO. : 10/467887
DATED : May 5, 2009
INVENTOR(S) : Gregory M. Glenn et al.

It is certified that error appears in the above-identified patent and that said Letters Patent is hereby corrected as shown below:

Column 6, line 65, after "mice" please delete "was" and insert therefore --were--;

Column 54, line 48, after "known to" please insert --be--;

Column 54, line 57, please delete "transcutaneously" and insert therefore --transcutaneous--;

Column 58, line 32, please delete "know" and insert therefore --known--;

Column 64, claim 2, line 1, please delete "preventing" and insert therefore --treating--; and Column 64, claim 6, line 3, after "CS2", please insert --CS3--.

Signed and Sealed this

Tenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,527,802 B2
APPLICATION NO. : 10/467887
DATED : May 5, 2009
INVENTOR(S) : Gregory M. Glenn et al.

Page 1 of 1

It is certified that error appears in the above-identified patent and that said Letters Patent is hereby corrected as shown below:

Column 6, line 65, after "mice" please delete "was" and insert therefore --were--;

Column 54, line 48, after "known to" please insert --be--;

Column 54, line 57, please delete "transcutaneously" and insert therefore --transcutaneous--;

Column 58, line 32, please delete "know" and insert therefore --known--;

Column 64, claim 2, line 49, please delete "preventing" and insert therefore --treating--; and Column 64, claim 6, line 65, after "CS2", please insert --CS3--.

This certificate supersedes the Certificate of Correction issued November 10, 2009.

Signed and Sealed this

First Day of December, 2009

David J. Kappos
*Director of the United States Patent and Trademark Office*